United States Patent [19]

Wensvoort et al.

[11] Patent Number: 5,620,691
[45] Date of Patent: Apr. 15, 1997

[54] CAUSATIVE AGENT OF THE MYSTERY SWINE DISEASE, VACCINE COMPOSITIONS AND DIAGNOSTIC KITS

[75] Inventors: Gert Wensvoort, Havelte; Catharinus Terpstra; Joannes M. A. Pol, both of Lelystad, all of Netherlands

[73] Assignee: Stichting Centraal Diergeneeskundig Instituut, Lelystad, Netherlands

[21] Appl. No.: 157,005

[22] PCT Filed: Jun. 5, 1992

[86] PCT No.: PCT/NL92/00096

§ 371 Date: Nov. 26, 1993

§ 102(e) Date: Nov. 26, 1993

[87] PCT Pub. No.: WO92/21375

PCT Pub. Date: Dec. 10, 1992

[30] Foreign Application Priority Data

Jun. 6, 1991 [EP] European Pat. Off. .............. 91201398
Mar. 18, 1992 [EP] European Pat. Off. .............. 92200781

[51] Int. Cl.$^6$ .................... A61K 39/00; A61K 31/193; A61K 39/38; A61K 39/12
[52] U.S. Cl. .................... 424/184.1; 424/218.1; 424/221.1; 424/204.1; 424/815
[58] Field of Search ............... 424/218.1, 221.1, 424/204.1, 815, 184.1

[56] References Cited

U.S. PATENT DOCUMENTS 5,476,778  12/1995  Chladek et al. ...................... 435/235.1
5,510,258   4/1996  Sanderson et al. ..................... 435/237

FOREIGN PATENT DOCUMENTS 0592584    8/1992   European Pat. Off. .
0587780B1  3/1994   European Pat. Off. .
0610250B1  12/1995  European Pat. Off. .
2282811    4/1995   United Kingdom .
9303760    3/1993   WIPO .
WO96/06619 3/1996   WIPO .

OTHER PUBLICATIONS

Terpstra et al "Experimental reproduction of porcine epidemic abortion . . . " The Veterinary Quarterly, vol. 13, No. 3, Jul. 1991, pp. 131–136.

"Pathological, ultrastructural, and immunohistochemical changes caused by . . . " The Veterinary Quarterly, vol. 13, No. 3, Jul. 1991, pp. 137–143.

Wensvoort et al "Blue ear" disease, The Veterinary Record, vol. 128, No. 128, Jun. 15, 1991, column, 1, letter, p. 574.

Wensvoort et al "Mystery swine disease in the Netherlands: the isolation of Lelystad virus", The Veterinary Quarterly, vol. 13, No. 3, Jul. 1991, pp. 121–130.

Saif LJ. Veterinary Microbiology 37:285–297, 1993.

Scott FW. Adv. Exp. Med. Biol 218:569–576, 1987.

Martin et al, Can J Comp Med 49(1):1–9, 1985.

Beale AJ, "Vaccines and antiviral drugs", Topley & Wilson's *Principles of bacteriology, virology and immunity*, vol. 4, Ch. 86, pp. 147–161.

Brinton MA, "Lactate Dehydrogenase–Elevating, Equine Arteritis and Lelystad Viruses", *Encyclopedia of Virology*, vol. 2, pp. 763–771.

Christianson et al., "Porcine reproductive and respiratory syndrome: A review", *Swine Health and Production*, vol. 2, No. 2, pp. 10–28, Mar. and Apr., 1994.

Den Boon et al., "Equine Arteritis Virus Is Not a Togavirus but Belongs to the Coronaviruslike Superfamily", *Journal of Virology*, vol. 65, No. 6, pp. 2910–2920, 1991.

Dykhuizen et al., "Determining the Economic Impact of the 'New' Pig Disease", *Porcine Reproductive and Respiratory Syndrome*, A Report on the Seminar Held in Brussels on 4–5 Nov. 1991 and Organized by the European Commission, pp. 53–60.

Fenner et al., "Viral Genetics and Evolution", *Veterinary Virology*, Ch. 5, pp. 89–95.

Fenner et al., "Immunization against Viral Diseases", *Veterinary Virology*, Ch. 14, pp. 265–271.

Meredith MJ, "Porcine Reproductive and Respiratory Syndrome (PRRS)", Pig Disease Information Center, 1st North American Edition, Universtiy of Cambridge, pp. 1–57, Aug. 1994.

Polson et al., "An evalutation of the financial impact of Porcine Reproductive and Respiratory Syndrome (PRRS) in nursery pigs", *Proceedings of the 13th International Pig Veterinary Society Congress*, p. 31, Jun. 1994.

Polson DD, "Answers to Your Questions on PRRS", NOBL Laboratories, 18 pages.

Polson DD, "RespPRRS A PRRS Vaccine Review", NOBL Laboratories, 22 pages.

Snijder et al., "The carboxyl–terminal part of the putative Berne virus polymerase is expressed by ribosomal frameshifting and contains sequence motifs which indicate that toro– and coronaviruses are evolutionarily related", *Nucleic Acids Research*, vol. 18, No. 15, pp. 4535–4542, 1990.

Timony PJ, "Equine Viral Arteritis", *Manual of Standards for Diagnostic Tests and Vaccines*, pp. 493–499, 1992.

"Revision of the taxonomy of the Coronavirus, Torovirus and Arterivirus genera", *Arch Virol*, vol. 135, pp. 227–239, Virology Division News, 1994.

Wenswoort et al., "Antigenic comparison of Lelystad virus and swine infertility and respiratory syndrome (SIRS) virus", *J. Vet Diagn Invest*, vol. 4, pp. 134–138, 1992.

Wenswoort et al., "The Porcine Reproductive and Respiratory Syndrome; Characteristics and diagnosis of the causative virus", *Veterinary Biotechnology Newsletter*, vol. 3, pp. 113–120, 1993.

(List continued on next page.)

*Primary Examiner*—James C. Housel
*Assistant Examiner*—N. M. Minnifield
*Attorney, Agent, or Firm*—Trask, Britt & Rossa

[57] ABSTRACT

Composition of matter comprising the causative agent of Mystery Swine Disease, Lelystad Agent, in a live, attenuated, dead, or recombinant form, or a part or component of it. Vaccine compositions and diagnostic kits based thereon. Recombinant nucleic acid comprising a Lelystad Agent–specific nucleotide sequence. Peptides comprising a Lelystad Agent–specific amino acid sequence. Lelystad Agent–specific antibodies.

10 Claims, 19 Drawing Sheets

OTHER PUBLICATIONS

Murphy et al "Immunization Against Virus" in *Virology* 2nd ed, vol. 1, Fields et al eds. Raven Press, N.Y. 1990 pp. 469–502.

Notice of Opposition by Akzo Nobel against European Patent No. 0 587 780, Nov. 28, 1995, EP.

Notice of Opposition by Cyandmid Iberica against European Patent No. 0 587 780, Nov. 28, 1995, EP.

Abstracts of Papers Presented at the 71st Annual Meeting of the Conference of Research Workers in Animal Disease, No.'s 1–6, Nov. 5,6, 1990, 2 pages.

"Advances in Veterinary Virology 2", *Veterinary Microbiology*, 33(1992), pp. 185–193.

Boursnell et al., "Completion of the Sequence of the Genome of the Coronavirus Avian Infectious Bronchitis Virus", Journal of General Virology 68, 1986, pp. 57–77.

Christianson et al., "Experimental reproduction of swine infertility and respiratory syndrome in pregnant sows", *Am J Vet Res.*, vol. 53, No. 4, Apr. 1992, pp. 485–488.

Collins et al., "Isolation of swine infertility and respiratory syndrome virus (isolate ATCC VR–2332) in North America and experimental reproduction of the disease in gnotobiotic pigs", *J Vet Diagn Invest*, 4:117–126 (1992).

Den Boon et al., "Equine Arteritis Virus Is Not a Togavirus but Belongs to the Cononaviruslike Superfamily", *Journal of Virology*, vol. 65, No. 6, Jun. 1991, pp. 2910–2920.

de Vries et al., "All subgenomic mRNAs of equine arteritis virus contain a common leader sequence", *Nucleic Acids Research*, vol. 18, No. 11, 1990, pp. 3241–3247.

"Diseases Of Swine", Sixth Edition, Iowa State University Press, 1986, pp. 244–315.

Duran et al., "Recombinant Baculovirus Vaccines Against Porcine Reproductive And Respiratory Syndrome (PRRS)", *Abstract PRRS*, Aug. 9th to 10th, 1995, Copenhagen, Denmark, 2 pages.

Godeny et al., "Map Location of Lactate Dehydrogenase–Elevating Virus (LDV) Capsid Protein (Vp1) Gene", *Virology* 177, (1990), pp. 768–771 (1990).

Godeny et al., "The 3' Terminus of Lactate Dehydrogenase–Elevating Virus Genome RNA Does Not Contain Togavirus or Flavivirus Conserved Sequences", *Virology 172*, pp. 647–650.

Joo et al., "Encephalomyocarditis Virus As A Potential Cause For Mystery Swine Disease", *Livestock Conservation Institute*, Denver, Co, pp. 62–66, Oct. 6, 1990.

Kuo et al., "A Nested Set of Eight RNAs Is Formed in Macrophages Infected with Lactate Dehydrogenase–Elevating Virus", *Journal of Virology*, vol. 65, No. 9, Sep. 1991, pp. 5118–5123.

Keffaber, K., "Reproductive Failure of Unknown Etiology", *AASP Newsletter*, vol. 1, No. 2, Sept.–Oct. 1989, pp. 1,4–5, 8–10.

Loula, Timothy, "Mystery Pig Disease", *Agri–Practice*, vol. 12, No. 1, pp. 29–34, Jan./Feb. 1991, 7 pages.

Mc Cullough et al., "9. Experimental Transmission Of Mystery Swine Disease", *The New Pig Disease Porcine Respiration And Reproductive Syndrome*, A report on the seminar/workshop held in Brussels on 29–30 Apr., 1991, pp. 46–52.

Moormann et al., "Molecular Cloning and Nucleotide Sequence of Hog Cholera Virus Strain Brescia and Mapping of the Genomic Region Encoding Envelope Protein E1[1]", *Virology 177*, pp. 184–198 (1990).

Morrison et al., "Brief Communications Serologic evidence incriminating a recently isolated virus (ATCC VR–2332) as the cause of swine infertility and respiratory syndrome (SIRS)", *J Vet Diagn Invest*, 4:186–188 (1992).

Pol et al., "Pathological, ultrastructural, and immunohistochemical changes caused by Lelystad virus in experimentally induced infections of mystery swine disease (synonym: porcine epidemic abortion and respiratory syndrome (PEARS)", *The Veterinary Quarterly*, vol. 13, No. 3, Jul. 1991, pp. 137–143.

Polson et al., "Financial Implications of Mystery Swine Disease (MSD)", pp. 8–28.

Terpstra et al., "Experimental reproduction of porcine epidemic abortion and respiratory syndrome (mystery swine disease) by infection with Lelystad virus: Koch's postulates fulfilled", *The Veterinary Quarterly*, vol. 13, No. 3, Jul. 1991, pp. 131–136.

van Zijl et al., "Live Attenuated Pseudorabies Virus Expressing Envelope Glycoprotein E1 of Hog Cholera Virus Protects Swine against both Pseudorabies and Hog Cholera", *Journal of Virology*, vol. 65, No. 5, May 1991, pp. 2761–2765.

*Veterinary Bulletin*, vol. 58, No. 11, 1988, No's 6903–6909, page 932.

*Veterinary Bulletin*, vol. 60, No. 3, 1990, No.'s 1536–1551, pp. 255–256.

Visser, Nicolaas, "Declaration Of Dr. N. Visser", Nov. 14, 1995, pp. 1–11.

Wardley et al., "The Host Response to African Swine Fever Virus", *Prog. med. Virol.*, vol. 34, pp. 180–192 (1987).

Wensvoort et al., "Mystery swine disease in the Netherlands: the isolation of Lelystad virus", *The Veterinary Quarterly*, vol. 13, No. 3, Jul. 1991, pp. 121–130.

Yoon et al., "Isolation of a cytophathic virus from weak pigs on farms with a history of swine infertility and respiratory syndrome", *J. Vet Diagn Invest*, 4:139–143 (1992).

Response to Opposition to European Patent No. 0 587 780: Aug. 30, 1996.

FIG. 1a

```
GGGTATTCCCCCTACATACACGACACTTCTAGTGTTTGTGTACCTTGGAGGCGTGGGTAC        60
                                 25
AGCCCCGCCCCACCCCTTGGCCCCTGTTCTAGCCCAACAGGTATCCTTCTCTCTGGGGC        120

GAGTGCGCCGCCTGCTGCTCCCTTGCAGCGGGAAGGACCTCCCGAGTATTTCCGGAGAGC       180

ACCTGCTTTACGGGATCTCCACCCTTTAACCATGTCTGGGACGTTCTCCCGGTGCATGTG       240
                ORF1A       M   S   G   T   F   S   R   C   M   C    10

CACCCCGGCTGCCCGGGTATTTTGGAACGCCGGCCAAGTCTTTTGCACACGGTGTCTCAG       300
 T   P   A   A   R   V   F   W   N   A   G   Q   V   F   C   T   R   C   L   S    30

TGCGCGGTCTCTTCTCTCTCCAGAGCTTCAGGACACTGACCTCGGTGCAGTTGGCTTGTT       360
 A   R   S   L   L   S   P   E   L   Q   D   T   D   L   G   A   V   G   L   F    50

TTACAAGCCTAGGGACAAGCTTCACTGGAAAGTCCCTATCGGCATCCCTCAGGTGGAATG       420
 Y   K   P   R   D   K   L   H   W   K   V   P   I   G   I   P   Q   V   E   C    70

TACTCCATCCGGGTGCTGTTGGCTCTCAGCTGTTTTCCCTTTGGCGCGTATGACCTCCGG       480
 T   P   S   G   C   W   L   S   A   V   F   P   L   A   R   M   T   S   G        90

CAATCACAACTTCCTCCAACGACTTGTGAAGGTTGCTGATGTTTTGTACCGTGACGGTTG       540
 N   H   N   F   L   Q   R   L   V   K   V   A   D   V   L   Y   R   D   G   C   110

CTTGGCACCTCGACACCTTCGTGAACTCCAAGTTTACGAGCGCGGCTGCAACTGGTACCC       600
 L   A   P   R   H   L   R   E   L   Q   V   Y   E   R   G   C   N   W   Y   P   130

GATCACGGGGCCCGTGCCCGGGATGGGTTTGTTTGCGAACTCCATGCACGTATCCGACCA       660
 I   T   G   P   V   P   G   M   G   L   F   A   N   S   M   H   V   S   D   Q   150

GCCGTTCCCTGGTGCCACCCATGTGTTGACTAACTCGCCTTTGCCTCAACAGGCTTGTCG       720
 P   F   P   G   A   T   H   V   L   T   N   S   P   L   P   Q   Q   A   C   R   170

GCAGCCGTTCTGTCCATTTGAGGAGGCTCATTCTAGCGTGTACAGGTGGAAGAAATTTGT       780
 Q   P   F   C   P   F   E   E   A   H   S   S   V   Y   R   W   K   K   F   V   190

GGTTTTCACGGACTCCTCCCTCAACGGTCGATCTCGCATGATGTGGACGCCGGAATCCGA       840
 V   F   T   D   S   S   L   N   G   R   S   R   M   M   W   T   P   E   S   D   210

TGATTCAGCCGCCCTGGAGGTACTACCGCCTGAGTTAGAACGTCAGGTCGAAATCCTCAT       900
 D   S   A   A   L   E   V   L   P   P   E   L   E   R   Q   V   E   I   L   I   230

TCGGAGTTTTCCTGCTCATCACCCTGTCGACCTGGCCGACTGGGAGCTCACTGAGTCCCC       960
 R   S   F   P   A   H   H   P   V   D   L   A   D   W   E   L   T   E   S   P   250

TGAGAACGGTTTTTCCTTCAACACGTCTCATTCTTGCGGTCACCTTGTCCAGAACCCCGA      1020
 E   N   G   F   S   F   N   T   S   H   S   C   G   H   L   V   Q   N   P   D   270
```

FIG. 1b

```
CGTGTTTGATGGCAAGTGCTGGCTCTCCTGCTTTTTGGGCCAGTCGGTCGAAGTGCGCTG    1080
  V  F  D  G  K  C  W  L  S  C  F  L  G  Q  S  V  E  V  R  C       290

CCATGAGGAACATCTAGCTGACGCCTTCGGTTACCAAACCAAGTGGGGCGTGCATGGTAA    1140
  H  E  E  H  L  A  D  A  F  G  Y  Q  T  K  W  G  V  H  G  K       310

GTACCTCCAGCGCAGGCTTCAAGTTCGCGGCATTCGTGCTGTAGTCGATCCTGATGGTCC    1200
  Y  L  Q  R  R  L  Q  V  R  G  I  R  A  V  V  D  P  D  G  P       330

CATTCACGTTGAAGCGCTGTCTTGCCCCCAGTCTTGGATCAGGCACCTGACTCTGGATGA    1260
  I  H  V  E  A  L  S  C  P  Q  S  W  I  R  H  L  T  L  D  D       350

TGATGTCACCCCAGGATTCGTTCGCCTGACATCCCTTCGCATTGTGCCGAACACAGAGCC    1320
  D  V  T  P  G  F  V  R  L  T  S  L  R  I  V  P  N  T  E  P       370

TACCACTTCCCGGATCTTTCGGTTTGGAGCGCATAAGTGGTATGGCGCTGCCGGCAAACG    1380
  T  T  S  R  I  F  R  F  G  A  H  K  W  Y  G  A  A  G  K  R       390

GGCTCGTGCTAAGCGTGCCGCTAAAAGTGAGAAGGATTCGGCTCCCACCCCCAAGGTTGC    1440
  A  R  A  K  R  A  A  K  S  E  K  D  S  A  P  T  P  K  V  A       410

CCTGCCGGTCCCCACCTGTGGAATTACCACCTACTCTCCACCGACAGACGGGTCTTGTGG    1500
  L  P  V  P  T  C  G  I  T  T  Y  S  P  P  T  D  G  S  C  G       430

TTGGCATGTCCTTGCCGCCATAATGAACCGGATGATAAATGGTGACTTCACGTCCCCTCT    1560
  W  H  V  L  A  A  I  M  N  R  M  I  N  G  D  F  T  S  P  L       450

GACTCAGTACAACAGACCAGAGGATGATTGGGCTTCTGATTATGATCTTGTTCAGGCGAT    1620
  T  Q  Y  N  R  P  E  D  D  W  A  S  D  Y  D  L  V  Q  A  I       470

TCAATGTCTACGACTGCCTGCTACCGTGGTTCGGAATCGCGCCTGTCCTAACGCCAAGTA    1680
  Q  C  L  R  L  P  A  T  V  V  R  N  R  A  C  P  N  A  K  Y       490

CCTTATAAAACTTAACGGAGTTCACTGGGAGGTAGAGGTGAGGTCTGGAATGGCTCCTCG    1740
  L  I  K  L  N  G  V  H  W  E  V  E  V  R  S  G  M  A  P  R       510

CTCCCTTTCTCGTGAATGTGTGGTTGGCGTTTGCTCTGAAGGCTGTGTCGCACCGCCTTA    1800
  S  L  S  R  E  C  V  V  G  V  C  S  E  G  C  V  A  P  P  Y       530

TCCAGCAGACGGGCTACCTAAACGTGCACTCGAGGCCTTGGCGTCTGCTTACAGACTACC    1860
  P  A  D  G  L  P  K  R  A  L  E  A  L  A  S  A  Y  R  L  P       550

CTCCGATTGTGTTAGCTCTGGTATTGCTGACTTTCTTGCTAATCCACCTCCTCAGGAATT    1920
  S  D  C  V  S  S  G  I  A  D  F  L  A  N  P  P  P  Q  E  F       570

CTGGACCCTCGACAAAATGTTGACCTCCCCGTCACCAGAGCGGTCCGGCTTCTCTAGTTT    1980
  W  T  L  D  K  M  L  T  S  P  S  P  E  R  S  G  F  S  S  L       590
```

FIG. 1c

```
GTATAAATTACTATTAGAGGTTGTTCCGCAAAAATGCGGTGCCACGGAAGGGGCTTTCAT    2040
  Y  K  L  L  E  V  V  P  Q  K  C  G  A  T  E  G  A  F  I       610

CTATGCTGTTGAGAGGATGTTGAAGGATTGTCCGAGCTCCAAACAGGCCATGGCCCTTCT    2100
  Y  A  V  E  R  M  L  K  D  C  P  S  S  K  Q  A  M  A  L  L    630

GGCAAAAATTAAAGTTCCATCCTCAAAGGCCCCGTCTGTGTCCCTGGACGAGTGTTTCCC    2160
  A  K  I  K  V  P  S  S  K  A  P  S  V  S  L  D  E  C  F  P    650

TACGGATGTTTTAGCCGACTTCGAGCCAGCATCTCAGGAAAGGCCCCAAAGTTCCGGCGC    2220
  T  D  V  L  A  D  F  E  P  A  S  Q  E  R  P  Q  S  S  G  A    670
                                                           A
TGCTGTTGTCCTGTGTTCACCGGATGCAAAAGAGTTCGAGGAAGCAGCCCCGGAAGAAGT    2280
  A  V  V  L  C  S  P  D  A  K  E  F  E  E  A  A  P  E  E  V    690

TCAAGAGAGTGGCCACAAGGCCGTCCACTCTGCACTCCTTGCCGAGGGTCCTAACAATGA    2340
  Q  E  S  G  H  K  A  V  H  S  A  L  L  A  E  G  P  N  N  E    710

GCAGGTACAGGTGGTTGCCGGTGAGCAACTGAAGCTCGGCGGTTGTGGTTTGGCAGTCGG    2400
  Q  V  Q  V  V  A  G  E  Q  L  K  L  G  G  C  G  L  A  V  G    730

GAATGCTCATGAAGGTGCTCTGGTCTCAGCTGGTCTAATTAACCTGGTAGGCGGGAATTT    2460
  N  A  H  E  G  A  L  V  S  A  G  L  I  N  L  V  G  G  N  L    750

GTCCCCCTCAGACCCCATGAAAGAAAACATGCTCAATAGCCGGGAAGACGAACCACTGGA    2520
  S  P  S  D  P  M  K  E  N  M  L  N  S  R  E  D  E  P  L  D    770

TTTGTCCCAACCAGCACCAGCTTCCACAACGACCCTTGTGAGAGAGCAAACACCCGACAA    2580
  L  S  Q  P  A  P  A  S  T  T  T  L  V  R  E  Q  T  P  D  N    790

CCCAGGTTCTGATGCCGGTGCCCTCCCCGTCACCGTTCGAGAATTTGTCCCGACGGGGCC    2640
  P  G  S  D  A  G  A  L  P  V  T  V  R  E  F  V  P  T  G  P    810

TATACTCTGTCATGTTGAGCACTGCGGCACGGAGTCGGGCGACAGCAGTTCGCCTTTGGA    2700
  I  L  C  H  V  E  H  C  G  T  E  S  G  D  S  S  P  L  D       830

TCTATCTGATGCGCAAACCCTGGACCAGCCTTTAAATCTATCCCTGGCCGCTTGGCCAGT    2760
  L  S  D  A  Q  T  L  D  Q  P  L  N  L  S  L  A  A  W  P  V    850

GAGGGCCACCGCGTCTGACCCTGGCTGGGTCCACGGTAGGCGCGAGCCTGTCTTTGTAAA    2820
  R  A  T  A  S  D  P  G  W  V  H  G  R  R  E  P  V  F  V  K    870

GCCTCGAAATGCTTTCTCTGATGGCGATTCAGCCCTTCAGTTCGGGGAGCTTTCTGAATC    2880
  P  R  N  A  F  S  D  G  D  S  A  L  Q  F  G  E  L  S  E  S    890
```

FIG. 1d

| | |
|---|---|
| CAGCTCTGTCATCGAGTTTGACCGGACAAAAGATGCTCCGGTGGTTGACGCCCCTGTCGA | 2940 |
| S  S  V  I  E  F  D  R  T  K  D  A  P  V  V  D  A  P  V  D | 910 |
| CTTGACGACTTCGAACGAGGCCCTCTCTGTAGTCGATCCTTTCGAATTTGCCGAACTCAA | 3000 |
| L  T  T  S  N  E  A  L  S  V  V  D  P  F  E  F  A  E  L  K | 930 |
| GCGCCCGCGTTTCTCCGCACAAGCCTTAATTGACCGAGGCGGTCCACTTGCCGATGTCCA | 3060 |
| R  P  R  F  S  A  Q  A  L  I  D  R  G  G  P  L  A  D  V  H | 950 |
| TGCAAAAATAAAGAACCGGGTATATGAACAGTGCCTCCAAGCTTGTGAGCCCGGTAGTCG | 3120 |
| A  K  I  K  N  R  V  Y  E  Q  C  L  Q  A  C  E  P  G  S  R | 970 |
| TGCAACCCCAGCCACCAGGGAGTGGCTCGACAAAATGTGGGATAGGGTGGACATGAAAAC | 3180 |
| A  T  P  A  T  R  E  W  L  D  K  M  W  D  R  V  D  M  K  T | 990 |
| TTGGCGCTGCACCTCGCAGTTCCAAGCTGGTCGCATTCTTGCGTCCCTCAAATTCCTCCC | 3240 |
| W  R  C  T  S  Q  F  Q  A  G  R  I  L  A  S  L  K  F  L  P | 1010 |
| TGACATGATTCAAGACACACCGCCTCCTGTTCCCAGGAAGAACCGAGCTAGTGACAATGC | 3300 |
| D  M  I  Q  D  T  P  P  P  V  P  R  K  N  R  A  S  D  N  A | 1030 |
| CGGCCTGAAGCAACTGGTGGCACAGTGGGATAGGAAATTGAGTGTGACCCCCCCCCCAAA | 3360 |
| G  L  K  Q  L  V  A  Q  W  D  R  K  L  S  V  T  P  P  P  K | 1050 |
| ACCGGTTGGGCCAGTGCTTGACCAGATCGTCCCTCCGCCTACGGATATCCAGCAAGAAGA | 3420 |
| P  V  G  P  V  L  D  Q  I  V  P  P  P  T  D  I  Q  Q  E  D | 1070 |
| TGTCACCCCCTCCGATGGGCCACCCCATGCGCCGGATTTTCCTAGTCGAGTGAGCACGGG | 3480 |
| V  T  P  S  D  G  P  P  H  A  P  D  F  P  S  R  V  S  T  G | 1090 |
| CGGGAGTTGGAAAGGCCTTATGCTTTCCGGCACCCGTCTCGCGGGGTCTATCAGCCAGCG | 3540 |
| G  S  W  K  G  L  M  L  S  G  T  R  L  A  G  S  I  S  Q  R | 1110 |
| CCTTATGACATGGGTTTTTGAAGTTTTCTCCCACCTCCCAGCTTTTATGCTCACACTTTT | 3600 |
| L  M  T  W  V  F  E  V  F  S  H  L  P  A  F  M  L  T  L  F | 1130 |
| CTCGCCGCGGGGCTCTATGGCTCCAGGTGATTGGTTGTTTGCAGGTGTCGTTTTACTTGC | 3660 |
| S  P  R  G  S  M  A  P  G  D  W  L  F  A  G  V  V  L  L  A | 1150 |
| TCTCTTGCTCTGTCGTTCTTACCCGATACTCGGATGCCTTCCCTTATTGGGTGTCTTTTC | 3720 |
| L  L  L  C  R  S  Y  P  I  L  G  C  L  P  L  L  G  V  F  S | 1170 |
| TGGTTCTTTGCGGCGTGTTCGTCTGGGTGTTTTGGTTCTTGGATGGCTTTTGCTGTATT | 3780 |
| G  S  L  R  R  V  R  L  G  V  F  G  S  W  M  A  F  A  V  F | 1190 |
| TTTATTCTCGACTCCATCCAACCCAGTCGGTTCTTCTTGTGACCACGATTCGCCGGAGTG | 3840 |
| L  F  S  T  P  S  N  P  V  G  S  S  C  D  H  D  S  P  E  C | 1210 |

FIG. 1e

```
TCATGCTGAGCTTTTGGCTCTTGAGCAGCGCCAACTTTGGGAACCTGTGCGCGGCCTTGT    3900
  H   A   E   L   L   A   L   E   Q   R   Q   L   W   E   P   V   R   G   L   V    1230

GGTCGGCCCCTCAGGCCTCTTATGTGTCATTCTTGGCAAGTTACTCGGTGGGTCACGTTA    3960
  V   G   P   S   G   L   L   C   V   I   L   G   K   L   L   G   G   S   R   Y    1250

TCTCTGGCATGTTCTCCTACGTTTATGCATGCTTGCAGATTTGGCCCTTTCTCTTGTTTA    4020
  L   W   H   V   L   L   R   L   C   M   L   A   D   L   A   L   S   L   V   Y    1270

TGTGGTGTCCCAGGGGCGTTGTCACAAGTGTTGGGGAAAGTGTATAAGGACAGCTCCTGC    4080
  V   V   S   Q   G   R   C   H   K   C   W   G   K   C   I   R   T   A   P   A    1290

GGAGGTGGCTCTTAATGTATTTCCTTTCTCGCGCGCCACCCGTGTCTCTCTTGTATCCTT    4140
  E   V   A   L   N   V   F   P   F   S   R   A   T   R   V   S   L   V   S   L    1310

GTGTGATCGATTCCAAACGCCAAAAGGGGTTGATCCTGTGCACTTGGCAACGGGTTGGCG    4200
  C   D   R   F   Q   T   P   K   G   V   D   P   V   H   L   A   T   G   W   R    1330

CGGGTGCTGGCGTGGTGAGAGCCCCATCCATCAACCACACCAAAAGCCCATAGCTTATGC    4260
  G   C   W   R   G   E   S   P   I   H   Q   P   H   Q   K   P   I   A   Y   A    1350

CAATTTGGATGAAAAGAAAATGTCTGCCCAAACGGTGGTTGCTGTCCCATACGATCCCAG    4320
  N   L   D   E   K   K   M   S   A   Q   T   V   V   A   V   P   Y   D   P   S    1370

TCAGGCTATCAAATGCCTGAAAGTTCTGCAGGCGGGAGGGGCCATCGTGGACCAGCCTAC    4380
  Q   A   I   K   C   L   K   V   L   Q   A   G   G   A   I   V   D   Q   P   T    1390

ACCTGAGGTCGTTCGTGTGTCCGAGATCCCCTTCTCAGCCCCATTTTTCCCAAAAGTTCC    4440
  P   E   V   V   R   V   S   E   I   P   F   S   A   P   F   F   P   K   V   P    1410

AGTCAACCCAGATTGCAGGGTTGTGGTAGATTCGGACACTTTTGTGGCTGCGGTTCGCTG    4500
  V   N   P   D   C   R   V   V   V   D   S   D   T   F   V   A   A   V   R   C    1430
                                                            C
CGGTTACTCGACAGCACAACTGGTTCTGGGCCGGGGCAACTTTGCCAAGTTAAATCAGAC    4560
  G   Y   S   T   A   Q   L   V   L   G   R   G   N   F   A   K   L   N   Q   T    1450

CCCCCCCAGGAACTCTATCTCCACCAAAACGACTGGTGGGGCCTCTTACACCCTTGCTGT    4620
  P   P   R   N   S   I   S   T   K   T   T   G   G   A   S   Y   T   L   A   V    1470

GGCTCAAGTGTCTGCGTGGACTCTTGTTCATTTCATCCTCGGTCTTTGGTTCACATCACC    4680
  A   Q   V   S   A   W   T   L   V   H   F   I   L   G   L   W   F   T   S   P    1490

TCAAGTGTGTGGCCGAGGAACCGCTGACCCATGGTGTTCAAATCCTTTTTCATATCCTAC    4740
  Q   V   C   G   R   G   T   A   D   P   W   C   S   N   P   F   S   Y   P   T    1510

CTATGGCCCCGGAGTTGTGTGCTCCTCTCGACTTTGTGTGTCTGCCGACGGGGTCACCCT    4800
  Y   G   P   G   V   V   C   S   S   R   L   C   V   S   A   D   G   V   T   L    1530
```

FIG. 1f

```
GCCATTGTTCTCAGCCGTGGCACAACTCTCCGGTAGAGAGGTGGGGATTTTTATTTTGGT    4860
  P   L   F   S   A   V   A   Q   L   S   G   R   E   V   G   I   F   I   L   V   1550

GCTCGTCTCCTTGACTGCTTTGGCCCACCGCATGGCTCTTAAGGCAGACATGTTAGTGGT    4920
  L   V   S   L   T   A   L   A   H   R   M   A   L   K   A   D   M   L   V   V   1570

CTTTTCGGCTTTTTGTGCTTACGCCTGGCCCATGAGCTCCTGGTTAATCTGCTTCTTTCC    4980
  F   S   A   F   C   A   Y   A   W   P   M   S   S   W   L   I   C   F   F   P   1590

TATACTCTTGAAGTGGGTTACCCTTCACCCTCTTACTATGCTTTGGGTGCACTCATTCTT    5040
  I   L   L   K   W   V   T   L   H   P   L   T   M   L   W   V   H   S   F   L   1610

GGTGTTTTGTCTGCCAGCAGCCGGCATCCTCTCACTAGGGATAACTGGCCTTCTTTGGGC    5100
  V   F   C   L   P   A   A   G   I   L   S   L   G   I   T   G   L   L   W   A   1630

AATTGGCCGCTTTACCCAGGTTGCCGGAATTATTACACCTTATGACATCCACCAGTACAC    5160
  I   G   R   F   T   Q   V   A   G   I   I   T   P   Y   D   I   H   Q   Y   T   1650

CTCTGGGCCACGTGGTGCAGCTGCTGTGGCCACAGCCCCAGAAGGCACTTATATGGCCGC    5220
  S   G   P   R   G   A   A   A   V   A   T   A   P   E   G   T   Y   M   A   A   1670

CGTCCGGAGAGCTGCTTTAACTGGGCGAACTTTAATCTTCACCCCGTCTGCAGTTGGATC    5280
  V   R   R   A   A   L   T   G   R   T   L   I   F   T   P   S   A   V   G   S   1690

CCTTCTCGAAGGTGCTTTCAGGACTCATAAACCCTGCCTTAACACCGTGAATGTTGTAGG    5340
  L   L   E   G   A   F   R   T   H   K   P   C   L   N   T   V   N   V   V   G   1710

CTCTTCCCTTGGTTCCGGAGGGGTTTTCACCATTGATGGCAGAAGAACTGTCGTCACTGC    5400
  S   S   L   G   S   G   G   V   F   T   I   D   G   R   R   T   V   V   T   A   1730

TGCCCATGTGTTGAACGGCGACACAGCTAGAGTCACCGGCGACTCCTACAACCGCATGCA    5460
  A   H   V   L   N   G   D   T   A   R   V   T   G   D   S   Y   N   R   M   H   1750

CACTTTCAAGACCAATGGTGATTATGCCTGGTCCCATGCTGATGACTGGCAGGGCGTTGC    5520
  T   F   K   T   N   G   D   Y   A   W   S   H   A   D   D   W   Q   G   V   A   1770

CCCTGTGGTCAAGGTTGCGAAGGGGTACCGCGGTCGTGCCTACTGGCAAACATCAACTGG    5580
  P   V   V   K   V   A   K   G   Y   R   G   R   A   Y   W   Q   T   S   T   G   1790

TGTCGAACCCGGTATCATTGGGGAAGGGTTCGCCTTCTGTTTTACTAACTGCGGCGATTC    5640
  V   E   P   G   I   I   G   E   G   F   A   F   C   F   T   N   C   G   D   S   1810

GGGGTCACCCGTCATCTCAGAATCTGGTGATCTTATTGGAATCCACACCGGTTCAAACAA    5700
  G   S   P   V   I   S   E   S   G   D   L   I   G   I   H   T   G   S   N   K   1830

ACTTGGTTCTGGTCTTGTGACAACCCCTGAAGGGGAGACCTGCACCATCAAAGAAACCAA    5760
  L   G   S   G   L   V   T   T   P   E   G   E   T   C   T   I   K   E   T   K   1850
```

FIG. 1g

```
GCTCTCTGACCTTTCCAGACATTTTGCAGGCCCAAGCGTTCCTCTTGGGGACATTAAATT    5820
 L  S  D  L  S  R  H  F  A  G  P  S  V  P  L  G  D  I  K  L     1870

GAGTCCGGCCATCATCCCTGATGTAACATCCATTCCGAGTGACTTGGCATCGCTCCTAGC    5880
 S  P  A  I  I  P  D  V  T  S  I  P  S  D  L  A  S  L  L  A     1890

CTCCGTCCCTGTAGTGGAAGGCGGCCTCTCGACCGTTCAACTTTTGTGTGTCTTTTTCCT    5940
 S  V  P  V  V  E  G  G  L  S  T  V  Q  L  L  C  V  F  F  L     1910

TCTCTGGCGCATGATGGGCCATGCCTGGACACCCATTGTTGCCGTGGGCTTCTTTTTGCT    6000
 L  W  R  M  M  G  H  A  W  T  P  I  V  A  V  G  F  F  L  L     1930

GAATGAAATTCTTCCAGCAGTTTTGGTCCGAGCCGTGTTTTCTTTTGCACTCTTTGTGCT    6060
 N  E  I  L  P  A  V  L  V  R  A  V  F  S  F  A  L  F  V  L     1950

TGCATGGGCCACCCCCTGGTCTGCACAGGTGTTGATGATTAGACTCCTCACGGCATCTCT    6120
 A  W  A  T  P  W  S  A  Q  V  L  M  I  R  L  L  T  A  S  L     1970

CAACCGCAACAAGCTTTCTCTGGCGTTCTACGCACTCGGGGGTGTCGTCGGTTTGGCAGC    6180
 N  R  N  K  L  S  L  A  F  Y  A  L  G  G  V  V  G  L  A  A     1990

TGAAATCGGGACTTTTGCTGGCAGATTGTCTGAATTGTCTCAAGCTCTTTCGACATACTG    6240
 E  I  G  T  F  A  G  R  L  S  E  L  S  Q  A  L  S  T  Y  C     2010

CTTCTTACCTAGGGTCCTTGCTATGACCAGTTGTGTTCCCACCATCATCATTGGTGGACT    6300
 F  L  P  R  V  L  A  M  T  S  C  V  P  T  I  I  I  G  L        2030
                         G
CCATACCCTCGGTGTGATTCTGTGGTTATTCAAATACCGGTGCCTCCACAACATGCTGGT    6360
 H  T  L  G  V  I  L  W  L  F  K  Y  R  C  L  H  N  M  L  V     2050

TGGTGATGGGAGTTTTTTCAAGCGCCTTCTTCCTACGGTATTTTGCAGAGGGTAATCTCAG   6420
 G  D  G  S  F  S  S  A  F  F  L  R  Y  F  A  E  G  N  L  R     2070

AAAAGGTGTTTCACAGTCCTGTGGCATGAATAACGAGTCCCTAACGGCTGCTTTAGCTTG    6480
 K  G  V  S  Q  S  C  G  M  N  N  E  S  L  T  A  A  L  A  C     2090

CAAGTTGTCACAGGCTGACCTTGATTTTTTGTCCAGCTTAACGAACTTCAAGTGCTTTGT    6540
 K  L  S  Q  A  D  L  D  F  L  S  S  L  T  N  F  K  C  F  V     2110

ATCTGCTTCAAACATGAAAAATGCTGCCGGCCAGTACATTGAAGCAGCGTATGCCAAGGC    6600
 S  A  S  N  M  K  N  A  A  G  Q  Y  I  E  A  A  Y  A  K  A     2130

CCTGCGCCAAGAGTTGGCCTCTCTAGTTCAGATTGACAAAATGAAAGGAGTTTTGTCCAA    6660
 L  R  Q  E  L  A  S  L  V  Q  I  D  K  M  K  G  V  L  S  K     2150
```

FIG. 1h

```
GCTCGAGGCCTTTGCTGAAACAGCCACCCCGTCCCTTGACATAGGTGACGTGATTGTTCT    6720
  L  E  A  F  A  E  T  A  T  P  S  L  D  I  G  D  V  I  V  L    2170

GCTTGGGCAACATCCTCACGGATCCATCCTCGATATTAATGTGGGGACTGAAAGGAAAAC    6780
  L  G  Q  H  P  H  G  S  I  L  D  I  N  V  G  T  E  R  K  T    2190

TGTGTCCGTGCAAGAGACCCGGAGCCTAGGCGGCTCCAAATTCAGTGTTTGTACTGTCGT    6840
  V  S  V  Q  E  T  R  S  L  G  G  S  K  F  S  V  C  T  V  V    2210
                                        A
GTCCAACACACCCGTGGACGCCTTGACCGGCATCCCACTCCAGACACCAACCCCTCTTTT    6900
  S  N  T  P  V  D  A  L  T  G  I  P  L  Q  T  P  T  P  L  F    2230

TGAGAATGGTCCGCGTCATCGCAGCGAGGAAGACGATCTTAAAGTCGAGAGGATGAAGAA    6960
  E  N  G  P  R  H  R  S  E  E  D  D  L  K  V  E  R  M  K  K    2250

ACACTGTGTATCCCTCGGCTTCCACAACATCAATGGCAAAGTTTACTGCAAAATTTGGGA    7020
  H  C  V  S  L  G  F  H  N  I  N  G  K  V  Y  C  K  I  W  D    2270

CAAGTCTACCGGTGACACCTTTTACACGGATGATTCCCGGTACACCCAAGACCATGCTTT    7080
  K  S  T  G  D  T  F  Y  T  D  D  S  R  Y  T  Q  D  H  A  F    2290

TCAGGACAGGTCAGCCGACTACAGAGACAGGGACTATGAGGGTGTGCAAACCACCCCCCA    7140
  Q  D  R  S  A  D  Y  R  D  R  D  Y  E  G  V  Q  T  T  P  P    2310

ACAGGGATTTGATCCAAAGTCTGAAACCCCTGTTGGCACTGTTGTGATCGGCGGTATTAC    7200
  I  G  G  I  T  Y  Y  E  G  V  Q  T  T  P  Q  Q  G  F  D  P    2330

GTATAACAGGTATCTGATCAAAGGTAAGGAGGTTCTGGTCCCCAAGCCTGACAACTGCCT    7260
  K  N  R  Y  L  I  K  G  K  E  V  L  V  P  K  P  D  N  C  L    2350

TGAAGCTGCCAAGCTGTCCCTTGAGCAAGCTCTCGCTGGGATGGGCCAAACTTGCGACCT    7320
  E  A  A  K  L  S  L  E  Q  A  L  A  G  M  G  Q  T  C  D  L    2370

TACAGCTGCCGAGGTGGAAAAGCTAAAGCGCATCATTAGTCAACTCCAAGGTTTGACCAC    7380
  T  A  A  E  V  E  K  L  K  R  I  I  S  Q  L  Q  G  L  T  T    2390
                                                          ORF1B

TGAACAGGCTTTTAAACTGTTAGCCGCCAGCGGCTTGACCCGCTGTGGCCGCGGCGGCCTA    7440
  E  Q  A  L  N  C  -                                            2396
     -  T  G  F  K  L  L  A  A  S  G  L  T  R  C  G  R  G  G  L    19

GTTGTGACTGAAACGGCGGTAAAAATTATAAAATACCACAGCAGAACTTTCACCTTAGGC    7500
  V  V  T  E  T  A  V  K  I  I  K  Y  H  S  R  T  F  T  L  G      39

CCTTTAGACCTAAAAGTCACTTCCGAGGTGGAGGTAAAGAAATCAACTGAGCAGGGCCAC    7560
  P  L  D  L  K  V  T  S  E  V  E  V  K  K  S  T  E  Q  G  H      59
```

FIG. 1i

```
GCTGTTGTGGCAAACTTATGTTCCGGTGTCATCTTGATGAGACCTCACCCACCGTCCCTT   7620
 A  V  V  A  N  L  C  S  G  V  I  L  M  R  P  H  P  P  S  L      79

GTCGACGTTCTTCTGAAACCCGGACTTGACACAATACCCGGCATTCAACCAGGGCATGGG   7680
 V  D  V  L  L  K  P  G  L  D  T  I  P  G  I  Q  P  G  H  G      99

GCCGGGAATATGGGCGTGGACGGTTCTATTTGGGATTTTGAAACCGCACCCACAAAGGCA   7740
 A  G  N  M  G  V  D  G  S  I  W  D  F  E  T  A  P  T  K  A     119

GAACTCGAGTTATCCAAGCAAATAATCCAAGCATGTGAAGTTAGGCGCGGGGACGCCCCG   7800
 E  L  E  L  S  K  Q  I  I  Q  A  C  E  V  R  R  G  D  A  P     139

AACCTCCAACTCCCTTACAAGCTCTATCCTGTTAGGGGGGATCCTGAGCGGCATAAAGGC   7860
 N  L  Q  L  P  Y  K  L  Y  P  V  R  G  D  P  E  R  H  K  G     159

CGCCTTATCAATACCAGGTTTGGAGATTTACCTTACAAAACTCCTCAAGACACCAAGTCC   7920
 R  L  I  N  T  R  F  G  D  L  P  Y  K  T  P  Q  D  T  K  S     179

GCAATCCACGCGGCTTGTTGCCTGCACCCCAACGGGGCCCCCGTGTCTGATGGTAAATCC   7980
 A  I  H  A  A  C  L  H  P  N  G  A  P  V  S  D  G  K  S        199

ACACTAGGTACCACTCTTCAACATGGTTTCGAGCTTTATGTCCCTACTGTGCCCTATAGT   8040
 T  L  G  T  T  L  Q  H  G  F  E  L  Y  V  P  T  V  P  Y  S     219

GTCATGGAGTACCTTGATTCACGCCCTGACACCCCTTTTATGTGTACTAAACATGGCACT   8100
 V  M  E  Y  L  D  S  R  P  D  T  P  F  M  C  T  K  H  G  T     239

TCCAAGGCTGCTGCAGAGGACCTCCAAAAATACGACCTATCCACCCAAGGATTTGTCCTG   8160
 S  K  F  V  L  P  G  V  L  R  L  V  R  R  F  I  F  A  A  A     259

CCTGGGGTCCTACGCCTAGTACGCAGATTCATCTTTGGCCATATTGGTAAGGCGCCGCCA   8220
 E  D  L  Q  K  Y  D  L  S  T  Q  G  G  H  I  G  K  A  P  P     279

TTGTTCCTCCCATCAACCTATCCCGCCAAGAACTCTATGGCAGGGATCAATGGCCAGAGG   8280
 L  F  L  P  S  T  Y  P  A  K  N  S  M  A  G  I  N  G  Q  R     299

TTCCCAACAAAGGACGTTCAGAGCATACCTGAAATTGATGAAATGTGTGCCCGCGCTGTC   8340
 F  P  T  K  D  V  Q  S  I  P  E  I  D  E  M  C  A  R  A  V     319

AAGGAGAATTGGCAAACTGTGACACCTTGCACCCTCAAGAAACAGTACTGTTCCAAGCCC   8400
 K  E  N  W  Q  T  V  T  P  C  T  L  K  K  Q  Y  C  S  K  P     339

AAAACCAGGACCATCCTGGGCACCAACAACTTTATTGCCTTGGCTCACAGATCGGCGCTC   8460
 K  T  R  T  I  L  G  T  N  N  F  I  A  L  A  H  R  S  A  L     359

AGTGGTGTCACCCAGGCATTCATGAAGAAGGCTTGGAAGTCCCCAATTGCCTTGGGGAAA   8520
 S  G  V  T  Q  A  F  M  K  K  A  W  K  S  P  I  A  L  G  K     379
```

FIG. 1j

```
AACAAATTCAAGGAGCTGCATTGCACTGTCGCCGGCAGGTGTCTTGAGGCCGACTTGGCC    8580
 N  K  F  K  E  L  H  C  T  V  A  G  R  C  L  E  A  D  L  A     399

TCCTGTGACCGCAGCACCCCCGCCATTGTAAGATGGTTTGTTGCCAACCTCCTGTATGAA    8640
 S  C  D  R  S  T  P  A  I  V  R  W  F  V  A  N  L  L  Y  E     419

CTTGCAGGATGTGAAGAGTACTTGCCTAGCTATGTGCTTAATTGCTGCCATGACCTCGTG    8700
 L  A  G  C  E  E  Y  L  P  S  Y  V  L  N  C  C  H  D  L  V     439

GCAACACAGGATGGTGCCTTCACAAAACGCGGTGGCCTGTCGTCCGGGGACCCCGTCACC    8760
 A  T  Q  D  G  A  F  T  K  R  G  G  L  S  S  G  D  P  V  T     459

AGTGTGTCCAACACCGTATATTCACTGGTAATTTATGCCCAGCACATGGTATTGTCGGCC    8820
 S  V  S  N  T  V  Y  S  L  V  I  Y  A  Q  H  M  V  L  S  A     479

TTGAAAATGGGTCATGAAATTGGTCTTAAGTTCCTCGAGGAACAGCTCAAGTTCGAGGAC    8880
 L  K  M  G  H  E  I  G  L  K  F  L  E  E  Q  L  K  F  E  D     499

CTCCTTGAAATTCAGCCTATGTTGGTATACTCTGATGATCTTGTCTTGTACGCTGAAAGA    8940
 L  L  E  I  Q  P  M  L  V  Y  S  D  D  L  V  L  Y  A  E  R     519
                C
CCCACATTTCCCAATTACCACTGGTGGGTCGAGCACCTTGACCTGATGCTGGGTTTCAGA    9000
 P  T  F  P  N  Y  H  W  W  V  E  H  L  D  L  M  L  G  F  R     539

ACGGACCCAAAGAAAACCGTCATAACTGATAAACCCAGCTTCCTCGGCTGCAGAATTGAG    9060
 T  D  P  K  K  T  V  I  T  D  K  P  S  F  L  G  C  R  I  E     559

GCAGGGCGACAGCTAGTCCCCAATCGCGACCGCATCCTGGCTGCTCTTGCATATCACATG    9120
 A  G  R  Q  L  V  P  N  R  D  R  I  L  A  A  L  A  Y  H  M     579

AAGGCGCAGAACGCCTCAGAGTATTATGCGTCTGCTGCCGCAATCCTGATGGATTCATGT    9180
 K  A  Q  N  A  S  E  Y  Y  A  S  A  A  A  I  L  M  D  S  C     599

GCTTGCATTGACCATGACCCTGAGTGGTATGAGGACCTCATCTGCGGTATTGCCCGGTGC    9240
 A  C  I  D  H  D  P  E  W  Y  E  D  L  I  C  G  I  A  R  C     619

GCCCGCCAGGATGGTTATAGCTTCCCAGGTCCGGCATTTTTCATGTCCATGTGGGAGAAG    9300
 A  R  Q  D  G  Y  S  F  P  G  P  A  F  F  M  S  M  W  E  K     639

CTGAGAAGTCATAATGAAGGGAAGAAATTCCGCCACTGCGGCATCTGCGACGCCAAAGCC    9360
 L  R  S  H  N  E  G  K  K  F  R  H  C  G  I  C  D  A  K  A     659

GACTATGCGTCCGCCTGTGGGCTTGATTTGTGTTTGTTCCATTCGCACTTTCATCAACAC    9420
 D  Y  A  S  A  C  G  L  D  L  C  L  F  H  S  H  F  H  Q  H     679
```

FIG. 1k

```
                                    C
TGCCCTGTCACTCTGAGCTGCGGTCACCATGCCGGTTCAAAGGAATGTTCGCAGTGTCAG   9480
 C  P  V  T  L  S  C  G  H  H  A  G  S  K  E  C  S  Q  C  Q    699

TCACCTGTTGGGGCTGGCAGATCCCCTCTTGATGCCGTGCTAAAACAAATTCCATACAAA   9540
 S  P  V  G  A  G  R  S  P  L  D  A  V  L  K  Q  I  P  Y  K    719

CCTCCTCGTACTGTCATCATGAAGGTGGGTAATAAAACAACGGCCCTCGATCCGGGGAGG   9600
 P  P  R  T  V  I  M  K  V  G  N  K  T  T  A  L  D  P  G  R    739

TACCAGTCCCGTCGAGGTCTCGTTGCAGTCAAGAGGGGTATTGCAGGCAATGAAGTTGAT   9660
 Y  Q  S  R  R  G  L  V  A  V  K  R  G  I  A  G  N  E  V  D    759

A
CTTTCTGATGGGGACTACCAAGTGGTGCCTCTTTTGCCGACTTGCAAAGACATAAACATG   9720
 L  S  D  G  D  Y  Q  V  V  P  L  L  P  T  C  K  D  I  N  M    779

GTGAAGGTGGCTTGCAATGTACTACTCAGCAAGTTCATAGTAGGGCCACCAGGTTCCGGA   9780
 V  K  V  A  C  N  V  L  L  S  K  F  I  V  G  P  P  G  S  G    799

T
AAGACCACCTGGCTACTGAGTCAAGTCCAGGACGATGATGTCATTTACACACCCACCCAT   9840
 K  T  T  W  L  L  S  Q  V  Q  D  D  D  V  I  Y  T  P  T  H    819
                                                  I

CAGACTATGTTTGATATAGTCAGTGCTCTCAAAGTTTGCAGGTATTCCATTCCAGGAGCC   9900
 Q  T  M  F  D  I  V  S  A  L  K  V  C  R  Y  S  I  P  G  A    839

TCAGGACTCCCTTTCCCACCACCTGCCAGGTCCGGGCCGTGGGTTAGGCTTATTGCCAGC   9960
 S  G  L  P  F  P  P  P  A  R  S  G  P  W  V  R  L  I  A  S    859

GGGCACGTCCCTGGCCGAGTATCATACCTCGATGAGGCTGGATATTGTAATCATCTGGAC  10020
 G  H  V  P  G  R  V  S  Y  L  D  E  A  G  Y  C  N  H  L  D    879

ATTCTTAGACTGCTTTCCAAAACACCCCTTGTGTGTTTGGGTGACCTTCAGCAACTTCAC  10080
 I  L  R  L  L  S  K  T  P  L  V  C  L  G  D  L  Q  Q  L  H    899

CCTGTCGGCTTTGATTCCTACTGTTATGTGTTCGATCAGATGCCTCAGAAGCAGCTGACC  10140
 P  V  G  F  D  S  Y  C  Y  V  F  D  Q  M  P  Q  K  Q  L  T    919

ACTATTTACAGATTTGGCCCTAACATCTGCGCACGCATCCAGCCTTGTTACAGGGAGAAA  10200
 T  I  Y  R  F  G  P  N  I  C  A  R  I  Q  P  C  Y  R  E  K    939

CTTGAATCTAAGGCTAGGAACACTAGGGTGGTTTTTACCACCCGGCCTGTGGCCTTTGGT  10260
 L  E  S  K  A  R  N  T  R  V  V  F  T  T  R  P  V  A  F  G    959

CAGGTGCTGACACCATACCATAAAGATCGCATCGGCTCTGCGATAACCATAGATTCATCC  10320
 Q  V  L  T  P  Y  H  K  D  R  I  G  S  A  I  T  I  D  S  S    979
```

FIG. 11

```
CAGGGGGCCACCTTTGATATTGTGACATTGCATCTACCATCGCCAAAGTCCCTAAATAAA  10380
 Q  G  A  T  F  D  I  V  T  L  H  L  P  S  P  K  S  L  N  K    999

TCCCGAGCACTTGTAGCCATCACTCGGGCAAGACACGGGTTGTTCATTTATGACCCTCAT  10440
 S  R  A  L  V  A  I  T  R  A  R  H  G  L  F  I  Y  D  P  H   1019

AACCAGCTCCAGGAGTTTTTCAACTTAACCCCTGAGCGCACTGATTGTAACCTTGTGTTC  10500
 N  Q  L  Q  E  F  F  N  L  T  P  E  R  T  D  C  N  L  V  F   1039

AGCCGTGGGGATGAGCTGGTAGTTCTGAATGCGGATAATGCAGTCACAACTGTAGCGAAG  10560
 S  R  G  D  E  L  V  V  L  N  A  D  N  A  V  T  T  V  A  K   1059

GCCCTTGAGACAGGTCCATCTCGATTTCGAGTATCAGACCCGAGGTGCAAGTCTCTCTTA  10620
 A  L  E  T  G  P  S  R  F  R  V  S  D  P  R  C  K  S  L  L   1079

GCCGCTTGTTCGGCCAGTCTGGAAGGGAGCTGTATGCCACTACCGCAAGTGGCACATAAC  10680
 A  A  C  S  A  S  L  E  G  S  C  M  P  L  P  Q  V  A  H  N   1099

CTGGGGTTTTACTTTTCCCCGGACAGTCCAACATTTGCACCTCTGCCAAAAGAGTTGGCG  10740
 L  G  F  Y  F  S  P  D  S  P  T  F  A  P  L  P  K  E  L  A   1119

CCACATTGGCCAGTGGTTACCCACCAGAATAATCGGGCGTGGCCTGATCGACTTGTCGCT  10800
 P  H  W  P  V  V  T  H  Q  N  N  R  A  W  P  D  R  L  V  A   1139

AGTATGCGCCCAATTGATGCCCGCTACAGCAAGCCAATGGTCGGTGCAGGGTATGTGGTC  10860
 S  M  R  P  I  D  A  R  Y  S  K  P  M  V  G  A  G  Y  V  V   1159

GGGCCGTCCACCTTTCTTGGTACTCCTGGTGTGGTGTCATACTATCTCACACTATACATC  10920
 G  P  S  T  F  L  G  T  P  G  V  V  S  Y  Y  L  T  L  Y  I   1179

AGGGGTGAGCCCCAGGCCTTGCCAGAAACACTCGTTTCAACAGGGCGTATAGCCACAGAT  10980
 R  G  E  P  Q  A  L  P  E  T  L  V  S  T  G  R  I  A  T  D   1199

TGTCGGGAGTATCTCGACGCGGCTGAGGAAGAGGCAGCAAAAGAACTCCCCCACGCATTC  11040
 C  R  E  Y  L  D  A  A  E  E  E  A  A  K  E  L  P  H  A  F   1219

ATTGGCGATGTCAAAGGTACCACGGTTGGGGGTGTCATCACATTACATCAAAATACCTA  11100
 I  G  D  V  K  G  T  T  V  G  G  C  H  H  I  T  S  K  Y  L   1239

CCTAGGTCCCTGCCTAAGGACTCTGTTGCCGTAGTTGGAGTAAGTTCGCCCGGCAGGGCT  11160
 P  R  S  L  P  K  D  S  V  A  V  V  G  V  S  S  P  G  R  A   1259

GCTAAAGCCGTGTGCACTCTCACCGATGTGTACCTCCCCGAACTCCGGCCATATCTGCAA  11220
 A  K  A  V  C  T  L  T  D  V  Y  L  P  E  L  R  P  Y  L  Q   1279

CCTGAGACGGCATCAAAATGCTGGAAACTCAAATTAGACTTCAGGGACGTCCGACTAATG  11280
 P  E  T  A  S  K  C  W  K  L  K  L  D  F  R  D  V  R  L  M   1299
```

FIG. 1m

```
GTCTGGAAAGGAGCCACCGCCTATTTCCAGTTGGAAGGGCTTACATGGTCGGCGCTGCCC  11340
 V  W  K  G  A  T  A  Y  F  Q  L  E  G  L  T  W  S  A  L  P   1319
              C
GACTATGCCAGGTTTATTCAGCTGCCCAAGGATGCCGTTGTATACATTGATCCGTGTATA  11400
 D  Y  A  R  F  I  Q  L  P  K  D  A  V  V  Y  I  D  P  C  I   1339

GGACCGGCAACAGCCAACCGTAAGGTCGTGCGAACCACAGACTGGCGGGCCGACCTGGCA  11460
 G  P  A  T  A  N  R  K  V  V  R  T  T  D  W  R  A  D  L  A   1359

GTGACACCGTATGATTACGGTGCCCAGAACATTTTGACAACAGCCTGGTTCGAGGACCTC  11520
 V  T  P  Y  D  Y  G  A  Q  N  I  L  T  T  A  W  F  E  D  L   1379

GGGCCGCAGTGGAAGATTTTGGGGTTGCAGCCCTTTAGGCGAGCATTTGGCTTTGAAAAC  11580
 G  P  Q  W  K  I  L  G  L  Q  P  F  R  R  A  F  G  F  E  N   1399

ACTGAGGATTGGGCAATCCTTGCACGCCGTATGAATGACGGCAAGGACTACACTGACTAT  11640
 T  E  D  W  A  I  L  A  R  R  M  N  D  G  K  D  Y  T  D  Y   1419

AACTGGAACTGTGTTCGAGAACGCCCACACGCCATCTACGGCGTGCTCGTGACCATACG   11700
 N  W  N  C  V  R  E  R  P  H  A  I  Y  G  R  A  R  D  H  T   1439

TATCATTTTGCCCCTGGCACAGAATTGCAGGTAGAGCTAGGTAAACCCCGGCTGCCGCCT  11760
 Y  H  F  A  P  G  T  E  L  Q  V  E  L  G  K  P  R  L  P  P   1459

GGGCAAGTGCCGTGAATTCGGGGTGATGCAATGGGGTCACTGTGGAGTAAAATCAGCCAG  11820
 G  Q  V  P  -                                                 1463
          ORF2          M  Q  W  G  H  C  G  V  K  S  A  S     12
                                    T
CTGTTCGTGGACGCCTTCACTGAGTTCCTTGTTAGTGTGGTTGATATTGCCATTTTCCTT  11880
  C  S  W  T  P  S  L  S  S  L  L  V  W  L  I  L  P  F  S  L    32
                                                    S
GCCATACTGTTTGGGTTCACCGTCGCAGGATGGTTACTGGTCTTTCTTCTCAGAGTGGTT  11940
   P  Y  C  L  G  S  P  S  Q  D  G  Y  W  S  F  F  S  E  W  F   52

TGCTCCGCGCTTCTCCGTTCGCGCTCTGCCATTCACTCTCCCGAACTATCGAAGGTCCTA  12000
   A  P  R  F  S  V  R  A  L  P  F  T  L  P  N  Y  R  R  S  Y   72

TGAAGGCTTGTTGCCCAACTGCAGACCGGATGTCCCACAATTTGCAGTCAAGCACCCATT  12060
    E  G  L  L  P  N  C  R  P  D  V  P  Q  F  A  V  K  H  P  L   92

C                                     G
GGGTATGTTTTGGCACATGCGAGTTTCCCACTTGATTGATGAGATGGTCTCTCGTCGCAT  12120
   G  M  F  W  H  M  R  V  S  H  L  I  D  E  M  V  S  R  R  I   112
                                          V
```

FIG. 1n

```
TTACCAGACCATGGAACATTCAGGTCAAGCGGCCTGGAAGCAGGTGGTTGGTGAGGCCAC    12180
  Y  Q  T  M  E  H  S  G  Q  A  A  W  K  Q  V  V  G  E  A  T     132

TCTCACGAAGCTGTCAGGGCTCGATATAGTTACTCATTTCCAACACCTGGCCGCAGTGGA    12240
  L  T  K  L  S  G  L  D  I  V  T  H  F  Q  H  L  A  A  V  E     152

GGCGGATTCTTGCCGCTTTCTCAGCTCACGACTCGTGATGCTAAAAAATCTTGCCGTTGG    12300
  A  D  S  C  R  F  L  S  S  R  L  V  M  L  K  N  L  A  V  G     172

CAATGTGAGCCTACAGTACAACACCACGTTGGACCGCGTTGAGCTCATCTTCCCCACGCC    12360
  N  V  S  L  Q  Y  N  T  T  L  D  R  V  E  L  I  F  P  T  P     192

AGGTACGAGGCCCAAGTTGACCGATTTCAGACAATGGCTCATCAGTGTGCACGCTTCCAT    12420
  G  T  R  P  K  L  T  D  F  R  Q  W  L  I  S  V  H  A  S  I     212
                                      ORF3  M  A  H  Q  C  A  R  F  H       9

TTTTTCCTCTGTGGCTTCATCTGTTACCTTGTTCATAGTGCTTTGGCTTCGAATTCCAGC    12480
  F  S  S  V  A  S  S  V  T  L  F  I  V  L  W  L  R  I  P  A     232
  F  F  L  C  G  F  I  C  Y  L  V  H  S  A  L  A  S  N  S  S      29

TCTACGCTATGTTTTTGGTTTCCATTGGCCCACGGCAACACATCATTCGAGCTGACCATC    12540
  L  R  Y  V  F  G  F  H  W  P  T  A  H  H  S  S  -              249
  S  T  L  C  F  W  F  P  L  A  H  G  N  T  S  F  E  L  T  I      49

AACTACACCATATGCATGCCCTGTTCTACCAGTCAAGCGGCTCGCCAAAGGCTCGAGCCC    12600
  N  Y  T  I  C  M  P  C  S  T  S  Q  A  A  R  Q  R  L  E  P      69

GGTCGTAACATGTGGTGCAAAATAGGGCATGACAGGTGTGAGGAGCGTGACCATGATGAG    12660
  G  R  N  M  W  C  K  I  G  H  D  R  C  E  E  R  D  H  D  E      89

TTGTTAATGTCCATCCCGTCCGGGTACGACAACCTCAAACTTGAGGGTTATTATGCTTGG    12720
  L  L  M  S  I  P  S  G  Y  D  N  L  K  L  E  G  Y  Y  A  W     109

CTGGCTTTTTTGTCCTTTTCCTACGCGGCCCAATTCCATCCGGAGTTGTTCGGGATAGGG    12780
  L  A  F  L  S  F  S  Y  A  A  Q  F  H  P  E  L  F  G  I  G     129

AATGTGTCGCGCGTCTTCGTGGACAAGCGACACCAGTTCATTTGTGCCGAGCATGATGGA    12840
  N  V  S  R  V  F  V  D  K  R  H  Q  F  I  C  A  E  H  D  G     149

CACAATTCAACCGTATCTACCGGACACAACATCTCCGCATTATATGCGGCATATTACCAC    12900
  H  N  S  T  V  S  T  G  H  N  I  S  A  L  Y  A  A  Y  Y  H     169

CACCAAATAGACGGGGGCAATTGGTTCCATTTGGAATGGCTGCGGCCACTCTTTTCTTCC    12960
  H  Q  I  D  G  G  N  W  F  H  L  E  W  L  R  P  L  F  S  S     189
                               ORF4  M  A  A  A  T  L  F  F        8
```

FIG. 1o

```
TGGCTGGTGCTCAACATATCATGGTTTCTGAGGCGTTCGCCTGTAAGCCCTGTTTCTCGA  13020
 W  L  V  L  N  I  S  W  F  L  R  R  S  P  V  S  P  V  S  R     209
  L  A  G  A  Q  H  I  M  V  S  E  A  F  A  C  K  P  C  F  S     28

CGCATCTATCAGATATTGAGACCAACACGACCGCGGCTGCCGGTTTCATGGTCCTTCAGG  13080
 R  I  Y  Q  I  L  R  P  T  R  P  R  L  P  V  S  W  S  F  R     229
  T  H  L  S  D  I  E  T  N  T  T  A  A  A  G  F  M  V  L  Q     48

ACATCAATTGTTTCCGACCTCACGGGGTCTCAGCAGCGCAAGAGAAAATTTCCTTCGGAA  13140
 T  S  I  V  S  D  L  T  G  S  Q  Q  R  K  R  K  F  P  S  E     249
  D  I  N  C  F  R  P  H  G  V  S  A  A  Q  E  K  I  S  F  G     68

AGTCGTCCCAATGTCGTGAAGCCGTCGGTACTCCCCAGTACATCACGATAACGGCTAACG  13200
 S  R  P  N  V  V  K  P  S  V  L  P  S  T  S  R  -              265
  K  S  S  Q  C  R  E  A  V  G  T  P  Q  Y  I  T  I  T  A  N     88

TGACCGACGAATCATACTTGTACAACGCGGACCTGCTGATGCTTTCTGCGTGCCTTTTCT  13260
                V  T  D  E  S  Y  L  Y  N  A  D  L  L  M  L  S  A  C  L  F   108

ACGCCTCAGAAATGAGCGAGAAAGGCTTCAAAGTCATCTTTGGGAATGTCTCTGGCGTTG  13320
 Y  A  S  E  M  S  E  K  G  F  K  V  I  F  G  N  V  S  G  V     128

TTTCTGCTTGTGTCAATTTCACAGATTATGTGGCCCATGTGACCCAACATACCCAGCAGC  13380
 V  S  A  C  V  N  F  T  D  Y  V  A  H  V  T  Q  H  T  Q  Q     148

ATCATCTGGTAATTGATCACATTCGGTTGCTGCATTTCCTGACACCATCTGCAATGAGGT  13440
 H  H  L  V  I  D  H  I  R  L  L  H  F  L  T  P  S  A  M  R     168

GGGCTACAACCATTGCTTGTTTGTTCGCCATTCTCTTGGCAATATGAGATGTTCTCACAA  13500
 W  A  T  T  I  A  C  L  F  A  I  L  L  A  I  -                 183
                                        ORF5    M  R  C  S  H  K   6

ATTGGGGCGTTTCTTGACTCCGCACTCTTGCTTCTGGTGGCTTTTTTTGCTGTGTACCGG  13560
    L  G  R  F  L  T  P  H  S  C  F  W  W  L  F  L  L  C  T  G   26

CTTGTCCTGGTCCTTTGCCGATGGCAACGGCGACAGCTCGACATACCAATACATATATAA  13620
    L  S  W  S  F  A  D  G  N  G  D  S  S  T  Y  Q  Y  I  Y  N   46

CTTGACGATATGCGAGCTGAATGGGACCGACTGGTTGTCCAGCCATTTTGGTTGGGCAGT  13680
    L  T  I  C  E  L  N  G  T  D  W  L  S  S  H  F  G  W  A  V   66

CGAGACCTTTGTGCTTTACCCGGTTGCCACTCATATCCTCTCACTGGGTTTTCTCACAAC  13740
    E  T  F  V  L  Y  P  V  A  T  H  I  L  S  L  G  F  L  T  T   86

AAGCCATTTTTTTGACGCGCTCGGTCTCGGCGCTGTATCCACTGCAGGATTTGTTGGCGG  13800
    S  H  F  F  D  A  L  G  L  G  A  V  S  T  A  G  F  V  G  G  106
```

FIG. 1p

```
GCGGTACGTACTCTGCAGCGTCTACGGCGCTTGTGCTTTCGCAGCGTTCGTATGTTTTGT   13860
  R  Y  V  L  C  S  V  Y  G  A  C  A  F  A  A  F  V  C  F  V     126

CATCCGTGCTGCTAAAAATTGCATGGCCTGCCGCTATGCCCGTACCCGGTTTACCAACTT   13920
  I  R  A  A  K  N  C  M  A  C  R  Y  A  R  T  R  F  T  N  F     146

CATTGTGGACGACCGGGGGAGAGTTCATCGATGGAAGTCTCCAATAGTGGTAGAAAAATT   13980
  I  V  D  D  R  G  R  V  H  R  W  K  S  P  I  V  V  E  K  L     166

GGGCAAAGCCGAAGTCGATGGCAACCTCGTCACCATCAAACATGTCGTCCTCGAAGGGGT   14040
  G  K  A  E  V  D  G  N  L  V  T  I  K  H  V  V  L  E  G  V     186

TAAAGCTCAACCCTTGACGAGGACTTCGGCTGAGCAATGGGAGGCCTAGACGATTTTTGC   14100
  K  A  Q  P  L  T  R  T  S  A  E  Q  W  E  A  -                 201
                                 ORF6       M  G  G  L  D  D  F  C    8

AACGATCCTATCGCCGCACAAAAGCTCGTGCTAGCCTTTAGCATCACATACACACCTATA   14160
  N  D  P  I  A  A  Q  K  L  V  L  A  F  S  I  T  Y  T  P  I     28

ATGATATACGCCCTTAAGGTGTCACGCGGCCGACTCCTGGGGCTGTTGCACATCCTAATA   14220
  M  I  Y  A  L  K  V  S  R  G  R  L  L  G  L  L  H  I  L  I     48

TTTCTGAACTGTTCCTTTACATTCGGATACATGACATATGTGCATTTTCAATCCACCAAC   14280
  F  L  N  C  S  F  T  F  G  Y  M  T  Y  V  H  F  Q  S  T  N     68

CGTGTCGCACTTACCCTGGGGGCTGTTGTCGCCCTTCTGTGGGGTGTTTACAGCTTCACA   14340
  R  V  A  L  T  L  G  A  V  V  A  L  L  W  G  V  Y  S  F  T     88

GAGTCATGGAAGTTTATCACTTCCAGATGCAGATTGTGTTGCCTTGGCCGGCGATACATT   14400
  E  S  W  K  F  I  T  S  R  C  R  L  C  C  L  G  R  R  Y  I     108

CTGGCCCCTGCCCATCACGTAGAAAGTGCTGCAGGTCTCCATTCAATCTCAGCGTCTGGT   14460
  L  A  P  A  H  H  V  E  S  A  A  G  L  H  S  I  S  A  S  G     128

AACCGAGCATACGCTGTGAGAAAGCCCGGACTAACATCAGTGAACGGCACTCTAGTACCA   14520
  N  R  A  Y  A  V  R  K  P  G  L  T  S  V  N  G  T  L  V  P     148

GGACTTCGGAGCCTCGTGCTGGGCGGCAAACGAGCTGTTAAACGAGGAGTGGTTAACCTC   14580
  G  L  R  S  L  V  L  G  G  K  R  A  V  K  R  G  V  V  N  L     168

GTCAAGTATGGCCGGTAAAAACCAGAGCCAGAAGAAAAAGAAAAGTACAGCTCCGATGGG   14640
  V  K  Y  G  R  -                                                173
  ORF7  M  A  G  K  N  Q  S  Q  K  K  K  S  T  A  P  M  G    18

GAATGGCCAGCCAGTCAATCAACTGTGCCAGTTGCTGGGTGCAATGATAAAGTCCCAGCG   14700
  N  G  Q  P  V  N  Q  L  C  Q  L  L  G  A  M  I  K  S  Q  R     38
```

FIG. 1q

```
                    T
CCAGCAACCTAGGGGAGGACAGGCCAAAAAGAAAAAGCCTGAGAAGCCACATTTTCCCCT   14760
 Q  Q  P  R  G  G  Q  A  K  K  K  K  P  E  K  P  H  F  P  L       58

GGCTGCTGAAGATGACATCCGGCACCACCTCACCCAGACTGAACGCTCCCTCTGCTTGCA   14820
 A  A  E  D  D  I  R  H  H  L  T  Q  T  E  R  S  L  C  L  Q       78

A
ATCGATCCAGACGGCTTTCAATCAAGGCGCAGGAACTGCGTCGCTTTCATCCAGCGGGAA   14880
 S  I  Q  T  A  F  N  Q  G  A  G  T  A  S  L  S  S  S  G  K       98

GGTCAGTTTTCAGGTTGAGTTTATGCTGCCGGTTGCTCATACAGTGCGCCTGATTCGCGT   14940
 V  S  F  Q  V  E  F  M  L  P  V  A  H  T  V  R  L  I  R  V      118

GACTTCTACATCCGCCAGTCAGGGTGCAAGTTAATTTGACAGTCAGGTGAATGGCCGCGA   15000
 T  S  T  S  A  S  Q  G  A  S  -                                 128

TGGCGTGTGGCCTCTGAGTCACCTATTCAATTAGGGCGATCACATGGGGGTCATACTTAA   15060

TTCAGGCAGGAACCATGTGACCGAAATTAAAAAAAAAAAAAAAAAAAAA              15088
```

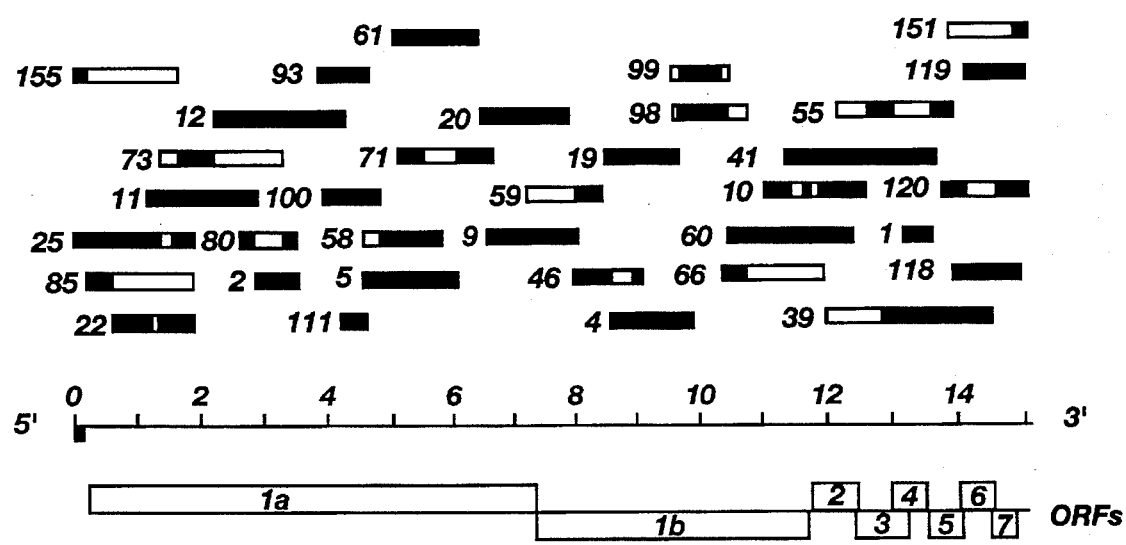
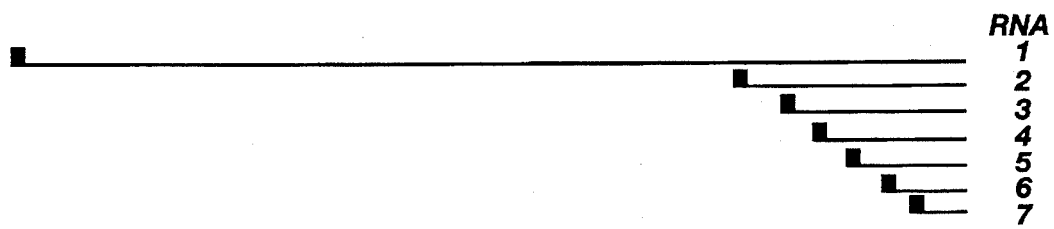
Fig. 2

CAUSATIVE AGENT OF THE MYSTERY SWINE DISEASE, VACCINE COMPOSITIONS AND DIAGNOSTIC KITS

FIELD OF THE INVENTION

The invention relates to the isolation, characterization and utilization of the causative agent of the Mystery Swine Disease (MSD). The invention utilizes the discovery of the agent causing the disease and the determination of its genome organization, the genomic nucleotide sequence and the proteins encoded by the genome, for providing protection against and diagnosis of infections, in particular protection against and diagnosis of MSD infections, and for providing vaccine compositions and diagnostic kits, either for use with MSD or with other pathogen-caused diseases.

BACKGROUND

In the winter and early spring of 1991, the Dutch pig industry was struck by a sudden outbreak of a new disease among breeding sows. Most sows showed anorexia, some aborted late in gestation (around day 110), showed stillbirths or gave birth to mummified fetuses and some had fever. Occasionally, sows with bluish ears were found, therefore the disease was commonly named "Abortus Blauw". The disease in the sows was often accompanied by respiratory distress and death of their young piglets, and often by respiratory disease and growth retardation of older piglets and fattening pigs.

The cause of this epizootic was not known, but the symptoms resembled those of a similar disease occurring in Germany since late 1990, and resembled those of the so-called "Mystery Swine Disease" as seen since 1987 in the mid-west of the United States of America and in Canada (Hill, 1990). Various other names have been used for the disease, in Germany it is known as "Seuchenhafter Sp ätabort der Schweine", and in North-America it is also known as "Mystery Pig Disease", "Mysterious Reproductive Syndrome", and "Swine Infertility and Respiratory Syndrome". In North-America, Loula (1990) described the general clinical signs as:

1) Off feed, sick animals of all ages
2) Abortions, stillbirths, weak pigs, mummies
3) Post farrowing respiratory problems
4) Breeding problems.

No causative agent has as yet been identified, but encephalomyocarditis virus (EMCV), porcine parvo virus (PPV), pseudorabies virus (PRV), swine influenza virus (SIV), bovine viral diarrhea virus (BVDV), hog cholera virus (HCV), porcine entero viruses (PEV), an influenza-like virus, chlamidiae, leptospirae, have all been named as possible cause (Loula, 1990; Mengeling and Lager, 1990; among others).

SUMMARY OF THE INVENTION

The invention provides a composition of matter comprising isolated Lelystad Agent which is the causative agent of Mystery Swine Disease, said Lelystad Agent essentially corresponding to the isolate Lelystad Agent (CDI-NL-2.91) deposited 5 Jun. 1991 with the Institut Pasteur, Collection Nationale de Cultures De Microorganismes (C.N.C.M.) 25, rue du Docteur Roux, 75724-Paris Cedex 15, France, deposit number I-1102. The words "essentially corresponding" refer to variations that occur in nature and to artificial variations of Lelystad Agent, particularly those which still allow detection by techniques like hybridization, PCR and ELISA, using Lelystad Agent-specific materials, such as Lelystad Agent-specific DNA or antibodies.

The composition of matter may comprise live, killed, or attenuated isolated Lelystad Agent; a recombinant vector derived from Lelystad Agent; an isolated part or component of Lelystad Agent; isolated or synthetic protein, (poly)peptide, or nucleic acid derived from Lelystad Agent; recombinant nucleic acid which comprises a nucleotide sequence derived from the genome of Lelystad Agent; a (poly)peptide having an amino acid sequence derived from a protein of Lelystad Agent, the (poly)peptide being produced by a cell capable of producing it due to genetic engineering with appropriate recombinant DNA; an isolated or synthetic antibody which specifically recognizes a part or component of Lelystad Agent; or a recombinant vector which contains nucleic acid comprising a nucleotide sequence coding for a protein or antigenic peptide derived from Lelystad Agent.

On the DNA level, the invention specifically provides a recombinant nucleic acid, more specifically recombinant DNA, which comprises a Lelystad Agent-specific nucleotide sequence shown in FIG. 1 which includes FIGS. 1a through 1q (SEQ ID NO: 1). Preferably, said Lelystad Agent-specific nucleotide sequence is selected from anyone of the ORFs (Open Reading Frames) shown in FIG. 1 (SEQ ID NO: 1).

On the peptide/protein level, the invention specifically provides a peptide comprising a Lelystad Agent-specific amino acid sequence shown in FIG. 1.

The invention further provides a vaccine composition for vaccinating animals, in particular mammals, more in particular pigs or swines, to protect them against Mystery Swine Disease, comprising Lelystad Agent, either live, killed, or attenuated; or a recombinant vector which contains nucleic acid comprising a nucleotide sequence coding for a protein or antigenic peptide derived from Lelystad Agent; an antigenic part or component of Lelystad Agent; a protein or antigenic polypeptide derived from, or a peptide mimicking an antigenic component of, Lelystad Agent; and a suitable carrier or adjuvant.

The invention also provides a vaccine composition for vaccinating animals, in particular mammals, more in particular pigs or swines, to protect them against a disease caused by a pathogen, comprising a recombinant vector derived from Lelystad Agent, the nucleic acid of the recombinant vector comprising a nucleotide sequence coding for a protein or antigenic peptide derived from the pathogen, and a suitable carrier or adjuvant.

The invention further provides a diagnostic kit for detecting nucleic acid from Lelystad Agent in a sample, in particular a biological sample such as blood or blood serum, sputum, saliva, or tissue, derived from an animal, in particular a mammal, more in particular a pig or swine, comprising a nucleic acid probe or primer which comprises a nucleotide sequence derived from the genome of Lelystad Agent, and suitable detection means of a nucleic acid detection assay.

The invention also provides a diagnostic kit for detecting antigen from Lelystad Agent in a sample, in particular a biological sample such as blood or blood serum, sputum, saliva, or tissue, derived from an animal, in particular a mammal, more in particular a pig or swine, comprising an antibody which specifically recognizes a part or component of Lelystad Agent, and suitable detection means of an antigen detection assay.

The invention also provides a diagnostic kit for detecting an antibody which specifically recognizes Lelystad Agent in a sample, in particular a biological sample such as blood or blood serum, sputum, saliva, or tissue, derived from an animal, in particular a mammal, more in particular a pig or swine, comprising Lelystad Agent; an antigenic part or component of Lelystad Agent; a protein or antigenic polypeptide derived from Lelystad Agent; or a peptide mimicking an antigenic component of Lelystad Agent; and suitable detection means of an antibody detection assay.

The invention also relates to a process for diagnosing whether an animal, in particular a mammal, more in particular a pig or swine, is contaminated with the causative agent of Mystery Swine Disease, comprising preparing a sample, in particular a biological sample such as blood or blood serum, sputum, saliva, or tissue, derived from the animal, and examining whether it contains Lelystad Agent nucleic acid, Lelystad Agent antigen, or antibody specifically recognizing Lelystad Agent, said Lelystad Agent being the causative agent of Mystery Swine Disease and essentially corresponding to the isolate Lelystad Agent (CDI-NL-2.91) deposited 5 Jun. 1991 with the Institut Pasteur, Paris, France, deposit number I-1102.

DETAILED DESCRIPTION OF THE INVENTION

Figure 3:
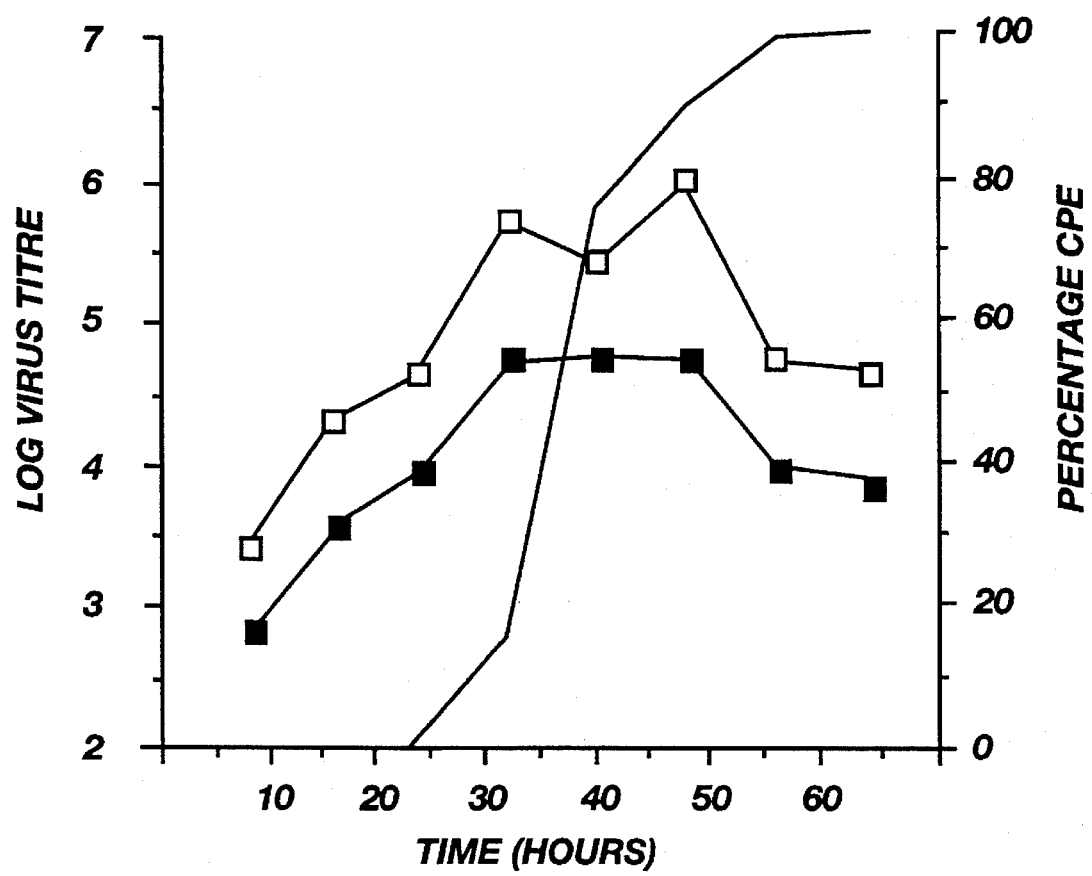

The invention is a result of combined efforts of the Central Veterinary Institute (CVI) and the Regional Animal Health Services (RAHS) in the Netherlands in trying to find the cause of the new disease MSD. Farms with pigs affected by the new disease were visited by field veterinarians of the RAHS. Sick pigs, specimens of sick pigs, and sow sera taken at the time of the acute and convalescent phase of the disease were sent for virus isolation to the RAHS and the CVI. Paired sera of affected sows were tested for antibodies against ten known pig-viruses. Three different viruses, encephalomyocarditis virus, porcine entero virus type 2, porcine entero virus type 7, and an unknown agent, Lelystad agent (LA), were isolated. Sows which had reportedly been struck with the disease mainly seroconverted to LA, and hardly to any of the other virus isolates or the known viral pathogens. In order to reproduce MSD experimentally, eight pregnant sows were inoculated intranasally with LA at day 84 of gestation. One sow gave birth to seven dead and four live but very weak piglets at day 109 of gestation; the four live piglets died one day after birth. Another sow gave birth at day 116 to three mummified fetuses, six dead piglets and three live piglets; two of the live piglets died within one day. A third sow gave birth at day 117 to two mummified fetuses, eight dead and seven live piglets. The other sows farrowed around day 115 and had less severe reproductive losses. The mean number of live piglets from all eight sows at birth was 7.3 and the mean number of dead piglets at birth was 4.6. Antibodies directed against LA were detected in 10 out of 42 serum samples collected before the pigs had sucked. LA was isolated from three piglets that died shortly after birth. These results justify the conclusion that LA is the causal agent of mystery swine disease.

LA grows with a cytopathic effect in pig lung macrophages and can be identified by staining in an immunoperoxidase-monolayer assay (IPMA) with postinfection sera of pigs c 829 and b 822, or with any of the other postinfection sera of the SPF pigs listed in table 5. Antibodies to LA can be identified by indirect staining procedures in IPMA. LA did not grow in any other cell system tested. LA was not neutralized by homologous sera, or by sera directed against a set of known viruses (Table 3). LA did not haemagglutinate with the red blood cells tested. LA is smaller than 200 nm since it passes through a filter with pores of this size. LA is sensitive to chloroform. The above results show that Lelystad agent is not yet identified as belonging to a certain virus group or other microbiological species. It has been deposited 5 Jun. 1991 under number I-1102 at Institute Pasteur, France.

The genome organization, nucleotide sequences, and polypeptides derived therefrom, of LA have now been found. These data together with those of others (see below) justify classification of LA (hereafter also called Lelystad Virus or LV) as a member of a new virus family, the Arteriviridae. As prototype virus of this new family we propose Equine Arteritis Virus (EAV), the first member of the new family of which data regarding the replication strategy of the genome and genome organization became available (de Vries et al., 1990, and references therein). On the basis of a comparison of our sequence data with those available for Lactate Dehydrogenase-Elevating Virus (LDV; Godeny et al., 1990), we propose that LDV is also a member of the Arteriviridae.

Given the genome organization and translation strategy of Arteriviridae it seems appropriate to place this new virus family into the superfamily of coronaviruses (Snijder et al., 1990a).

Arteriviruses have in common that their primary target cells in respective hosts are macrophages. Replication of LDV has been shown to be restricted to macrophages in its host, the mouse, whereas this strict propensity for macrophages has not been resolved yet for EAV, and LV.

Arteriviruses are spherical enveloped particles having a diameter of 45–60 nm and containing an icosahedral nucleocapsid (Brinton-Darnell and Plagemann, 1975; Horzinek et al., 1971; Hyllseth, 1973).

The genome of Arteriviridae consists of a positive stranded polyadenylated RNA molecule with a size of about 12–13 kilobases (kb) (Brinton-Darnell and Plageman, 1975; van der Zeijst et al., 1975). EAV replicates via a 3' nested set of six subgenomic mRNAs, ranging in size from 0.8 to 3.6 kb, which are composed of a leader sequence, derived from the 5' end of the genomic RNA, which is joined to the 3' terminal body sequences (de Vries et al., 1990).

Here we show that the genome organization and replication strategy of LV is similar to that of EAV, coronaviruses and toroviruses, whereas the genome sizes of the latter viruses are completely different from those of LV and EAV.

The genome of LV consists of a genomic RNA molecule of about 14.5 to 15.5 kb in length (estimated on a neutral agarose gel), which replicates via a 3' nested set of subgenomic RNAs. The subgenomic RNAs consist of a leader sequence, the length of which is yet unknown, which is derived from the 5' end of the genomic RNA and which is fused to the body sequences derived from the 3' end of the genomic RNA (FIG. 2).

The nucleotide sequence of the genomic RNA of LV was determined from overlapping cDNA clones. A consecutive sequence of 15,088 bp was obtained covering nearly the complete genome of LV (FIG. 1 (SEQ ID NO: 1)). In this sequence 8 open reading frames (ORFs) were identified: ORF 1A, ORF 1B, and ORFs 2 to 7.

ORF 1A and ORF 1B are predicted to encode the viral replicase or polymerase (SEQ ID NO: 2) and (SEQ ID NO: 3), whereas ORFs 2 to 6 are predicted to encode structural viral membrane (envelope) associated proteins (SEQ ID NOS: 4–8). ORF 7 is predicted to encode the structural viral nucleocapsid protein (SEQ ID NO: 9).

Because the products of ORF 6 and ORF 7 of LV (SEQ ID NO: 8) and (SEQ ID NO: 9) show a significant similarity with VpX and Vp1 of LDV respectively, it is predicted that the sequences of ORFs 6 and 7 will also be highly conserved among antigenic variants of LV.

The complete nucleotide sequence of FIG. 1 (SEQ ID NO: 1) and all the sequences and protein products encoded by ORFs 1 to 7 (SEQ ID NOS: 1–9) and possible other ORFs located in the sequence of FIG. 1 (SEQ ID NO: 1), are especially suited for vaccine development, in whatever sense, and for the development of diagnostic tools, in whatever sense. All possible modes are well known to persons skilled in the art.

Since it is now possible to unambiguously identify LA, the causal agent of MSD, it can now be tested whether pigs are infected with LA or not. Such diagnostic tests have until now not been available.

The test can be performed by virus isolation in macrophages, or other cell culture systems in which LA might grow, and staining the infected cultures with antibodies directed against LA (such as postinfection sera c 829 or b 822), but it is also feasible to develop and employ other types of diagnostic tests.

For instance, it is possible to use direct or indirect immunohistological staining techniques, i.e. with antibodies directed to LA that are labeled with fluorescent compounds such as isothiocyanate, or labeled with enzymes such as horseradish peroxidase. These techniques can be used to detect LA antigen in tissue sections or other samples from pigs suspected to have MSD. The antibodies needed for these tests can be c 829 or b 822 or other polyclonal antibodies directed against LA, but monoclonal antibodies directed against LA can also be used.

Furthermore, since the nature and organization of the genome of LA and the nucleotide sequence of this genome have been determined, LA specific nucleotide sequences can be identified and used to develop oligonucleotide sequences that can be used as probes or primers in diagnostic techniques such as hybridization, polymerase chain reaction, or any other techniques that are developed to specifically detect nucleotide acid sequences.

It is also possible to test for antibodies directed against LA. Table 5 shows that experimentally infected pigs rapidly develop antibodies against LA, and table 4 shows that pigs in the field also have strong antibody responses against LA. Thus it can now also be determined whether pigs have been infected with LA in the past. Such testing is of utmost importance in determining whether pigs or pig herds or pig populations or pigs in whole regions or countries are free of LA. The test can be done by using the IPMA as described, but it is also feasible to develop and employ other types of diagnostic tests for the detection of antibodies directed against LA.

LA specific proteins, polypeptides, and peptides, or peptide sequences mimicking antigenic components of LA, can be used in such tests. Such proteins can be derived from the LA itself, but it is also possible to make such proteins by recombinant DNA or peptide synthesis techniques. These tests can use specific polyclonal and/or monoclonal antibodies directed against LA or specific components of LA, and/or use cell systems infected with LA or cell systems expressing LA antigen. The antibodies can be used, for example, as a means for immobilizing the LA antigen (a solid surface is coated with the antibody whereafter the LA antigen is bound by the antibody) which leads to a higher specificity of the test, or can be used in a competitive assay (labeled antibody and unknown antibody in the sample compete for available LA antigen).

Furthermore, the above described diagnostic possibilities can be applied to test whether other animals, such as mammals, birds, insects or fish, or plants, or other living creatures, can be, or are, or have been infected with LA or related agents.

Since LA has now been identified as the causal agent of MSD, it is possible to make a vaccine to protect pigs against this disease. Such a vaccine can simply be made by growing LA in pig lung macrophage cultures, or in other cell systems in which LA grows. LA can then be purified or not, and killed by established techniques, such as inactivation with formaline or ultra-violet light. The inactivated LA can then be combined with adjuvantia, such as Freund's adjuvans or aluminum hydroxide or others, and this composition can then be injected in pigs.

Dead vaccines can also be made with LA protein preparations derived from LA infected cultures, or derived from cell systems expressing specifically LA protein through DNA recombinant techniques. Such subunits of LA would then be treated as above, and this would result in a subunit vaccine.

Vaccines using even smaller components of LA, such as polypeptides, peptides, or peptides mimicking antigenic components of LA are also feasible for use as dead vaccine.

Dead vaccines against MSD can also be made by recombinant DNA techniques through which the genome of LA, or parts thereof, is incorporated in vector systems such as vaccinia virus, herpesvirus, pseudorabies virus, adeno virus, baculo virus or other suitable vector systems that can so express LA antigen in appropriate cells systems. LA antigen from these systems can then be used to develop a vaccine as above, and pigs, vaccinated with such products would develop protective immune responses against LA.

Vaccines against MSD can also be based on live preparations of LA. Since only young piglets and pregnant sows seem to be seriously affected by infection with LA, it is possible to use unattenuated LA, grown in pig lung macrophages, as vaccine for older piglets, or breeding gilts. In this way sows can be protected against MSD before they get pregnant, which results in protection against abortions and stillbirth, and against congenital infections of piglets. Also the maternal antibody that these vaccinated sows give to their offspring would protect their offspring against the disease.

Attenuated vaccines (modified-live-vaccines) against MSD can be made by serially passaging LA in pig lung macrophages, in lung macrophages of other species, or in other cell systems, or in other animals, such as rabbits, until it has lost its pathogenicity.

Live vaccines against MSD can also be made by recombinant DNA techniques through which the genome of LA, or parts thereof, is incorporated in vector systems such as vaccinia virus, herpesvirus, pseudorabies virus, adeno virus or other suitable vector systems that can so express LA antigen. Pigs, vaccinated with such live vector systems would then develop protective immune responses against LA.

Lelystad agent itself would be specifically suited to use as a live vector system. Foreign genes could be inserted in the genome of LA and could be expressing the corresponding protein during the infection of the macrophages. This cell, which is an antigen presenting cell, would process the foreign antigen and present it to B-lymfocytes and T-lymfocytes which will respond with the appropriate immune respons.

Since LA seems to be very cell specific and possibly also very species specific, this vector system might be a very safe system, which does not harm other cells or species.

SHORT DESCRIPTION OF THE DRAWINGS

FIGS. 1a through 1g (SEQ ID NO: 1) shows the nucleotide sequence of the LV genome. The deduced amino acid sequence of the identified ORFs (SEQ ID NOS: 2–9) are shown. The methionines encoded by the (putative) ATG start sites are indicated in bold and putative N-glycosylation sites are underlined. Differences in the nucleotide and amino acid sequence, as identified by sequencing different cDNA clones, are shown. The nucleotide sequence of primer 25, which has been used in hybridization experiments (see FIG. 2 and section "results"), is underlined.

FIG. 2 shows the organization of the LV genome. The cDNA clones, which have been used for the determination of the nucleotide sequence, are indicated in the upper part of the figure. The parts of the clones, which were sequenced, are indicated in black. In the lower part of the figure the ORFs, identified in the nucleotide sequence, and the subgenomic set of mRNAs, encoding these ORFs, shown. The dashed lines in the ORFs represent alternative initiation sites (ATGs) of these ORFs. The leader sequence of the genomic and subgenomic RNAs is indicated by a solid box.

FIG. 3 shows the growth characteristics of LA:

empty squares—titre of cell-free virus;

solid squares—titre of cell-associated virus;

solid line—percentage cytopathic effect (CPE).

MATERIALS AND METHODS

Sample collection

Samples and pigs were collected from farms where a herd epizootic of MSD seemed to occur. Important criteria for selecting the farm as being affected with MSD were: sows that were off feed, the occurrence of stillbirth and abortion, weak offspring, respiratory disease and death among young piglets. Samples from four groups of pigs have been investigated:

(1) tissue samples and an oral swab from affected piglets from the field (table 1A), (2) blood samples and oral swabs from affected sows in the field (tables 1B and 4), (3) tissue samples, nasal swabs and blood samples collected from specific-pathogen-free (SPF) pigs experimentally infected by contact with affected sows from the field or (4) tissue samples, nasal swabs and blood samples collected from specific-pathogen-free (SPF) pigs experimentally infected by inoculation with blood samples of affected sows from the field (tables 2 and 5).

Sample preparation

Samples for virus isolation were obtained from piglets and sows which on clinical grounds were suspected to have MSD, and from experimentally infected SPF pigs, sows and their piglets.

Tissue samples were cut on a cryostat microtome and sections were submitted for direct immunofluorescence testing (IFT) with conjugates directed against various pig pathogens.

10% Suspensions of tissues samples were prepared in Hank's BSS supplemented with antibiotics, and oral and nasal swabs were soaked in Hank's BSS supplemented with antibiotics. After one hour at room temperature, the suspensions were clarified for 10 min at 6000 g, and the supernatant was stored at −70° C. for further use. Leucocyte fractions were isolated from EDTA or heparin blood as described earlier (Wensvoort and Terpstra, 1988), and stored at −70° C. Plasma and serum for virus isolation was stored at −70° C.

Serum for serology was obtained from sows suspected to be in the acute phase of MSD, a paired serum was taken 3–9 weeks later. Furthermore, sera were taken from the experimentally infected SPF pigs at regular intervals and colostrum and serum was taken from experimentally infected sows and their piglets. Sera for serology were stored at −20° C.

Cells

Pig lung macrophages were obtained from lungs of 5–6 weeks old SPF pigs or from lungs of adult SPF sows from the Central Veterinary Institute's own herd. The lungs were washed five to eight times with phosphate buffered saline (PBS). Each aliquot of washing fluid was collected and centrifuged for 10 min at 300 g. The resulting cell pellet was washed again in PBS and resuspended in cell culture medium (160 ml medium 199, supplemented with 20 ml 2.95% tryptose phosphate, 20 ml foetal bovine serum (FBS), and 4.5 ml 1.4% sodium bicarbonate) to a concentration of $4 \times 10^7$ cells/ml. The cell suspension was then slowly mixed with an equal volume of DMSO mix (6.7 ml of above medium, 1.3 ml FBS, 2 ml dimethylsulfoxide 97%), aliquoted in 2 ml ampoules and stored in liquid nitrogen.

Macrophages from one ampoule were prepared for cell culture by washing twice in Earle's MEM, and resuspended in 30 ml growth medium (Earle's MEM, supplemented with 10% FBS, 200 U/ml penicillin, 0.2 mg/ml streptomycine, 100 U/ml mycostatin, and 0.3 mg/ml glutamine). PK-15 cells (American Type Culture Collection, CCL33) and SK-6 cells (Kasza et al., 1972) were grown as described by Wensvoort et al. (1989). Secondary porcine kidney (PK2) cells were grown in Earle's MEM, supplemented with 10% FBS and the above antibiotics. All cells were grown in a cell culture cabinet at 37° C. and 5% $CO_2$.

Virus isolation procedures.

Virus isolation was performed according to established techniques using PK2, PK-15 and SK-6 cells, and pig lung macrophages. The former three cells were grown in 25 ml flasks (Greiner), and inoculated with the test sample when monolayers had reached 70–80% confluency. Macrophages were seeded in 100 µl aliquots in 96-well microtiter plates (Greiner) or in larger volumes in appropriate flasks, and inoculated with the test sample within one hour after seeding. The cultures were observed daily for cytopathic effects (CPE), and frozen at −70° C. when 50–70% CPE was reached or after five to ten days of culture. Further passages were made with freeze-thawed material of passage level 1 and 2 or higher. Some samples were also inoculated into nine to twelve day old embryonated hen eggs. Allantoic fluid was subinoculated two times using an incubation interval of three days and the harvest of the third passage was examined by haemagglutination at 4° C. using chicken red blood cells, and by an ELISA specifically detecting nucleoprotein of influenza A viruses (De Boer et al., 1990).

Serology

Sera were tested in haemagglutinating inhibition tests (HAI) to study the development of antibody against haemagglutinating encephalitis virus (HEV), and swine influenza viruses H1N1 and H3N2 according to the protocol of Masurel (1976). Starting dilutions of the sera in HAI were 1:9, after which the sera were diluted twofold.

Sera were tested in established enzyme-linked immunosorbent assays (ELISA) for antibodies against the glycoprotein gI of pseudorabies virus (PRV; Van Oirschot et al., 1988), porcine parvo virus (PPV; Westenbrink et al., 1986), bovine viral diarrhoea virus (BVDV; Westenbrink et al., 1986), and hog cholera virus (HCV; Wensvoort et al., 1988). Starting dilutions in the ELISA's were 1.5, after which the sera were diluted twofold.

Sera were tested for neutralizing antibodies against 30–300 TCID$_{50}$ of encephalomyocarditis viruses (EMCV), porcine enteroviruses (PEV), and Lelystad agent (LA) according to the protocol of Terpstra (1978). Starting dilutions of the sera in the serum neutralization tests (SNT) were 1:5, after which the sera were diluted twofold.

Sera were tested for binding with LA in an immunoperoxidase-monolayer assay (IPMA). Lelystad agent (LA; code: CDI-NL-2.91) was seeded in microtiter plates by adding 50 ml growth medium containing 100 TCID$_{50}$ LA to the wells of a microtiter plate containing freshly seeded lung macrophages. The cells were grown for two days and then fixed as described (Wensvoort, 1986). The test sera were diluted 1:10 in 0.15M NaCl, 0.05% Tween 80, 4% horse serum, or diluted further in fourfold steps, added to the wells and then incubated for one hour at 37° C. Sheep-anti-pig immunoglobulins (Ig) conjugated to horse radish peroxidase (HRPO, DAKO) were diluted in the same buffer and used in a second incubation for one hour at 37° C., after which the plates were stained as described (Wensvoort et al., 1986). An intense red staining of the cytoplasm of infected macrophages indicated binding of the sera to LA.

Virus identification procedures

The identity of cytopathic isolates was studied by determining the buoyant density in CsCl, by estimating particle size in negatively stained preparations through electron microscopy, by determining the sensitivity of the isolate to chloroform and by neutralizing the CPE of the isolate with sera with known specificity (Table 3). Whenever an isolate was specifically neutralized by a serum directed against a known virus, the isolate was considered to be a representative of this known virus.

Isolates that showed CPE on macrophage cultures were also studied by staining in IPMA with postinfection sera of pigs c 829 or b 822. The isolates were reinoculated on macrophage cultures and fixed at day 2 after inoculation before the isolate showed CPE. Whenever an isolate showed reactivity in IPMA with the postinfection sera of pigs c 829 or b 822, the isolate was considered to be a representative of the Lelystad agent. Representatives of the other isolates grown in macrophages or uninfected macrophages were also stained with these sera to check the specificity of the sera.

Further identification of Lelystad agent.

Lelystad agent was further studied by haemagglutination at 4° C. and 37° C. with chicken, guinea pig, pig, sheep, or human O red blood cells. SIV, subtype H3N2, was used as positive control in the haemagglutination studies.

The binding of pig antisera specifically directed against pseudorabies virus (PRV), transmissible gastroenteritis virus (TGE), porcine epidemic diarrhoea virus (PED), haemagglutinating encephalitis virus (HEV), African swine fever virus (ASFV), hog cholera virus (HCV) and swine influenza virus (SIV) type H1N1 and H3N2, of bovine antisera specifically directed against bovine herpes viruses type 1 and 4 (BHV 1 and 4), malignant catarrhal fever (MCF), parainfluenza virus 3 (PI3), bovine respiratory syncitial virus (BRSV) and bovine leukemia virus (BLV), and of avian antisera specifically directed against avian leukemia virus (ALV) and infectious bronchitis virus (IBV) was studied with species-Ig specific HRPO conjugates in an IPMA on LA infected and uninfected pig lung macrophages as described above.

We also tested in IPMA antisera of various species directed against mumps virus, Sendai virus, canine distemper virus, rinderpest virus, measles virus, pneumonia virus of mice, bovine respiratory syncytial virus, rabies virus, foamy virus, maedi-visna virus, bovine and murine leukemia virus, human, feline and simian immunodeficiency virus, lymphocytic choriomeningitis virus, feline infectious peritonitis virus, mouse hepatitis virus, Breda virus, Hantaan virus, Nairobi sheep disease virus, Eastern, Western and Venezuelan equine encephalomyelitis virus, rubella virus, equine arteritis virus, lactic dehydrogenase virus, yellow fever virus, tickborn encephalitis virus and hepatitis C virus.

LA was blindly passaged in PK2, PK-15, and SK-6 cells, and in embryonated hen eggs. After two passages, the material was inoculated again into pig lung macrophage cultures for reisolation of LA.

LA was titrated in pig lung macrophages prior to and after passing through a 0.2 micron filter (Schleicher and Schuell). The LA was detected in IPMA and by its CPE. Titres were calculated according to Reed and Muench (1938).

We further prepared pig antisera directed against LA. Two SPF pigs (21 and 23) were infected intranasally with $10^5$ TCID$_{50}$ of a fifth cell culture passage of LA. Two other SPF pigs (25 and 29) were infected intranasally with a fresh suspension of the lungs of an LA-infected SPF piglet containing $10^5$ TCID$_{50}$ LA. Blood samples were taken at 0, 14, 28, and 42 days postinfection (dpi).

We further grew LA in porcine alveolar macrophages to determine its growth pattern over time. Porcine alveolar macrophages were seeded in F25 flasks (Greiner), infected with LA with a multiplicity of infection of 0.01 TCID$_{50}$ per cell. At 8, 16, 24, 32, 40, 48, 56, and 64 h after infection, one flask was examined and the percentage of CPE in relation to a noninfected control culture was determined. The culture medium was then harvested and replaced with an equal volume of phosphate-buffered saline. The medium and the flask were stored at −70° C. After all cultures had been harvested, the LA titres were determined and expressed as log TCID$_{50}$ ml$^{-1}$.

The morphology of LA was studied by electronmicroscopy. LA was cultured as above. After 48 h, the cultures were freeze-thawed and centrifuged for 10 min at 6000× g. An amount of 30 ml supernatant was then mixed with 0.3 ml LA-specific pig serum and incubated for 1.5 h at 37° C. After centrifugation for 30 min at 125,000× g, the resulting pellet was suspended in 1% Seakem agarose ME in phosphate-buffered saline at 40° C. After coagulation, the agarose block was immersed in 0.8% glutaraldehyde and 0.8% osmiumtetroxide (Hirsch et al., 1968) in veronal/acetate buffer, pH 7.4 (230 mOsm/kg H$_2$O), and fixed by microwave irradiation. This procedure was repeated once with fresh fixative. The sample was washed with water, immersed in 1% uranyl acetate, and stained by microwave irradiation. Throughout all steps, the sample was kept at 0° C. and the microwave (Samsung RE211D) was set at defrost for 5 min. Thin sections were prepared with standard techniques, stained with lead citrate (Venable et al., 1965), and examined in a Philips CM 10 electron microscope.

We further continued isolating LA from sera of pigs originating from cases of MSD. Serum samples originated from the Netherlands (field case the Netherlands 2), Germany (field cases Germany 1 and Germany 2; courtesy Drs. Berner, München and Nienhoff, Münster), and the United States [experimental case United States 1 (experiment performed with ATCC VR-2332; courtesy Drs. Collins, St. Paul and Chladek, St. Joseph), and field cases United States 2 and United States 2; courtesy Drs. van Alstine, West Lafayette and Slife, Galesburg]. All samples were sent to the "Centraal Diergeneeskundig Instituut, Lelystad" for LA diagnosis. All samples were used for virus isolation on porcine alveolar macrophages as described. Cytophatic isolates were passaged three times and identified as LA by specific immunostaining with anti-LA post infection sera b 822 and c 829.

We also studied the antigenic relationships of isolates NL1 (the first LA isolate; code CDI-NL-2.91), NL2, GE1, GE2, US1, US2, and US3. The isolates were grown in macrophages as above and were tested in IPMA with a set of field sera and two sets of experimental sera. The sera were also tested in IPMA with uninfected macrophages.

The field sera were: Two sera positive for LV (TH-187 and TO-36) were selected from a set of LA-positive Dutch field sera. Twenty-two sera were selected from field sera sent from abroad to Lelystad for serological diagnosis. The sera originated from Germany (BE-352, BE-392 and NI-f2; courtesy Dr. Berner, München and Dr. Nienhoff, Münster), the United Kingdom (PA-141615, PA-141617 and PA-142440; courtesy Dr. Paton, Weybridge), Belgium (PE-1960; courtesy Prof. Pensaert, Gent), France (EA-2975 and EA-2985; courtesy Dr. Albina, Ploufragan), the United States (SL-441, SL-451, AL-RP9577, AL-P10814/33, AL-4994A, AL-7525, JC-MN41, JC-MN44 and JC-MN45; courtesy Dr. Slife, Galesburg, Dr. van Alstine, West Lafayette, and Dr. Collins, St. Paul), and Canada (RB-16, RB-19, RB-22 and RB-23; courtesy Dr. Robinson, Quebec).

The experimental sera were: The above described set of sera of pigs 21, 23, 25, and 29, taken at dpi 0, 14, 28, and 42. A set of experimental sera (obtained by courtesy of Drs. Chladek, St. Joseph, and Collins, St. Paul) that originated from four six-month-old gilts that were challenged intranasally with $10^{5.1}$ $TCID_{50}$ of the isolate ATCC VR-2332. Bloodsamples were taken from gilt 2B at 0, 20, 36, and 63 dpi; from gilt 9G at 0, 30, 44, and 68 dpi; from gilt 16W at 0, 25, 40, and 64 dpi; and from gilt 16Y at 0, 36, and 64 dpi.

To study by radio-immunoprecipitation assay (RIP; de Mazancourt et al., 1986) the proteins of LA in infected porcine alveolar macrophages, we grew LA-infected and uninfected macrophages for 16 hours in the presence of labeling medium containing $^{35}$S-Cysteine. Then the labeled cells were precipitated according to standard methods with 42 dpi post-infection sera of pig b 822 and pig 23 and with serum MN8 which was obtained 26 days after infecting a sow with the isolate ATCC VR-2332 (courtesy Dr. Collins, St. Paul). The precipitated proteins were analysed by electrophoresis in a 12% SDS-PAGE gel and visualized by fluorography.

To characterize the genome of LA, we extracted nuclear DNA and cytoplasmatic RNA from macrophage cultures that were infected with LA and grown for 24 h or were left uninfected. The cell culture medium was discarded, and the cells were washed twice with phosphate-buffered saline. DNA was extracted as described (Strauss, 1987). The cytoplasmic RNA was extracted as described (Favaloro et al., 1980), purified by centrifugation through a 5.7M CsCl cushion (Setzer et al., 1980), treated with RNase-free DNase (Pharmacia), and analyzed in an 0.8% neutral agarose gel (Moormann and Hulst, 1988).

Cloning and Sequencing

To clone LV RNA, intracellular RNA of LV-infected porcine lung alveolar macrophages (10 µg) was incubated with 10 mM methylmercury hydroxide for 10 minutes at room temperature. The denatured RNA was incubated at 42° C. with 50 mM Tris-HCl, pH 7.8, 10 mM $MgCl_2$, 70 mM KCl, 0.5 mM DATP, dCTP, dGTP and dTTP, 0.6 µg calf thymus oligonucleotide primers pd(N) 6 (Pharmacia) and 300 units of Moloney murine leukaemia virus reverse transcriptase (Bethesda Research Laboratories) in a total volume of 100 µl. 20 mM EDTA was added after 1 hr; the reaction mixture was then extracted with phenol/chloroform, passed through a Sephadex G50 column and precipitated with ethanol.

For synthesis of the second cDNA strand, DNA polymerase I (Boehringer) and RNase H (Pharmacia) were used (Gübler and Hoffman, 1983). To generate blunt ends at the termini, double-stranded cDNA was incubated with T4 DNA polymerase (Pharmacia) in a reaction mixture which contained 0.05 mM deoxynucleotide-triphosphates. Subsequently, cDNA was fractionated in a 0.8% neutral agarose gel (Moormann and Hulst, 1988). Fragments of 1 to 4 kb were electroeluted, ligated into the SmaI site of pGEM-4Z (Promega), and used for transformation of *Escherichia coli* strain DH5α (Hanahan, 1985). Colony filters were hybridized with a $^{32}$P-labelled single-stranded cDNA probe. The probe was reverse transcribed from LV RNA which had been fractionated in a neutral agarose gel (Moormann and Hulst, 1988). Before use the single stranded DNA probe was incubated with cytoplasmic RNA from mock-infected lung alveolar macrophages.

The relationship between LV cDNA clones was determined by restriction enzyme analysis and by hybridization of Southern blots of the digested DNA with nick-translated cDNA probes (Sambrook et al., 1989).

To obtain the 3' end of the viral genome, we constructed a second cDNA library, using oligo $(dT)_{12-18}$ and a 3' LV specific oligonucleotide that was complementary to the minus-strand viral genome as a primer in the first-strand reaction. The reaction conditions for first- and second-strand synthesis were identical to those described above. This library was screened with virus-specific 3' end oligonucleotide probes.

Most part (>95%) of the cDNA sequence was determined with an Automated Laser Fluorescent A.L.F.™ sequencer from Pharmacia LKB. Fluorescent oligonucleotide primer directed sequencing was performed on double-stranded DNA using the AutoRead™ Sequencing Kit (Pharmacia) essentially according to procedures C and D described in the Autoread™ Sequencing Kit protocol. Fluorescent primers were prepared with FluorePrime™ (Pharamacia). The remaining part of the sequence was determined via double-stranded DNA sequencing using oligonucleotide primers in conjunction with a T7 polymerase based sequencing kit (Pharmacia) and $\alpha$-$^{32}$S-dATP (Amersham). Sequence data were analysed using the sequence analysis programs PCGENE (Intelligenetics, Inc, Mountain View, USA) and FASTA (Pearson and Lipman, 1988).

Experimental reproduction of MSD.

Fourteen conventionally reared pregnant sows that were pregnant for 10–11 weeks were tested for antibody against LA in the IPMA. All were negative. Then two groups of four sows were formed and brought to the CVI. At week 12 of gestation, these sows were inoculated intranasally with 2 ml LA (passage level 3, titre $10^{4.8}$ $TCID_{50}$/ml). Serum and EDTA blood samples were taken at day 10 after inoculation. Food intake, rectal temperature, and other clinical symptoms were observed daily. At farrowing, the data of birth and the number of dead and living piglets per sow were recorded, and samples were taken for virus isolation and serology.

RESULTS

Immunofluorescence

Tissue sections of pigs with MSD were stained in an IFT with FITC-conjugates directed against African swine fever virus, hog cholera virus, pseudorabies virus, porcine parvo virus, porcine influenza virus, encephalomyocarditis virus and Chlamydia psittaci. The sections were stained, examined by fluorescent microscopy and all were found negative.

Virus isolation from piglets from MSD affected farms.

Cytopathic isolates were detected in macrophage cultures inoculated with tissue samples of MSD affected, two-to-ten day old piglets. Sixteen out of 19 piglets originating from five different farms were positive (Table 1A). These isolates all reacted in IPMA with the post-infection serum of pig c 829, whereas non-inoculated control cultures did not react. The isolates therefore were representatives of LA. One time a cytopathic isolate was detected in an SK-6 cell culture inoculated with a suspension of an oral swab from a piglet from a sixth farm (farm VE) (Table 1A). This isolate showed characteristics of the picorna viridae and was neutralized by serum specific for PEV 2, therefore the isolate was identified as PEV 2 (Table 3). PK2, PK-15 cells and hen eggs inoculated with samples from this group remained negative throughout.

Virus isolation from sows from MSD affected farms.

Cytopathic isolates were detected in macrophage cultures inoculated with samples of MSD affected sows. 41 out of 63 sows originating from 11 farms were positive (Table 1B). These isolates all reacted in IPMA with the post-infection serum of pig b 822 and were therefore representatives of LA. On one occasion a cytopathic isolate was detected in a PK2 cell culture inoculated with a suspension of a leucocyte fraction of a sow from farm HU (Table 1B). This isolate showed characteristics of the picorna viridae and was neutralized by serum specific for EMCV, therefore the isolate was identified as EMCV (Table 3). SK-6, PK-15 cells and hen eggs inoculated with samples from this group remained negative.

Virus isolation from SPF pigs kept in contact with MSD affected sows.

Cytopathic isolated were detected in macrophage cultures inoculated with samples of SPF pigs kept in contact with MSD affected sows. Four of the 12 pigs were positive (Table 2). These isolates all reacted in IPMA with the post-infection serum of pig c 829 and of pig b 822 and were therefore representatives of LA. Cytopathic isolates were also detected in Pk2, PK-15 and SK-6 cell cultures inoculated with samples of these isolates were all neutralized by serum directed against PEV 7. One of these seven isolates was studied further and other characteristics also identified the isolate as PEV 7 (Table 3).

Virus isolation from SPF pigs inoculated with blood of MSD affected sows.

Cytopathic isolates were detected in macrophage cultures inoculated with samples of SPF pigs inoculated with blood of MSD affected sows. Two out of the eight pigs were positive (Table 2). These isolates all reacted in IPMA with the post-infection serum of pig c 829 and of pig b 822 and were therefore representatives of LA. PK2, SK-6 and PK-15 cells inoculated with samples from this group remained negative.

Summarizing, four groups of pigs were tested for the presence of agents that could be associated with mystery swine disease (MSD).

In group one, MSD affected piglets, the Lelystad agent (LA) was isolated from 16 out of 20 piglets; one time PEV 2 was isolated.

In group two, MSD affected sows, the Lelystad agent was isolated from 41 out of 63 sows; one time EMCV was isolated. Furthermore, 123 out of 165 MSD affected sows seroconverted to the Lelystad agent, as tested in the IPMA. Such massive seroconversion was not demonstrated against any of the other viral pathogens tested.

In group three, SPF pigs inoculated with blood of MSD affected sows, the LA was isolated from two pigs. All eight pigs seroconverted to LA.

Serology of sows from MSD affected farms.

Paired sera from sows affected with MSD were tested against a variety of viral pathogens and against the isolates obtained during this study (Table 4). An overwhelming antibody response directed against LA was measured in the IPMA (75% of the sows seroconverted, in 23 out of the 26 farms seroconversion was found), whereas with none of the other viral pathogens a clear pattern of seroconversion was found. Neutralizing antibody directed against LA was out detected. Serology of SPF pigs kept in contact with MSD affected sows.

All eight SPF pigs showed an antibody response in the IPMA against LA (Table 5). None of these sera were positive in the IPMA performed on uninfected macrophages. None of these sera were positive in the SNT of LA. The sera taken two weeks after contact had all high neutralizing antibody titres (>1280) against PEV 7, whereas the pre-infection sera were negative (>10), indicating that all pigs had also been infected with PEV 7.

Serology of SPF pigs inoculated with blood of MSD affected sows.

All eight SPF pigs showed an antibody response in the IPMA against LA (Table 5). None of these sera were positive in the IPMA performed on uninfected macrophages. None of these sera were positive in the SNT for LA. The pre- and two weeks post-inoculation sera were negative (<10) against PEV 7.

Further identification of Lelystad agent.

LA did not haemagglutinate with chicken, guinea pig, pig, sheep, or human O red blood cells.

LA did not react in IPMA with sera directed against PRV, TGE, PED, ASFV, etc.

After two blind passages, LA did not grow in PK2, PK-15, or SK-6 cells, or in embryonated hen eggs, inoculated through the allantoic route.

LA was still infectious after it was filtered through a 0.2 micro filter, titres before and after filtration were $10^{5.05}$ and $10^{5.3}$ TCID$_{50}$ as detected by IPMA.

Growth curve of LA (see FIG. 3). Maximum titres of cell-free virus were approximately $10^{5.5}$ TCID$_{50}$ ml$^{-1}$ from 34–48 h after inoculation. After that time the macrophages were killed by the cytopathic effect of LA.

Electronmicroscopy. Clusters of spherical LA particles were found. The particles measured 45–55 nm in diameter and contained a 30–35 nm nucleocapsid that was surrounded by a lipid bilayer membrane. LA particles were not found in infected cultures that were treated with negative serum or in negative control preparations.

Isolates from the Netherlands, Germany, and the United States. All seven isolates were isolated in porcine alveolar macrophages and passaged three to five times. All isolates caused a cytopathic effect in macrophage and could be specifically immunostained with anti-LA sera b 822 and the 42 dpi serum 23. The isolates were named NL2, GE1, GE2, US1, US2, and US3.

Antigenic relationships of isolates NL1, NL2, GE1, GE2, US1, US2, and US3. None of the field sera reacted in IPMA with uninfected macrophages but all sera contained antibodies directed against one or more of the seven isolates (Table 7). None of the experimental sera reacted in IPMA with uninfected macrophages, and none of the 0 dpi experimental sera reacted with any of the seven isolates in IPMA (Table 8). All seven LA isolates reacted with all or most of the sera from the set of experimental sera of pigs 21, 23, 25, and 29, taken after 0 dpi. Only the isolates US1, US2, and US3 reacted with all or most of the sera from the set of experimental sera of gilts 2B, 9G, 16W, and 16Y, taken after 0 dpi.

Radioimmunoprecipitation studies. Seven LA-specific proteins were detected in LA-infected macrophages but not in uninfected macrophages precipitated with the 42 dpi sera of pigs b 822 and 23. The proteins had estimated molecular weights of 65, 39, 35, 26, 19, 16, and 15 kilodalton. Only two of these LA-specific proteins, of 16 and 15 kilodalton, were also precipitated by the 26 dpi serum MN8.

Sequence and oraganization of the genome of LV

The nature of the genome of LV was determined by analyzing DNA and RNA from infected porcine lung alveolar macrophages. No LV-specific DNA was detected. However, we did detect LV-specific RNA. In a 0.8% neutral agarose gel LV RNA migrated slightly slower than a preparation of hog cholera virus RNA of 12.3 kb (Moormann et al., 1990) did. Although no accurate size determination can be performed in neutral agarose gels, it was estimated that the LV-specific RNA is about 14.5 to 15.5 kb in length.

To determine the complexity of the LV-specific RNAs in infected cells and to establish the nucleotide sequence of the genome of LV, we prepared cDNA from RNA of LV-infected porcine lung alveolar macrophages and selected and mapped LV-specific cDNA clones as described under Materials and Methods. The specificity of the cDNA clones was reconfirmed by hybridizing specific clones, located throughout the overlapping cDNA sequence, to Northern blots carrying RNA of LV-infected and uninfected macrophages. Remarkably, some of the cDNA clones hybridized with the 14.5 to 15.5 kb RNA detected in infected macrophages only, whereas others hybridized with the 14.5 to 15.5 kb RNA as well as with a panel of 4 or 5 RNAs of lower molecular weight (estimated size, 1 to 4 kb). The latter clones were all clustered at one end of the cDNA map and covered about 4 kb of DNA. These data suggested that the genome organization of LV may be similar to that of coronaviridae (Spaan et al., 1988), Berne virus (BEV; Snijder et al., 1990b), a torovirus, and EAV (de Vries et al., 1990), i.e. besides a genomic RNA there are subgenomic mRNAs which form a nested set which is located at the 3' end of the genome. This assumption was confirmed when sequences of the cDNA clones became available and specific primers could be selected to probe the blots with. A compilation of the hybridization data obtained with cDNA clones and specific primers, which were hybridized to Northern blots carrying the RNA of LV-infected and uninfected macrophages, is shown in FIG. 2. Clones 12 and 20 which are located in the 5' part and the centre of the sequence respectively hybridize to the 14.5 to 15.5 kb genomic RNA detected in LV-infected cells only. Clones 41 and 39, however, recognize the 14.5 to 15.5 kb genomic RNA and a set of 4 and 5 RNAs of lower molecular weight, respectively. The most instructive and conclusive hybridization pattern, however, was obtained with primer 25, which is located at the ultimate 5' end in the LV sequence (compare FIG. 1). Primer 25 hybridized to a panel of 7 RNAs, with an estimated molecular weight ranging in size from 0.7 to 3.3 kb (subgenomic mRNAs), as well as the genomic RNA. The most likely explanation for the hybridization pattern of primer 25 is that 5' end genomic sequences, the length of which is yet unknown, fuse with the body of the mRNAs which are transcribed from the 3' end of the genome. In fact, the hybridization pattern obtained with primer 25 suggests that 5' end genomic sequences function as a so called "leader sequence" in subgenomic mRNAs. Such a transcription pattern is a hallmark of replication of coronaviridae (Spaan et al., 1988), and of EAV (de Vries et al., 1990).

The only remarkable discrepancy between LV and EAV which could be extracted from the above data is that the genome size of LV is about 2.5 kb larger than that of EAV.

The consensus nucleotide sequence of overlapping cDNA clones is shown in FIG. 1 (SEQ ID NO: 1). The length of the sequence is 15,088 basepairs, which is in good agreement with the estimated size of the genomic LV RNA.

Since the LV cDNA library was made by random priming of the reverse transcriptase reaction with calf thymus pd(N) 6 primers, no cDNA clones were obtained which started with a poly-A stretch at their 3' end. To clone the 3' end of the viral genome, we constructed a second cDNA library, using oligo (dT) and primer 39U183R in the reverse transcriptase reaction. Primer 39U183R is complementary to LV minus-strand RNA, which is likely present in a preparation of RNA isolated from LV-infected cells. This library was screened with virus-specific probes (nick-translated cDNA clone 119 and oligonucleotide 119R64R), resulting in the isolation of five additional cDNA clones (e.g., cDNA clone 151, FIG. 2). Sequencing of these cDNA clones revealed that LV contains a 3' poly(A) tail. The length of the poly(A) tail varied between the various cDNA clones, but its maximum length was twenty nucleotides. Besides clone 25 and 155 (FIG. 2), four additional cDNA clones were isolated at the 5' end of the genome, which were only two to three nucleotides shorter than the ultimate 5' nucleotide shown in FIG. 1 (SEQ ID NO: 1). Given this finding and given the way cDNA was synthesized, we assume to be very close to the 5' end of the sequence of LV genomic RNA.

Nearly 75% of the genomic sequence of LV encodes ORF 1A and ORF 1A probably initiates at the first AUG (nucleotide position 212, FIG. 1) encountered in the LV sequence. The C-terminus of ORF 1A overlaps the putative N-terminus of ORF 1B over a small distance of 16 nucleotides. It thus seems that translation of ORF 1B proceeds via ribosomal frameshifting, a hallmark of the mode of translation of the polymerase or replicase gene of coronaviruses (Boursnell et al. 1987; Bredenbeek et al. 1990) and the torovirus BEV (Snijder et al., 1990a). The characteristic RNA pseudoknot structure which is predicted to be formed at the site of the ribosomal frameshifting is also found at this location in the sequence of LV (results not shown).

ORF 1B encodes an amino acid sequence (SEQ ID NO: 3) or nearly 1400 residues which is much smaller than ORF 1B of the coronaviruses MHV and IBV (about 3,700 amino acid residues; Bredenbeek et al., 1990; Boursnell et al., 1987) and BEV (about 2,300 amino acid residues; Snijder et al., 1990a). Characteristic features of the ORF 1B product (SEQ ID NO: 3) or members of the superfamily of coronaviridae like the replicase motif and the Zinc finger domain can also be found in ORF 1B of LV (results not shown).

Whereas ORF 1A and ORF 1B encode the viral polymerase (SEQ ID NO: 2) and (SEQ ID NO: 3) and therefore are considered to encode a non-structural viral protein, ORFs 2 to 7 are believed to encoded structural viral proteins (SEQ ID NOS: 4–9).

The products of ORFs 2 to 6 (SEQ ID NOS: 4–8) all show features reminiscent of membrane (envelope) associated proteins. ORF 2 encodes a protein (SEQ ID NO: 4) of 249 amino acids containing two predicted N-linked glycosylation sites (Table 9). At the N-terminus a hydrophobic sequence, which may function as a so called signal sequence, is identified. The C-terminus also ends with a hydrophobic sequence which in this case may function as a transmembrane region which anchors the ORF 2 product (SEQ ID NO: 4) in the viral envelope membrane.

ORF 3 may initiate at the AUG starting at nucleotide position 12394 or at the AUG starting at nucleotide position 12556 and then encodes proteins (SEQ ID NO: 5) of 265 and 211 amino acids respectively. The protein of 265 residues contains seven putative N-linked glycosylation sites, whereas the protein of 211 residues contains four (Table 9). At the N-terminus of the protein (SEQ ID NO: 5) of 265 residues a hydrophobic sequence is identified.

Judged by hydrophobicity analysis, the topology of the protein encoded by ORF 4 (SEQ ID NO: 6) is similar to that encoded by ORF 2 (SEQ ID NO: 4) if the product of ORF 4 (SEQ ID NO: 6) initiates at the AUG starting at nucleotide position 12936. However, ORF 4 may also initiate at two other AUG codons (compare FIGS. 1 and 2) starting at positions 12981 and 13068 in the sequence respectively. Up to now it is unclear which startcodon is used. Depending on the startcodon used, ORF 4 may encode proteins (SEQ ID NO: 6) of 183 amino acids containing four putative N-linked glycosylation sites, of 168 amino acids containing four putative N-linked glycosylation sites, or of 139 amino acids containing three putative N-linked glycosylation sites (Tables 9).

ORF 5 is predicted to encode a protein (SEQ ID NO: 7) of 201 amino acids having two putative N-linked glycosylation sites (Table 9). A characteristic feature of the ORF 5 product (SEQ ID NO: 7) is the internal hydrophobic sequence between amino acid 108 to amino acid 132.

Analysis for membrane spanning segments and hydrophilicity of the product of ORF 6 (SEQ ID NO: 8) shows that it contains three transmembrane spanning segments in the N-terminal 90 amino acids of its sequence. This remarkable feature is also a characteristic of the small envelope glycoprotein M or E1 of several coronaviruses e.g. Infectious Bronchitis Virus (IBV; Boursnell et al., 1984) and Mouse Hepatitis Virus (MHV; Rottier et al., 1986). It is therefore predicted that the protein encoded by ORF 6 (SEQ ID NO: 8) has a membrane topology analogous to that of the M of E1 protein of coronaviruses (Rottier et al., 1986). A second characteristic of the M or E1 protein is a so called surface helix which is located immediately adjacent to the presumed third transmembrane region. This sequence of about 25 amino acids which is very well conserved among coronaviruses is also recognized, although much more degenerate, in LV. Yet we predict the product of LV ORF 6 (SEQ ID NO: 8) to have an analogous membrane associated function as the coronavirus M or E1 protein. Furthermore, the protein encoded by ORF (SEQ ID NO: 8) showed a strong similarity (53% identical amino acids) with VpX (Godeny et al., 1990) of LDV.

The protein encoded by ORF 7 (SEQ ID NO: 9) has a length of 128 amino acid residues (Table 9) which is 13 amino acids longer than Vp1 of LDV (Godeny et al., 1990). Yet a significant similarity (43% identical amino acids) was observed between the protein encoded by ORF 7 (SEQ ID NO: 9) and Vp1. Another shared characteristic between the product of ORF 7 and Vp1 is the high concentration of basis residues (Arg, Lys and His) in the N-terminal half of the protein. Up to amino acid 55 the LV sequence contains 26% Arg, Lys and His. This finding is fully in line with the proposed function of the ORF 7 product (SEQ ID NO: 9) or Vp1 (Godeny et al., 1990), namely encapsidation of the viral genomic RNA. On the basis of above data, we propose the LV ORF 7 product (SEQ ID NO: 9) to be the nucleocapsid protein N of the virus.

A schematic representation of the organization of the LV genome is shown in FIG. 2. The map of overlapping clones used to determine the sequence of LV is shown in the top panel. A linear compilation of this map indicating the 5' and 3' end of the nucleotide sequence of LV, shown in FIG. 1 (SEQ ID NO: 1), including a division in kilobases is shown below the map of cDNA clones and allows the positioning of these clones in the sequence. The position of the ORFs identified in the LV genome is indicated below the linear map of the LV sequence. The bottom panel shows the nested set of subgenomic mRNAs and the position of these RNAs relative to the LV sequence.

In line with the translation strategy of coronavirus, torovirus and arterivirus subgenomic mRNAs it is predicted that ORFs 1 to 6 are translated from the unique 5' end of their genomic or mRNAs. This unique part of the mRNAs is considered to be that part of the RNA that is obtained when a lower molecular weight RNA is "subtracted" from the higher molecular weight RNA which is next in line. Although RNA 7 forms the 3' end of all the other genomic and subgenomic RNAs, and thus does not have a unique region, it is believed that ORF 7 is only translated from this smallest sized mRNA. The "leader sequence" at the 5' end of the subgenomic RNAs is indicated with a solid box. The length of this sequence is about 200 bases, but the precise site of fusion with the body of the genomic RNAs still has to be determined.

Experimental reproduction of MSD

Eight pregnant sows were inoculated with LA and clinical signs of MSD such as inappetance and reproductive losses were reproduced in these sows. From day four to day 10–12 post-inoculation (p.i.), all sows showed a reluctance to eat. None of the sows had elevated body temperatures. Two sows had bluish ears at day 9 and 10 p.i. In Table 6 the day of birth and the number of living and dead piglets per sow is given. LA was isolated from 13 of the born piglets.

TABLE 1

Description and results of virus isolation of field samples.

A Samples of piglets suspected of infection with MSD.

| farm | number of pigs | age days | material used | results* |
| --- | --- | --- | --- | --- |
| RB | 5 | 2 | lung, tonsil, and brains | 5 × LA |
| DV | 4 | 3 | lung, brains, pools of kidney, spleen | 3 × LA |
| TH | 3 | 3–5 | lung, pools of kidney, tonsil | 3 × LA |
| DO | 3 | 10 | lung, tonsil | 2 × LA |
| ZA | 4 | 1 | lung, tonsil | 3 × LA |
| VE | 1 | ? | oral swab | 1 × PEV 2 |
| TOTAL | 20 | | | 16 × LA, 1 × PEV 2 |

B Samples of sows suspected of infection with MSD.

| farm | number of sows | material used | results |
| --- | --- | --- | --- |
| TH | 2 | plasma and leucocytes | 1 × LA |
| HU | 5 | plasma and leucocytes | 2 × LA, 1 × EMCV |
| TS | 10 | plasma and leucocytes | 6 × LA |
| HK | 5 | plasma and leucocytes | 2 × LA |
| LA | 6 | plasma and leucocytes | 2 × LA |
| VL | 6 | serum and leucocytes | 5 × LA |
| TA | 15 | serum | 11 × LA |
| LO | 4 | plasma and leucocytes | 2 × LA |
| JA | 8 | plasma and leucocytes | 8 × LA |
| VD | 1 | plasma and leucocytes | 1 × LA |
| VW | 1 | serum | 1 × LA |
| TOTAL | 63 | | 41 × LA, 1 × EMCV |

*Results are given as the number of pigs from which the isolation was made. Sometimes the isolate was detected in more then one sample per pig.
LA = Lelystad agent
PEV 2 = porcine entero virus type 2
EMCV = encephalomyocarditis virus

TABLE 2

Description and results of virus isolation of samples of pigs with experimentally induced infections.

| sow | pig@ | material used | results* |
|---|---|---|---|
| A (LO) # | c 835 | lung, tonsil | 2 × LA |
|  | c 836 | nasal swabs | 2 × PEV 7 |
|  | c 837 | nasal swabs |  |
| B (JA) | c 825 | lung, tonsil |  |
|  | c 821 | nasal swabs | 1 × PEV 7 |
|  | c 823 | nasal swabs | 4 × PEV 7 |
| C (JA) | c 833 | lung tonsil | 1 × LA, 1 × PEV 7 |
|  | c 832 | nasal swabs | 2 × PEV 7 |
|  | c 829 | nasal swabs, plasma and leucocytes | 3 × LA, 2 × PEV 7 |
| D (VD) | c 816 | lung, tonsil |  |
|  | c 813 | nasal swabs | 1 × LA |
|  | c 815 | nasal swabs | 1 × PEV 7 |
| TOTAL isolates from contact pigs | | | 7 × LA, 13 × PEV 7 |
| A | b 809 | nasal swabs |  |
|  | b 817 | nasal swabs |  |
| B | b 818 | nasal swabs, plasma and leucocytes | 1 × LA |
|  | b 820 | nasal swabs |  |
| C | b 822 | nasal swabs |  |
|  | b 826 | nasal swabs |  |
| D | b 830 | nasal swabs | 1 × LA |
|  | b 834 | nasal swabs |  |
| TOTAL isolates from blood inoculated pigs | | | 2 × LA |

@ SPF pigs were either kept in contact (c) with a sow suspected to be infected with MSD, or were given 10 ml EDTA blood (b) of that sow intramuscularly at day 0 of the experiment. Groups of one sow and three SPF pigs (c) were kept in one pen, and all four of these groups were housed in one stable. At day 6, one SPF pig in each group was killed and tonsil and lungs were used for virus isolation. The four groups of SPF pigs inoculated with blood (b) were housed in four other pens in a separate stable. Nasal swabs of the SPF pigs were taken at day 2, 5, 7 and 9 of the experiment, and EDTA blood for virus isolation from plasma and leucocytes was taken whenever a pig had fever.
*Results are given as number of isolates per pig.
LA = Lelystad agent
PEV 7 = porcine entero virus type 7
In brackets the initials of the farm of origin of the sow are given.

TABLE 3

Identification of viral isolates

| origin and cell culture | buoyant[1] density in CsCl | particle[2] size in FM (nm) | sens[3]. to chloroform | neutralized by[4] serum directed against (titre) |
|---|---|---|---|---|
| leucocytes sow farm HU PK15, PK2, SK6 | 1.33 g/ml | 28–30 | not sens. | EMCV ( 1280) |
| oral swab piglet farm VE SK6 | ND | 28–30 | not sens. | PEV 2 (>1280) |
| nasal swabs, tonsil SPF pigs CVI PK-15, PK2, SK6 | ND | 28–30 | not sens. | PEV 7 (>1280) |
| various samples various farms pig lung macrophages | 1.19 g/ml | pleomorf | sens. | none (all <5) |

[1]Buoyant density in preformed lineair gradients of CsCl in PBS was determined according to standard techniques (Brakke; 1967). Given is the density where the peak of infectivity was found.
[2]Infected and noninfected cell cultures of the isolate under study were freeze-thawed. Cell lysates were centrifuged for 30 min at 130,000 g, the resulting pellet was negatively stained according to standard techniques (Brenner and Horne; 1959), and studied with a Philips CM 10 electron microscope. Given is the size of particles that were present in infected and not present in non-infected cultures.
[3]Sensitivity to chloroform was determined according to standard techniques (Grist, Ross, and Bell; 1974).
[4]Hundred to 300 TCID$_{50}$ of isolates were mixed with varying dilutions of specific antisera and grown in the appropriate cell system until full CPE was observed. Sera with titres higher then 5 were retested, and sera which blocked with high titres the CPE were considered specific for the isolate. The isolates not sensitive to chloroform were tested with sera specifically directed against porcine entero viruses (PEV) 1 to 11 (courtesy Dr. Knowles, Pirbright, UK), against encephalomyocarditis virus (EMCV; courtesy Dr. Ahl, Tubingen, Germany), against porcine parvo virus, and against swine vesicular disease. The isolate (code: CDI-NL-2.91) sensitive to chloroform was tested with antisera specifically directed against pseudo-rabies virus, bovine herpes virus 1, bovine herpes virus 4, malignant catarrhal virus, bovine viral diarrhoea virus, hog cholera virus, swine influenza virus H1N1 and H3N2, parainfluenza 3 virus, bovine respiratory syncitial virus, transmissible gastroenteritis virus, porcine epidemic diarrhoea virus, haemaglutinating encephalitis virus, infectious bronchitis virus, bovine leukemia virus, avian leukemia virus, maedi-visna virus, and with the experimental sera obtained from the SPF-pigs (see Table 5).

TABLE 4

Results of serology of paired field sera taken from sows suspected to have MSD. Sera were taken in the acute phase of the disease and 3–9 weeks later. Given is the number of sows which showed a fourfold or higher rise in titre/number of sows tested.

| Farm | Interval[i] in weeks | HAI HEV | H1N1 | H3N2 | ELISA PBV | PPV | BVDV | HCV |
|---|---|---|---|---|---|---|---|---|
| TH | 3 | 0/6 | 0/6 | 0/6 | 0/6 | 0/6 | 0/5 | 0/6 |
| RB | 5 | 0/13 | 1/13 | 0/13 | 1/9 | 0/7 | 0/6 | 0/9 |
| HU | 4 | 0/5 | 0/5 | 3/5 | 0/5 | 0/5 | 0/5 | 0/5 |
| TS | 3 | 1/10 | 0/10 | 0/10 | 0/10 | 0/10 | 0/4 | 0/10 |
| VL | 3 | 0/5 | 0/5 | 0/5 | 0/5 | 1/5 | 0/5 | 0/5 |
| JA | 3 | 0/11 | 1/11 | 3/11 | 0/11 | 2/11 | 0/11 | 0/11 |
| WE | 4 | 1/6 | 1/6 | 1/6 | 3/7 | 3/7 | 0/7 | 0/7 |
| GI | 4 | 0/4 | 1/4 | 0/4 | 0/4 | 0/7 | 0/4 | 0/4 |
| SE | 5 | 0/8 | 0/8 | 0/8 | 0/8 | 0/6 | 0/3 | 0/8 |

TABLE 4-continued

Results of serology of paired field sera taken from sows suspected to have MSD. Sera were taken in the acute phase of the disease and 3-9 weeks later. Given is the number of sows which showed a fourfold or higher rise in titre/number of sows tested.

| Farm | Interval | | | | | | | |
|---|---|---|---|---|---|---|---|---|
| KA | 5 | 0/1 | 0/1 | 0/1 | 0/1 | 0/1 | ND | 0/1 |
| HO | 3 | 1/6 | 0/5 | 1/6 | 0/6 | 0/6 | 0/6 | 0/6 |
| NY | 4 | 0/5 | 1/5 | 1/5 | 0/3 | 0/4 | 0/2 | 0/4 |
| JN | 3 | 0/10 | 5/10 | 0/10 | 0/10 | 1/10 | 0/10 | 0/10 |
| KO[f] | 3 | 1/10 | 0/10 | 0/10 | 0/10 | 2/10 | 0/10 | 0/10 |
| OE | 9 | ND | ND | ND | 0/6 | 0/6 | 0/6 | 0/6 |
| LO | 6 | ND | ND | ND | 0/3 | 0/3 | 0/2 | 0/3 |
| WI | 4 | ND | ND | ND | 0/1 | 1/1 | 0/1 | 0/3 |
| RR | 3 | ND | ND | ND | 1/8 | 0/8 | 0/8 | 0/8 |
| RY | 4 | ND | ND | ND | 0/3 | 0/4 | 0/3 | 0/4 |
| BE | 5 | ND | ND | ND | 10 | 0/10 | 0/10 | 0/10 |
| BU | 3 | ND | ND | ND | 1/6 | 0/6 | 0/6 | 0/6 |
| KR | 3 | ND | ND | ND | 1/4 | 0/4 | 0/4 | 0/4 |
| KW | 5 | ND | ND | ND | 0/10 | 0/10 | 0/10 | 0/10 |
| VR | 5 | ND | ND | ND | 1/6 | 0/6 | 0/6 | 0/6 |
| HU | 4 | ND | ND | ND | 1/4 | 0/3 | 0/3 | 0/4 |
| ME | 3 | ND | ND | ND | 0/5 | 1/5 | 0/5 | 0/5 |
| total negative[n] | | 19 | 41 | 29 | 97 | 16 | 140 | 165 |
| total positive[p] | | 77 | 48 | 62 | 55 | 131 | 1 | 0 |
| total sero-converted[s] | | 4 | 10 | 9 | 9 | 11 | 0 | 0 |
| total tested | | 100 | 99 | 100 | 161 | 158 | 141 | 165 |

The sera were tested in haemagglutinating inhibition (HAI) tests for the detection of antibody against haemagglutinating encephalitis virus (HEV), and swine influenza viruses H1N1 and H3N2, in enzyme-linked-immuno sorbent assays (ELISA) for the detection of antibody against the glycoprotein gI of pseudorabies virus (PRV), against porcine parvo virus (PPV), bovine viral diarrhoea virus (BVDV), and hog cholera virus (HCV).

| Farm | Interval in weeks | SNT FMCV | FMCVi | PEV2 | PEV2i | PEV7 | PEV7i | LA | IPMA LA |
|---|---|---|---|---|---|---|---|---|---|
| TH | 3 | 0/6 | 0/6 | 0/5 | 0/5 | 0/6 | 0/5 | 0/6 | 6/6 |
| RB | 5 | 1/7 | 1/9 | 0/6 | 2/6 | 1/8 | 0/6 | 0/13 | 7/9 |
| HU | 4 | ND | 0/5 | 0/5 | 0/5 | ND | 0/5 | 0/5 | 3/5 |
| TS | 3 | 0/10 | 0/10 | 0/7 | 0/4 | 0/10 | 0/7 | ND | 10/10 |
| VL | 3 | ND | ND | 1/5 | 0/5 | ND | 0/5 | ND | 5/5 |
| JA | 3 | 0/11 | 0/11 | 0/11 | 0/11 | 1/11 | 2/11 | 0/5 | 8/11 |
| WE | 4 | 1/7 | 1/6 | 1/6 | 1/7 | 1/7 | 1/7 | 0/7 | 7/7 |
| GI | 4 | 0/4 | 0/4 | 0/4 | 0/4 | 0/4 | 0/4 | 0/4 | 4/4 |
| SE | 5 | 0/8 | 0/8 | 0/6 | 1/8 | 0/8 | 1/5 | 0/8 | 6/8 |
| KA | 5 | 0/1 | 0/1 | 0/1 | 0/1 | 0/1 | 0/1 | 0/1 | 0/1 |
| HO | 3 | 0/6 | 0/6 | 0/6 | 0/6 | 0/6 | 0/6 | 0/6 | 4/6 |
| NY | 4 | 0/4 | 0/4 | 0/2 | 0/2 | 0/4 | 0/3 | 0/4 | 4/4 |
| JN | 3 | 0/10 | 0/10 | 1/10 | 0/9 | 0/10 | 0/10 | 0/10 | 5/10 |
| KO[f] | 3 | 0/10 | 0/10 | 2/10 | 2/10 | 1/10 | 3/10 | ND | 8/10 |
| OE | 9 | 0/6 | 0/6 | 1/6 | 1/5 | ND | 1/6 | ND | 4/6 |
| LO | 6 | 0/3 | 0/3 | 0/3 | 0/3 | 0/3 | 0/3 | ND | 3/3 |
| WI | 4 | ND | ND | 0/1 | 0/1 | ND | 0/1 | ND | 0/3 |
| RR | 3 | 0/8 | 1/8 | 0/8 | 0/8 | 0/8 | 0/8 | ND | 8/8 |
| RY | 4 | 0/4 | ND | 0/4 | 0/1 | | | | |
| BE | 5 | ND | ND | 0/10 | 0/10 | ND | 1/10 | ND | 0/10 |
| BU | 3 | ND | ND | 0/6 | 0/6 | ND | 0/6 | ND | 6/6 |
| KR | 3 | ND | ND | 0/4 | 0/4 | ND | 0/4 | ND | 1/4 |
| KW | 5 | ND | ND | 0/10 | 0/10 | ND | 1/10 | ND | 10/10 |
| VR | 5 | ND | ND | 0/6 | 1/6 | ND | 0/6 | Nn | 6/6 |
| HU | 4 | ND | ND | 0/3 | 0/4 | ND | 0/3 | ND | 3/4 |
| ME | 3 | ND | ND | 0/5 | 0/5 | ND | 0/5 | ND | 2/5 |
| total neg.[n] | | 15 | 29 | 0 | 0 | 2 | 1 | 69 | 15 |
| total pos.[p] | | 88 | 74 | 144 | 138 | 90 | 136 | 0 | 27 |
| total sero-converted[s] | | 2 | 3 | 6 | 8 | 4 | 10 | 0 | 123 |
| total tested | | 105 | 107 | 150 | 146 | 96 | 147 | 69 | 165 |

The sera were tested in serum neutralization tests (SNT) for the detection of neutralizing antibody directed against encephalomyocarditis virus (EMCV), the isolated (i) EMCV, porcine entero viruses (PEV) 2 and 7 and the PEV isolates (i), and against the Lelystad agent (LA), and were tested in an immuno-peroxidase-monolayer-assay (IPMA) for the detection of antibody directed against the Lelystad agent (LA). [f]fattening pigs. [i]time between sampling of the first and second serum. [n]total number of pigs of which the first serum was negative in the test under study, and of which the second serum was also negative or showed a less then fourfold rise in titre. [p]total number of pigs of which the first serum was fourfold rise in titre. [s]total number of pigs of which the second serum had a fourfold or higher titre then the first serum in the test under study. ND = not done.

TABLE 5

Development of antibody directed against Lelystad agent as measured by IPMA.

A contact pigs

| Weeks post contact: | serum titres in IPMA | | | | |
|---|---|---|---|---|---|
| Pig | 0 | 2 | 3 | 4 | 5 |
| c 836 | 0 | 10 | 640 | 640 | 640 |
| c 837 | 0 | 10 | 640 | 640 | 640 |
| c 821 | 0 | 640 | 640 | 640 | 640 |
| c 823 | 0 | 160 | 2560 | 640 | 640 |
| c 829 | 0 | 160 | 640 | 10240 | 10240 |
| c 832 | 0 | 160 | 640 | 640 | 2560 |
| c 813 | 0 | 640 | 2560 | 2560 | 2560 |
| c 815 | 0 | 160 | 640 | 640 | 640 |

B blood inoculated pigs

| Weeks post inoculation: | serum titres in IPMA | | | | |
|---|---|---|---|---|---|
| | 0 | 2 | 3 | 4 | 6 |
| b 809 | 0 | 640 | 2560 | 2560 | 2560 |
| b 817 | 0 | 160 | 640 | 640 | 640 |
| b 818 | 0 | 160 | 640 | 640 | 640 |
| b 820 | 0 | 160 | 640 | 640 | 640 |
| b 822 | 0 | 640 | 2560 | 2560 | 10240 |
| b 826 | 0 | 640 | 640 | 640 | 10240 |
| B 830 | 0 | 640 | 640 | 640 | 2560 |
| B 834 | 0 | 160 | 640 | 2560 | 640 |

See Table 2 for description of the experiment. All pigs were bled at regular intervals and all sera were tested in an immuno-peroxidase-monolayer-assay (IPMA) for the detection of antibody directed against the Lelystad agent (LA).

TABLE 6

Experimental reproduction of MSD.

| sow | length of gestation | No. of piglets at birth alive (number Ab pos)[2] | dead | No. of deaths week 1 | LA[1] in piglets born dead | died in week 1 |
|---|---|---|---|---|---|---|
| 52 | 113 | 12(5) | 3(2) | 6 | 2 | 4 |
| 965 | 116 | 3(0) | 9(3) | 2 | 4 | |
| 997 | 114 | 9(0) | 1(0) | 0 | | |
| 1305 | 116 | 7(0) | 2(0) | 1 | | |
| 134 | 109 | 4(4) | 7(4) | 4 | 3 | |
| 941 | 117 | 7 | 10 | | | |
| 1056 | 113 | 7(1) | 3(0) | 4 | | |
| 1065 | 115 | 9 | 2 | | | |

[1]LA was isolated from lung, liver, spleen, kidney, or ascitic fluids.
[2]Antibodies directed against LA were detected in serum samples taken before the piglets had sucked, or were detected in ascitic fluids of piglets born dead.

TABLE 7

Reactivity in IPMA of a collection of field sera from Europe and North-America tested with LA isolates from the Netherlands (NL1 and NL2), Germany (GE1 and GE2), and the United States (US1, US2 and US3).

| Isolates: | NL1 | NL2 | GE1 | GE2 | US1 | US2 | US3 |
|---|---|---|---|---|---|---|---|
| Sera from: | | | | | | | |
| The Netherlands | | | | | | | |
| TH-187 | 3.5[t] | 3.5 | 2.5 | 3.5 | – | – | – |
| TO-36 | 3.5 | 3.0 | 2.5 | 3.0 | – | 1.0 | – |
| Germany | | | | | | | |
| BE-352 | 4.0 | 3.5 | 2.5 | 3.0 | – | 1.5 | – |
| BE-392 | 3.5 | 3.5 | 2.5 | 2.5 | 1.5 | 1.5 | 0.5 |
| NI-f2 | 2.5 | 1.5 | 2.0 | 2.5 | – | – | – |
| United Kingdom | | | | | | | |
| PA-141615 | 4.0 | 3.0 | 3.0 | 3.5 | – | – | – |
| PA-141617 | 4.0 | 3.5 | 3.0 | 3.5 | – | 2.5 | 2.0 |
| PA-142440 | 3.5 | 3.0 | 2.5 | 3.5 | – | 2.0 | 2.5 |
| Belgium | | | | | | | |
| PE-1960 | 4.5 | 4.5 | 3.0 | 4.0 | 1.5 | – | – |
| France | | | | | | | |
| EA-2975 | 4.0 | 3.5 | 3.0 | 3.0 | 2.0 | – | – |
| EA-2985 | 3.5 | 3.0 | 3.0 | 2.5 | – | – | – |
| United States | | | | | | | |
| SL-441 | 3.5 | 1.5 | 2.5 | 2.5 | 3.5 | 3.5 | 3.0 |
| SL-451 | 3.0 | 2.0 | 2.5 | 2.5 | 3.5 | 4.5 | 4.0 |
| AL-RP9577 | 1.5 | – | – | 1.0 | 3.0 | 4.0 | 2.5 |
| AL-P10814/33 | 0.5 | 2.5 | – | – | 2.5 | 3.5 | 3.0 |
| AL-4094A | – | – | – | – | 1.0 | 2.0 | 0.5 |
| AL-7525 | – | – | – | – | – | 1.0 | – |
| JC-MN41 | – | – | – | – | 1.0 | 3.5 | 1.0 |
| JC-MN44 | – | – | – | – | 2.0 | 3.5 | 2.0 |
| JC-MN45 | – | – | – | – | 2.0 | 3.5 | 2.5 |
| Canada | | | | | | | |
| RB-16 | 2.5 | – | 3.0 | 2.0 | 3.0 | 3.5 | – |
| RB-19 | 1.0 | – | 1.0 | – | 2.5 | 1.5 | – |
| RB-22 | 1.5 | – | 2.0 | 2.5 | 2.5 | 3.5 | – |
| RB-23 | – | – | – | – | – | 3.0 | – |

[t] = titre expressed as negative log; – = negative

TABLE 8

Reactivity in IPMA of a collection of experimental sera raised against LA and SIRSV tested with LA isolates from the Netherlands (NL1 and NL2), Germany (GE1 and GE2), and the United States (US1, US2 and US3).

| Isolates: | | NL1 | NL2 | GE1 | GE2 | US1 | US2 | US3 |
|---|---|---|---|---|---|---|---|---|
| Sera: | | | | | | | | |
| anti-LA: | | | | | | | | |
| 21 | 14 dpi | 2.5[t] | 2.0 | 2.5 | 3.0 | 1.5 | 2.0 | 1.5 |
| | 28 dpi | 4.0 | 3.5 | 3.5 | 4.0 | – | 2.5 | 1.5 |
| | 42 dpi | 4.0 | 3.5 | 3.0 | 3.5 | 1.5 | 2.5 | 2.0 |
| 23 | 14 dpi | 3.0 | 2.0 | 2.5 | 3.0 | 1.0 | 2.0 | 1.0 |
| | 28 dpi | 3.5 | 3.5 | 3.5 | 4.0 | 1.5 | 2.0 | 2.0 |
| | 42 dpi | 4.0 | 4.0 | 3.0 | 4.0 | – | 2.5 | 2.5 |
| 25 | 14 dpi | 2.5 | 2.0 | 2.5 | 3.0 | 1.5 | 2.0 | 1.0 |
| | 28 dpi | 4.0 | 3.5 | 4.0 | 3.5 | – | 1.5 | 2.0 |
| | 42 dpi | 3.5 | 4.0 | 3.5 | 3.5 | 1.5 | 2.0 | 2.0 |
| 29 | 14 dpi | 3.5 | 3.5 | 3.0 | 3.5 | – | 2.0 | 1.5 |
| | 28 dpi | 3.5 | 3.5 | 3.5 | 3.5 | – | 2.5 | 2.0 |
| | 42 dpi | 4.0 | 3.5 | 3.5 | 4.0 | 1.5 | 2.5 | 2.5 |
| anti-SISRV: | | | | | | | | |
| 2B | 20 dpi | – | – | – | – | 2.0 | 2.0 | – |
| | 36 dpi | – | – | – | – | 1.5 | 2.0 | – |
| | 63 dpi | – | – | – | – | 1.0 | 1.0 | – |
| 9G | 30 dpi | – | – | – | – | 2.5 | 3.0 | – |
| | 44 dpi | – | – | – | – | 2.5 | 3.5 | – |
| | 68 dpi | – | – | – | – | 2.0 | 3.5 | 1.5 |
| 16W | 25 dpi | – | – | – | – | 2.0 | 3.0 | – |

TABLE 8-continued

Reactivity in IPMA of a collection of experimental sera raised against LA and SIRSV tested with LA isolates from the Netherlands (NL1 and NL2), Germany (GE1 and GE2), and the United States (US1, US2 and US3).

| Isolates: | | NL1 | NL2 | GE1 | GE2 | US1 | US2 | US3 |
|---|---|---|---|---|---|---|---|---|
| | 40 dpi | – | – | – | – | 2.0 | 3.0 | – |
| | 64 dpi | – | – | – | – | 2.5 | 2.5 | 1.5 |
| 16Y | 36 dpi | – | – | – | – | 1.0 | 3.0 | 1.0 |
| | 64 dpi | – | – | – | – | 2.5 | 3.0 | – |

$^t$ = titer expressed as negative log; – = negative

TABLE 9

Characteristics of the ORFs of Lelystad Virus.

| ORF | Nucleotides (first-last) | No. of amino acids | Calculated size of the unmodified peptide (kDa) | number of glycosylation sites |
|---|---|---|---|---|
| ORF1A | 212–7399 | 2396 | 260.0 | 3 (SEQ ID NO: 2) |
| ORF1B | 7384–11772 | 1463 | 161.8 | 3 (SEQ ID NO: 3) |
| ORF2 | 11786–12532 | 249 | 28.4 | 2 (SEQ ID NO: 4) |
| ORF3 | 12394–13188 | 265 | 30.6 | 7 (SEQ ID NO: 5) |
| | 12556–13188 | 211 | 24.5 | 4 (SEQ ID NO: 6) |
| ORF4 | 12936–13484 | 183 | 20.0 | 4 |
| | 12981–13484 | 168 | 18.4 | 4 |
| | 13068–13484 | 139 | 15.4 | 3 |
| ORF5 | 13484-14086 | 201 | 22.4 | 2 (SEQ ID NO: 7) |
| ORF6 | 14077-14595 | 173 | 18.9 | 2 (SEQ ID NO: 8) |
| ORF7 | 14588-14971 | 128 | 13.8 | 1 (SEQ ID NO: 9) |

References

Boer, G. F. de, Back, W., and Osterhaus, A. D. M. E., (1990) An ELISA for detection of antibodies against influenza A nucleoprotein in human and various animal species, Arch. Virol. 115, 47–61.

Boursnell, M. E. G., Brown, T. D. K., and Binns, M. M., (1984) Sequence of the membrane protein gene from avian coronavirus IBV, Virus Res. 1, 303–314.

Boursnell, M. E. G., Brown, T. D. K., Foulds, I. J., Green, P. F., Tomley F. M., and Binns, M. M., (1987) Completion of the sequence of the genome of the coronavirus avian infectious bronchitis virus, J. Gen. Virol. 68, 57–77.

Brakke, M. K., (1967) In: Methods in Virology, Volume II, pp. 93–117 (Edited by K. Maramorosch and H. Koprowski) New York, Academic Press.

Bredenbeek, P. J., Pachuk, C. J., Noten, J. F. H., Charité, J., Luytjes, W., Weiss, S. R., and Spaan, W. J. M., (1990) The primary structure and expression of the second open reading frame of the polymerase gene of coronavirus MHV-A59. Nucleic Acids Res. 18, 1825–1832.

Brenner, S., and Horne, R. W., (1959) A negative staining method for high resolution electron microscopy of viruses, Biochimica et Biophysica Acta 34, 103–110.

Brinton-Darnell, M., and Plagemann, P. G., (1975) Structure and chemical-physical characteristics of lactate dehydrogenase-elevating virus and its RNA, J. Virol. 16, 420–433.

Favaloro, J., Treisman, R. & Kamen, R., (1980) In: Methods in Enzymology, vol. 65, 718–749 (eds. Grossman, L. & Moldave, K.) Academic Press, New York.

Godeny, E. K., Speicher, D. W., and Brinton, M. A., (1990) Map location of lactate dehydrogenase-elevating virus (LDV) capsid protein (Vp1) gene, Virology, 177, 768–771.

Grist, N. R., Ross, C. A., and Bell, E. J., (1974) In: Diagnostic Methods in Clinical Virology, p. 120, Oxford, Blackwell Scientific Publications.

Gübler, U., and Hoffman, B. J., (1983) A simple and very efficient method for generating cDNA libraries, Gene 25, 263–269.

Hanahan, D., (1985) In: DNA Cloning I; A Practical Approach, Chapter 6, 109–135.

Hill, H., (1990) Overview and History of Mystery Swine Disease (Swine Infertility Respiratory Syndrome), In: Proceedings of the Mystery Swine Disease Committee Meeting, Oct. 6, 1990, Denver, Colo., Livestock Conservation Institute, Madison Wis., USA.

Hirsch, J. G. & Fedorko, M. E., (1968) Ultrastructure of human leucocytes after simultaneous fixation with glutaraldehyde and osmiumtetroxide and postfixation in uranylacetate, Journal of Cellular Biology 38, 615.

Horzinek, M. C., Maess, J., and Laufs, R., (1971) Studies on the substructure of togaviruses II. Analysis of equine arteritis, rubella, bovine viral diarrhea and hog cholera viruses, Arch. Gesamte Virusforsch. 33, 306–318.

Hyllseth, B., (1973) Structural proteins of equine arteritis virus, Arch. Gesamte Virusforsch. 40, 177–188.

Kasza, L., Shadduck, J. A., and Christoffinis, G. J., (1972) Establishment, viral susceptibility and biological characteristics of a swine kidney cell line SK-6, Res. Vet. Sci. 13, 46–51.

Loula, T., (1990) Clinical Presentation of Mystery Pig Disease in the breeding herd and suckling piglets, In: Proceedings of the Mystery Swine Disease Committee Meeting, Oct. 6, 1990, Denver, Colo., Livestock Conservation Institute, Madison, Wis., USA.

Masurel, N., (1976) Swine influenza virus and the recycling of influenza A viruses in man, Lancet ii, 244–247.

Mazancourt, A. de, Waxham, M. N., Nicholas, J. C., & Wolinsky, J. S., (1986) Antibody response to the rubella virus structural proteins in infants with the congenital rubella syndrome. J. Med. Virol. 19, 111–122.

Mengeling, W. L., and Lager, K. M., (1990) Mystery Pig Disease: Evidence and considerations for its etiology, In: Proceedings of the Mystery Swine Disease Committee Meeting, Oct. 6, 1990, Denver, Colo., Livestock Conservation Institute, Madison, Wis., USA.

Moormann, R. J. M., and Hulst, M. M., (1988) Hog cholera virus: identification and characterization of the viral RNA and virus-specific RNA synthesized in infected swine kidney cells, Virus Res. 11, 281–291.

Moormann, R. J. M., Warmerdam, P. A. M., van der Meer, B., Schaaper, W. M. M., Wensvoort, G., and Hulst, M. M., (1990) Molecular cloning and nucleotide sequence of hog cholera virus strain Brescia and mapping of the genomic region encoding envelope protein E1, Virology, 177, 184–198.

Oirschot, J. T. van, Houwers, D. J., Rziha, H. J., and Moonen, P. J. L. M., (1988) Development of an ELISA for detection of antibodies to glycoprotein I of Aujeszky's disease virus: a method for the serological differentiation between infected and vaccinated pigs, J. Virol. Meth. 22, 191–206.

Pearson, W. R., and Lipman, D. J., (1988) Improved tools for biological sequence comparison. Proc. Natl. Acad. Sci. USA 85, 2444–2448.

Reed, L. J., and Muench, H., (1938) A simple method of estimating fifty percent endpoints, Am. J. Hyg. 27, 493–497.

Rottier, P. J. M., Welling, G. W., Welling-Wester, S., Niesters, H. G. M., Lenstra, J. M., and van der Zeijst, B. A. M., (1986) Predicted membrane topology of the coronavirus protein E1. Biochemistry 25, 1335–1339.

Sambrook, J., Fritsch, E. F., and Maniatis, T., (1989) Molecular Cloning, A Laboratory Manual. Cold Spring Harbor Lab., Cold Spring Harbor, N.Y.

Sethna, P. B., Hung, S.-L., and Brian, D. A., (1989) Coronavirus subgenomic minus-strand RNAs and the potential for mRNA replicons, Proc. Natl. Acad. Sci. USA, 86, 5626–5630.

Setzer, D. R., McGrogan, M., Nunberg, J. H. & Schimke, R. T., (1980) Size heterogeneity in the 3'-end of the dehydrofolate reductase messenger RNA's in mouse cells, Cell 22, 361–370.

Snijder, E. J., den Boon, J. A., Bredenbeek, P. J., Horzinek, M. C., Rijnbrand, R., and Spaan, W. J. M., (1990a) The carboxyl-terminal part of the putative Berne virus polymerase is expressed by ribosomal frameshifting and contains sequence motifs which indicate that toro- and coronaviruses are evolutionary related, Nucleic Acids Res. 18, 4535–4542.

Snijder, E. J., Horzinek, M. C., and Spaan, W. J. M., (1990b) A 3'-coterminal nested set of independently transcribed messenger RNAs is generated during Berne virus replication. J. Virol. 64, 355–363.

Spaan, W. J. M., Cavanagh, D., and Horzinek, M. C., (1988) Coronaviruses: structure and genome expression. J. Gen. Virol. 69, 2939–2952.

Strauss, W. M., (1987) Preparation of genomic DNA from mammalian tissue, In: Current protocols in molecular biology (eds. Ausubel F. M. et al.) 2.2.1 John Wiley & Sons, New York.

Terpstra, C., (1978) Detection of Border disease antigen in tissues of affected sheep and in cell cultures by immunofluorescence, Res. Vet. Sci. 25, 350–355.

Venable, J. H. & Coggeshall, R., (1965) A simplified lead citrate stain for use in electronmicroscopy, Journal of Cellular Biology 25, 407.

Vries, A. A. F. de, Chirnside, E. D., Bredenbeek, P. J., Gravestein, L. A., Horzinek, M. C., and Spaan, W. J. M., (1990) All subgenomic mRNAs of equine arteritis virus contain a common leader sequence, Nucleic Acids Res. 18, 3241–3247.

Wensvoort, G., and Terpstra, C., (1988) Bovine viral diarrhoea infections in piglets from sows vaccinated against swine fever with contaminated vaccine, Res. Vet. Sci. 45, 143–148.

Wensvoort, G., Terpstra, C., and Bloemraad, M., (1988) An enzyme immunoassay, employing monoclonal antibodies and detecting specifically antibodies against classical swine fever virus, Vet. Microbiol. 17, 129–140.

Wensvoort, G., Terpstra, C., Boonsta, J., Bloemraad, M., and Zaane, D. van, (1986) Production of monoclonal antibodies against swine fever virus and their use in laboratory diagnosis, Vet. Microbiol. 12, 101–108.

Wensvoort, G., Terpstra, C., and Kluyver, E. P. de, (1988) Characterization of porcine and some ruminant pestiviruses by cross-neutralization, Vet. Microbiol. 20, 291–306.

Westenbrink, F., Middel, W. G. J., Straver, P., and Leeuw, P. W. de, (1986) A blocking enzyme-linked immunosorbent assay (ELISA) for bovine virus diarrhoea virus serology, J. Vet. Med. B33, 354–361.

Westenbrink, F., Veldhuis, M. A., and Brinkhof, J. M. A., (1989) An enzyme-linked immunosorbent assay for detection of antibodies to porcine parvo virus, J. Virol. Meth. 23, 169–178.

Zeijst, B. A. M. van der, Horzinek, M. C., and Moenning, V., (1975) The genome of equine arteritis virus, Virology, 68, 418–425.

---

We claim:

1. An isolated causative agent of Mystery Swine Disease identified as deposit number I-1102, deposited Jun. 5, 1991 with the Institut Pasteur, Paris, France.

2. A composition of matter comprising virus identified as Institut Pasteur deposit number I-1102.

3. A composition of matter in accordance with claim 2 wherein said virus is killed.

4. A vaccine composition comprising a virus having all the attributes of Lelystad Agent deposited Jun. 5, 1991 with the Institut Pasteur, Paris, France, deposit number I-1102, and a suitable carrier.

5. A vaccine composition in accordance with claim 4 wherein the virus is killed.

6. The vaccine composition of claim 4 further comprising an adjuvant.

7. The vaccine composition of claim 5 further comprising an adjuvant.

8. Isolated Lelystad Agent comprising a virus, said virus characterized in being sensitive to chloroform and having a size smaller than 200 nanometers, said virus further being immunoreactive with serum antibodies of a sow, said serum antibodies obtained by:

a) intranasally inoculating the sow with two milliliters of the virus identified as deposit number I-1102, deposited Jun. 5, 1991 with the Institut Pasteur, Paris, France (at passage level 3, titer $10^{4.8}$ $TCID_{50}$/milliliter); and b) collecting serum antibodies from the thus inoculated sow after 25 to 33 days.

9. The isolated Lelystad Agent of claim 8 wherein said virus has been inactivated.

10. The isolated Lelystad Agent of claim 9 in combination with an adjuvant.

* * * * *

UNITED STATES PATENT AND TRADEMARK OFFICE
CERTIFICATE OF CORRECTION

PATENT NO. : 5,620,691

DATED : April 15, 1997

INVENTOR(S) : Wensvoort et al.

It is certified that error appears in the above-identified patent and that said Letters Patent is hereby corrected as shown below:

Title page, item [30]
Under "Foreign Application Priority Data", change "91201398" to --91201398.4--;

Column 6, line 64, change "respons" to --response--;

Column 7, line 1, change "FIGS. 1a through 1g" to --FIGS. 1a through 1q--;

Column 8, line 67, change "1.5" to --1:5--;

Column 11, line 60, change "DATP" to --dATP--;

Column 13, line 32, change "isolated" to --isolates--;

Column 13, line 38, change "Pk2" to --PK2--;

Column 13, line 39, after "of" insert --these SPF pigs. Seven of the 12 pigs were positive (Table 2),--;

Column 13, line 65, insert the following paragraph --In group three, SPF pgis kept in contact with MSD affected sows, LA was isolated from four of the 12 pigs; PEV 7 was isolated from seven pigs. All 12 pigs seroconverted to LA and PEV 7.--

Column 14, line 9, change "out" to --not--;

Column 16, line 46, change "or" to --of--;

Column 16, line 52, change "encoded" to --encode--;

UNITED STATES PATENT AND TRADEMARK OFFICE
CERTIFICATE OF CORRECTION

PATENT NO. : 5,620,691
DATED : April 15, 1997
INVENTOR(S) : Wensvoort et al.

It is certified that error appears in the above-identified patent and that said Letters Patent is hereby corrected as shown below:

Column 17, line 43, after "ORF" insert --6--;

Column 17, line 52, after "ORF 7" insert --(SEQ ID NO:9)--;

Column 19, Table 2, line 12, change "lung tonsil" to --lung, tonsil--.

Column 20, line 40, change "Tubingen" to --Tübingen--;

Column 21, Table 4 (cont), Row 11, column 6, change "10" to --0/10--;

Column 21, Table 4 (cont), Row 3, column 10, change "3/5" to --5/5--;

Column 21, Table 4 (cont-second half of table) Row 19, columns 7-10, insert --ND 1/4 ND 1/4--;

Column 21, Table 4 (cont-second half of table) Row 24 column 9, change "Nn" to --ND--;

Column 25, Table 9, Row 5, Column 5, after "4" delete "(SEQ ID NO:6)";

Column 25, Table 9, Row 6, Column 5, after "4" insert --(SEQ ID NO:6).

Signed and Sealed this

Thirteenth Day of April, 1999

*Attest:*

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 15108 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 212..7399

```
            ( D ) OTHER INFORMATION:

( i x ) FEATURE:
            ( A ) NAME/KEY: CDS
            ( B ) LOCATION: 7384..11772
            ( D ) OTHER INFORMATION:

( i x ) FEATURE:
            ( A ) NAME/KEY: CDS
            ( B ) LOCATION: 11786..12532
            ( D ) OTHER INFORMATION:

( i x ) FEATURE:
            ( A ) NAME/KEY: CDS
            ( B ) LOCATION: 12394..13188
            ( D ) OTHER INFORMATION:

( i x ) FEATURE:
            ( A ) NAME/KEY: CDS
            ( B ) LOCATION: 12936..13484
            ( D ) OTHER INFORMATION:

( i x ) FEATURE:
            ( A ) NAME/KEY: CDS
            ( B ) LOCATION: 13484..14086
            ( D ) OTHER INFORMATION:

( i x ) FEATURE:
            ( A ) NAME/KEY: CDS
            ( B ) LOCATION: 14077..14595
            ( D ) OTHER INFORMATION:

( i x ) FEATURE:
            ( A ) NAME/KEY: CDS
            ( B ) LOCATION: 14588..14971
            ( D ) OTHER INFORMATION:

( x i ) SEQUENCE DESCRIPTION: SEQ ID NO:1:

GGGTATTCCC  CCTACATACA  CGACACTTCT  AGTGTTTGTG  TACCTTGGAG  GCGTGGGTAC         60
AGCCCCGCCC  CACCCCTTGG  CCCCTGTTCT  AGCCCAACAG  GTATCCTTCT  CTCTCGGGGC        120
GAGTGCGCCG  CCTGCTGCTC  CCTTGCAGCG  GGAAGGACCT  CCCGAGTATT  TCCGGAGAGC        180
ACCTGCTTTA  CGGGATCTCC  ACCCTTTAAC  C ATGTCTGGGA  CGTTCTCCCG                  231
GTGCATGTGC  ACCCCGGCTG  CCCGGGTATT  TTGGAACGCC  GGCCAAGTCT  TTTGCACACG        291
GTGTCTCAGT  GCGCGGTCTC  TTCTCTCTCC  AGAGCTTCAG  GACACTGACC  TCGGTGCAGT        351
TGGCTTGTTT  TACAAGCCTA  GGGACAAGCT  TCACTGGAAA  GTCCCTATCG  GCATCCCTCA        411
GGTGGAATGT  ACTCCATCCG  GGTGCTGTTG  GCTCTCAGCT  GTTTTCCCTT  TGGCGCGTAT        471
GACCTCCGGC  AATCACAACT  TCCTCCAACG  ACTTGTGAAG  GTTGCTGATG  TTTTGTACCG        531
TGACGGTTGC  TTGGCACCTC  GACACCTTCG  TGAACTCCAA  GTTACGAGC   GCGGCTGCAA        591
CTGGTACCCG  ATCACGGGGC  CCGTGCCCGG  GATGGGTTTG  TTTGCGAACT  CCATGCACGT        651
ATCCGACCAG  CCGTTCCCTG  GTGCCACCCA  TGTGTTGACT  AACTCGCCTT  TGCCTCAACA        711
GGCTTGTCGG  CAGCCGTTCT  GTCCATTTGA  GGAGGCTCAT  TCTAGCGTGT  ACAGGTGGAA        771
GAAATTTGTG  GTTTTCACGG  ACTCCTCCCT  CAACGGTCGA  TCTCGCATGA  TGTGGACGCC        831
GGAATCCGAT  GATTCAGCCG  CCCTGGAGGT  ACTACCGCCT  GAGTTAGAAC  GTCAGGTCGA        891
AATCCTCATT  CGGAGTTTTC  CTGCTCATCA  CCCTGTCGAC  CTGGCCGACT  GGGAGCTCAC        951
TGAGTCCCCT  GAGAACGGTT  TTTCCTTCAA  CACGTCTCAT  TCTTGCGGTC  ACCTTGTCCA       1011
GAACCCCGAC  GTGTTTGATG  GCAAGTGCTG  GCTCTCCTGC  TTTTTGGGCC  AGTCGGTCGA       1071
AGTGCGCTGC  CATGAGGAAC  ATCTAGCTGA  CGCCTTCGGT  TACCAAACCA  AGTGGGGCGT       1131
GCATGGTAAG  TACCTCCAGC  GCAGGCTTCA  AGTTCGCGGC  ATTCGTGCTG  TAGTCGATCC       1191
TGATGGTCCC  ATTCACGTTG  AAGCGCTGTC  TTGCCCCCAG  TCTTGGATCA  GGCACCTGAC       1251
```

```
TCTGGATGAT GATGTCACCC CAGGATTCGT TCGCCTGACA TCCCTTCGCA TTGTGCCGAA    1311
CACAGAGCCT ACCACTTCCC GGATCTTTCG GTTTGGAGCG CATAAGTGGT ATGGCGCTGC    1371
CGGCAAACGG GCTCGTGCTA AGCGTGCCGC TAAAAGTGAG AAGGATTCGG CTCCCACCCC    1431
CAAGGTTGCC CTGCCGGTCC CCACCTGTGG AATTACCACC TACTCTCCAC CGACAGACGG    1491
GTCTTGTGGT TGGCATGTCC TTGCCGCCAT AATGAACGG ATGATAAATG GTGACTTCAC    1551
GTCCCCTCTG ACTCAGTACA ACAGACCAGA GGATGATTGG GCTTCTGATT ATGATCTTGT    1611
TCAGGCGATT CAATGTCTAC GACTGCCTGC TACCGTGGTT CGGAATCGCG CCTGTCCTAA    1671
CGCCAAGTAC CTTATAAAAC TTAACGAGT TCACTGGGAG GTAGAGGTGA GGTCTGGAAT    1731
GGCTCCTCGC TCCCTTTCTC GTGAATGTGT GGTTGGCGTT TGCTCTGAAG GCTGTGTCGC    1791
ACCGCCTTAT CCAGCAGACG GGCTACCTAA ACGTGCACTC GAGGCCTTGG CGTCTGCTTA    1851
CAGACTACCC TCCGATTGTG TTAGCTCTGG TATTGCTGAC TTTCTTGCTA ATCCACCTCC    1911
TCAGGAATTC TGGACCCTCG ACAAAATGTT GACCTCCCCG TCACCAGAGC GGTCCGGCTT    1971
CTCTAGTTTG TATAAATTAC TATTAGAGGT TGTTCCGCAA AAATGCGGTG CCACGGAAGG    2031
GGCTTTCATC TATGCTGTTG AGAGGATGTT GAAGGATTGT CCGAGCTCCA AACAGGCCAT    2091
GGCCCTTCTG GCAAAAATTA AGTTCCATC CTCAAAGGCC CCGTCTGTGT CCCTGGACGA    2151
GTGTTTCCCT ACGGATGTTT TAGCCGACTT CGAGCCAGCA TCTCAGGAAA GGCCCCAAAG    2211
TTCCGGCGCT GCTGTTGTCC TGTGTTCACC GGATGCAAAA GAGTTCGAGG AAGCAGCCCC    2271
RGAAGAAGTT CAAGAGAGTG GCCACAAGGC CGTCCACTCT GCACTCCTTG CCGAGGGTCC    2331
TAACAATGAG CAGGTACAGG TGGTTGCCGG TGAGCAACTG AAGCTCGGCG GTTGTGGTTT    2391
GGCAGTCGGG AATGCTCATG AAGGTGCTCT GGTCTCAGCT GGTCTAATTA ACCTGGTAGG    2451
CGGGAATTTG TCCCCCTCAG ACCCCATGAA AGAAAACATG CTCAATAGCC GGAAGACGA    2511
ACCACTGGAT TTGTCCCAAC CAGCACCAGC TTCCACAACG ACCCTTGTGA GAGAGCAAAC    2571
ACCCGACAAC CCAGGTTCTG ATGCCGGTGC CCTCCCCGTC ACCGTTCGAG AATTTGTCCC    2631
GACGGGGCCT ATACTCTGTC ATGTTGAGCA CTGCGGCACG GAGTCGGGCG ACAGCAGTTC    2691
GCCTTTGGAT CTATCTGATG CGCAAACCCT GGACCAGCCT TTAAATCTAT CCCTGGCCGC    2751
TTGGCCAGTG AGGGCCACCG CGTCTGACCC TGGCTGGGTC CACGGTAGGC GCGAGCCTGT    2811
CTTTGTAAAG CCTCGAAATG CTTTCTCTGA TGGCGATTCA GCCCTTCAGT TCGGGGAGCT    2871
TTCTGAATCC AGCTCTGTCA TCGAGTTTGA CCGGACAAAA GATGCTCCGG TGGTTGACGC    2931
CCCTGTCGAC TTGACGACTT CGAACGAGGC CCTCTCTGTA GTCGATCCTT TCGAATTTGC    2991
CGAACTCAAG CGCCCGCGTT TCTCCGCACA AGCCTTAATT GACCGAGGCG GTCCACTTGC    3051
CGATGTCCAT GCAAAAATAA GAACCGGGT ATATGAACAG TGCCTCCAAG CTTGTGAGCC    3111
CGGTAGTCGT GCAACCCCAG CCACCAGGGA GTGGCTCGAC AAAATGTGGG ATAGGGTGGA    3171
CATGAAAACT TGGCGCTGCA CCTCGCAGTT CCAAGCTGGT CGCATTCTTG CGTCCCTCAA    3231
ATTCCTCCCT GACATGATTC AAGACACACC GCCTCCTGTT CCCAGGAAGA ACCGAGCTAG    3291
TGACAATGCC GGCCTGAAGC AACTGGTGGC ACAGTGGGAT AGGAAATTGA GTGTGACCCC    3351
CCCCCCAAAA CCGGTTGGGC CAGTGCTTGA CCAGATCGTC CCTCCGCCTA CGGATATCCA    3411
GCAAGAAGAT GTCACCCCCT CCGATGGGCC ACCCCATGCG CCGGATTTTC CTAGTCGAGT    3471
GAGCACGGGC GGGAGTTGGA AAGGCCTTAT GCTTTCCGGC ACCCGTCTCG CGGGGTCTAT    3531
CAGCCAGCGC CTTATGACAT GGGTTTTTGA AGTTTTCTCC CACCTCCCAG CTTTTATGCT    3591
CACACTTTTC TCGCCGCGGG GCTCTATGGC TCCAGGTGAT TGGTTGTTTG CAGGTGTCGT    3651
```

```
TTTACTTGCT   CTCTTGCTCT   GTCGTTCTTA   CCCGATACTC   GGATGCCTTC   CCTTATTGGG    3711
TGTCTTTTCT   GGTTCTTTGC   GGCGTGTTCG   TCTGGGTGTT   TTTGGTTCTT   GGATGGCTTT    3771
TGCTGTATTT   TTATTCTCGA   CTCCATCCAA   CCCAGTCGGT   TCTTCTTGTG   ACCACGATTC    3831
GCCGGAGTGT   CATGCTGAGC   TTTTGGCTCT   TGAGCAGCGC   CAACTTTGGG   AACCTGTGCG    3891
CGGCCTTGTG   GTCGGCCCCT   CAGGCCTCTT   ATGTGTCATT   CTTGGCAAGT   TACTCGGTGG    3951
GTCACGTTAT   CTCTGGCATG   TTCTCCTACG   TTTATGCATG   CTTGCAGATT   TGGCCCTTTC    4011
TCTTGTTTAT   GTGGTGTCCC   AGGGGCGTTG   TCACAAGTGT   TGGGGAAAGT   GTATAAGGAC    4071
AGCTCCTGCG   GAGGTGGCTC   TTAATGTATT   TCCTTTCTCG   CGCGCCACCC   GTGTCTCTCT    4131
TGTATCCTTG   TGTGATCGAT   TCCAAACGCC   AAAAGGGGTT   GATCCTGTGC   ACTTGGCAAC    4191
GGGTTGGCGC   GGGTGCTGGC   GTGGTGAGAG   CCCCATCCAT   CAACCACACC   AAAAGCCCAT    4251
AGCTTATGCC   AATTTGGATG   AAAAGAAAAT   GTCTGCCCAA   ACGGTGGTTG   CTGTCCCATA    4311
CGATCCCAGT   CAGGCTATCA   AATGCCTGAA   AGTTCTGCAG   GCGGGAGGGG   CCATCGTGGA    4371
CCAGCCTACA   CCTGAGGTCG   TTCGTGTGTC   CGAGATCCCC   TTCTCAGCCC   CATTTTTCCC    4431
AAAAGTTCCA   GTCAACCCAG   ATTGCAGGGT   TGTGGTAGAT   TCGGACACTT   TTGTGGCTGC    4491
GGTTCGCTGC   GGTTACTCGA   CAGCACAACT   GGT Y CTGGGC   CGGGGCAACT   TTGCCAAGTT    4551
AAATCAGACC   CCCCCCAGGA   ACTCTATCTC   CACCAAAACG   ACTGGTGGGG   CCTCTTACAC    4611
CCTTGCTGTG   GCTCAAGTGT   CTGCGTGGAC   TCTTGTTCAT   TTCATCCTCG   GTCTTTGGTT    4671
CACATCACCT   CAAGTGTGTG   GCCGAGGAAC   CGCTGACCCA   TGGTGTTCAA   ATCCTTTTTC    4731
ATATCCTACC   TATGGCCCCG   GAGTTGTGTG   CTCCTCTCGA   CTTTGTGTGT   CTGCCGACGG    4791
GGTCACCCTG   CCATTGTTCT   CAGCCGTGGC   ACAACTCTCC   GGTAGAGAGG   TGGGGATTTT    4851
TATTTTGGTG   CTCGTCTCCT   TGACTGCTTT   GGCCCACCGC   ATGGCTCTTA   AGGCAGACAT    4911
GTTAGTGGTC   TTTTCGGCTT   TTTGTGCTTA   CGCCTGGCCC   ATGAGCTCCT   GGTTAATCTG    4971
CTTCTTTCCT   ATACTCTTGA   AGTGGGTTAC   CCTTCACCCT   CTTACTATGC   TTTGGGTGCA    5031
CTCATTCTTG   GTGTTTTGTC   TGCCAGCAGC   CGGCATCCTC   TCACTAGGGA   TAACTGGCCT    5091
TCTTTGGGCA   ATTGGCCGCT   TTACCCAGGT   TGCCGGAATT   ATTACACCTT   ATGACATCCA    5151
CCAGTACACC   TCTGGGCCAC   GTGGTGCAGC   TGCTGTGGCC   ACAGCCCCAG   AAGGCACTTA    5211
TATGGCCGCC   GTCCGGAGAG   CTGCTTTAAC   TGGGCGAACT   TTAATCTTCA   CCCCGTCTGC    5271
AGTTGGATCC   CTTCTCGAAG   GTGCTTTCAG   GACTCATAAA   CCCTGCCTTA   ACACCGTGAA    5331
TGTTGTAGGC   TCTTCCCTTG   GTTCCGGAGG   GGTTTTCACC   ATTGATGGCA   GAAGAACTGT    5391
CGTCACTGCT   GCCCATGTGT   TGAACGGCGA   CACAGCTAGA   GTCACCGGCG   ACTCCTACAA    5451
CCGCATGCAC   ACTTTCAAGA   CCAATGGTGA   TTATGCCTGG   TCCCATGCTG   ATGACTGGCA    5511
GGGCGTTGCC   CCTGTGGTCA   AGGTTGCGAA   GGGGTACCGC   GGTCGTGCCT   ACTGGCAAAC    5571
ATCAACTGGT   GTCGAACCCG   GTATCATTGG   GGAAGGGTTC   GCCTTCTGTT   TTACTAACTG    5631
CGGCGATTCG   GGGTCACCCG   TCATCTCAGA   ATCTGGTGAT   CTTATTGGAA   TCCACACCGG    5691
TTCAAACAAA   CTTGGTTCTG   GTCTTGTGAC   AACCCCTGAA   GGGGAGACCT   GCACCATCAA    5751
AGAAACCAAG   CTCTCTGACC   TTTCCAGACA   TTTTGCAGGC   CCAAGCGTTC   CTCTTGGGGA    5811
CATTAAATTG   AGTCCGGCCA   TCATCCCTGA   TGTAACATCC   ATTCCGAGTG   ACTTGGCATC    5871
GCTCCTAGCC   TCCGTCCCTG   TAGTGGAAGG   CGGCCTCTCG   ACCGTTCAAC   TTTTGTGTGT    5931
CTTTTTCCTT   CTCTGGCGCA   TGATGGGCCA   TGCCTGGACA   CCCATTGTTG   CCGTGGGCTT    5991
CTTTTTGCTG   AATGAAATTC   TTCCAGCAGT   TTTGGTCCGA   GCCGTGTTTT   CTTTTGCACT    6051
```

```
CTTTGTGCTT GCATGGGCCA CCCCCTGGTC TGCACAGGTG TTGATGATTA GACTCCTCAC    6111
GGCATCTCTC AACCGCAACA AGCTTTCTCT GGCGTTCTAC GCACTCGGGG GTGTCGTCGG    6171
TTTGGCAGCT GAAATCGGGA CTTTTGCTGG CAGATTGTCT GAATTGTCTC AAGCTCTTTC    6231
GACATACTGC TTCTTACCTA GGGTCCTTGC TATGACCAGT TGTGTTCCCA CCATCATCAT    6291
TGGTGGACTC CATACCCTCG GTGTGATTCT GTGGTTRTTC AAATACCGGT GCCTCCACAA    6351
CATGCTGGTT GGTGATGGGA GTTTTCAAG CGCCTTCTTC CTACGGTATT TTGCAGAGGG     6411
TAATCTCAGA AAAGGTGTTT CACAGTCCTG TGGCATGAAT AACGAGTCCC TAACGGCTGC    6471
TTTAGCTTGC AAGTTGTCAC AGGCTGACCT TGATTTTTTG TCCAGCTTAA CGAACTTCAA    6531
GTGCTTTGTA TCTGCTTCAA ACATGAAAAA TGCTGCCGGC CAGTACATTG AAGCAGCGTA    6591
TGCCAAGGCC CTGCGCCAAG AGTTGGCCTC TCTAGTTCAG ATTGACAAAA TGAAAGGAGT    6651
TTTGTCCAAG CTCGAGGCCT TTGCTGAAAC AGCCACCCCG TCCCTTGACA TAGGTGACGT    6711
GATTGTTCTG CTTGGGCAAC ATCCTCACGG ATCCATCCTC GATATTAATG TGGGGACTGA    6771
AAGGAAAACT GTGTCCGTGC AAGAGACCCG GAGCCTAGGC GGCTCCAAAT TCAGTGTTTG    6831
TACTGTCGTG TCCAACACAC CCGTGGACGC CTTRACCGGC ATCCCACTCC AGACACCAAC    6891
CCCTCTTTTT GAGAATGGTC CGCGTCATCG CAGCGAGGAA GACGATCTTA AAGTCGAGAG    6951
GATGAAGAAA CACTGTGTAT CCCTCGGCTT CCACAACATC AATGGCAAAG TTTACTGCAA    7011
AATTTGGGAC AAGTCTACCG GTGACACCTT TTACACGGAT GATTCCCGGT ACACCCAAGA    7071
CCATGCTTTT CAGGACAGGT CAGCCGACTA CAGAGACAGG GACTATGAGG GTGTGCAAAC    7131
CACCCCCCAA CAGGGATTTG ATCCAAAGTC TGAAACCCCT GTTGGCACTG TTGTGATCGG    7191
CGGTATTACG TATAACAGGT ATCTGATCAA AGGTAAGGAG GTTCTGGTCC CCAAGCCTGA    7251
CAACTGCCTT GAAGCTGCCA AGCTGTCCCT TGAGCAAGCT CTCGCTGGGA TGGGCCAAAC    7311
TTGCGACCTT ACAGCTGCCG AGGTGGAAAA GCTAAAGCGC ATCATTAGTC AACTCCAAGG    7371
TTTGACCACT GAACAGGCTT TAAACTGT TAGCCGCCAG CGGCTTGACC CGCTGTGGCC      7429
GCGGCGGCCT AGTTGTGACT GAAACGGCGG TAAAATTAT AAAATACCAC AGCAGAACTT     7489
TCACCTTAGG CCCTTTAGAC CTAAAAGTCA CTTCGAGGT GGAGGTAAAG AAATCAACTG     7549
AGCAGGGCCA CGCTGTTGTG GCAAACTTAT GTTCCGGTGT CATCTTGATG AGACCTCACC    7609
CACCGTCCCT TGTCGACGTT CTTCTGAAAC CCGGACTTGA CACAATACCC GGCATTCAAC    7669
CAGGGCATGG GGCCGGGAAT ATGGGCGTGG ACGGTTCTAT TTGGGATTTT GAAACCGCAC    7729
CCACAAAGGC AGAACTCGAG TTATCCAAGC AAATAATCCA AGCATGTGAA GTTAGGCGCG    7789
GGGACGCCCC GAACCTCCAA CTCCCTTACA AGCTCTATCC TGTTAGGGGG GATCCTGAGC    7849
GGCATAAAGG CCGCCTTATC AATACCAGGT TTGGAGATTT ACCTTACAAA ACTCCTCAAG    7909
ACACCAAGTC CGCAATCCAC GCGGCTTGTT GCCTGCACCC AACGGGGCC CCCGTGTCTG     7969
ATGGTAAATC CACACTAGGT ACCACTCTTC AACATGGTTT CGAGCTTTAT GTCCCTACTG    8029
TGCCCTATAG TGTCATGGAG TACCTTGATT CACGCCCTGA CACCCCTTTT ATGTGTACTA    8089
AACATGGCAC TTCCAAGGCT GCTGCAGAGG ACCTCCAAAA ATACGACCTA TCCACCCAAG    8149
GATTTGTCCT GCCTGGGGTC CTACGCCTAG TACGCAGATT CATCTTTGGC CATATTGGTA    8209
AGGCGCCGCC ATTGTTCCTC CCATCAACCT ATCCCGCCAA GAACTCTATG GCAGGGATCA    8269
ATGGCCAGAG GTTCCCAACA AAGGACGTTC AGAGCATACC TGAAATTGAT GAAATGTGTG    8329
CCCGCGCTGT CAAGGAGAAT TGGCAAACTG TGACACCTTG CACCCTCAAG AAACAGTACT    8389
GTTCCAAGCC CAAAACCAGG ACCATCCTGG GCACCAACAA CTTTATTGCC TTGGCTCACA    8449
```

```
GATCGGCGCT CAGTGGTGTC ACCCAGGCAT TCATGAAGAA GGCTTGGAAG TCCCCAATTG    8509
CCTTGGGGAA AAACAAATTC AAGGAGCTGC ATTGCACTGT CGCCGGCAGG TGTCTTGAGG    8569
CCGACTTGGC CTCCTGTGAC CGCAGCACCC CCGCCATTGT AAGATGGTTT GTTGCCAACC    8629
TCCTGTATGA ACTTGCAGGA TGTGAAGAGT ACTTGCCTAG CTATGTGCTT AATTGCTGCC    8689
ATGACCTCGT GGCAACACAG GATGGTGCCT TCACAAAACG CGGTGGCCTG TCGTCCGGGG    8749
ACCCCGTCAC CAGTGTGTCC AACACCGTAT ATTCACTGGT AATTTATGCC CAGCACATGG    8809
TATTGTCGGC CTTGAAAATG GGTCATGAAA TTGGTCTTAA GTTCCTCGAG GAACAGCTCA    8869
AGTTCGAGGA CCTCCTTGAA ATTCAGCCTA TGTTGGTATA CTCTGATGAT CTTGTCTTGT    8929
ACGCTGAAAG ACCCACMTTT CCCAATTACC ACTGGTGGGT CGAGCACCTT GACCTGATGC    8989
TGGGTTTCAG AACGGACCCA AAGAAACCG TCATAACTGA TAAACCCAGC TTCCTCGGCT     9049
GCAGAATTGA GGCAGGGCGA CAGCTAGTCC CCAATCGCGA CCGCATCCTG GCTGCTCTTG    9109
CATATCACAT GAAGGCGCAG AACGCCTCAG AGTATTATGC GTCTGCTGCC GCAATCCTGA    9169
TGGATTCATG TGCTTGCATT GACCATGACC CTGAGTGGTA TGAGGACCTC ATCTGCGGTA    9229
TTGCCCGGTG CGCCCGCCAG GATGGTTATA GCTTCCCAGG TCCGGCATTT TTCATGTCCA    9289
TGTGGGAGAA GCTGAGAAGT CATAATGAAG GAAGAAATT CCGCCACTGC GGCATCTGCG     9349
ACGCCAAAGC CGACTATGCG TCCGCCTGTG GGCTTGATTT GTGTTTGTTC CATTCGCACT    9409
TTCATCAACA CTGCCC Y GTC ACTCTGAGCT GCGGTCACCA TGCCGGTTCA AGGAATGTT    9469
CGCAGTGTCA GTCACCTGTT GGGGCTGGCA GATCCCCTCT TGATGCCGTG CTAAAACAAA    9529
TTCCATACAA ACCTCCTCGT ACTGTCATCA TGAAGGTGGG TAATAAAACA ACGGCCCTCG    9589
ATCCGGGGAG GTACCAGTCC CGTCGAGGTC TCGTTGCAGT CAAGAGGGGT ATTGCAGGCA    9649
ATGAAGTTGA TCTTTCTGAT GGRGACTACC AAGTGGTGCC TCTTTTGCCG ACTTGCAAAG    9709
ACATAAACAT GGTGAAGGTG GCTTGCAATG TACTACTCAG CAAGTTCATA GTAGGGCCAC    9769
CAGGTTCCGG AAAGACCACC TGGCTACTGA GTCAAGTCCA GGACGATGAT GTCATTTACA    9829
Y ACCCACCCA TCAGACTATG TTTGATATAG TCAGTGCTCT CAAAGTTTGC AGGTATTCCA    9889
TTCCAGGAGC CTCAGGACTC CCTTTCCCAC CACCTGCCAG GTCCGGGCCG TGGGTTAGGC    9949
TTATTGCCAG CGGGCACGTC CCTGGCCGAG TATCATACCT CGATGAGGCT GGATATTGTA    10009
ATCATCTGGA CATTCTTAGA CTGCTTTCCA AAACACCCCT TGTGTGTTTG GGTGACCTTC    10069
AGCAACTTCA CCCTGTCGGC TTTGATTCCT ACTGTTATGT GTTCGATCAG ATGCCTCAGA    10129
AGCAGCTGAC CACTATTTAC AGATTGGCC CTAACATCTG CGCACGCATC CAGCCTTGTT     10189
ACAGGGAGAA ACTTGAATCT AAGGCTAGGA ACACTAGGGT GGTTTTACC ACCCGGCCTG     10249
TGGCCTTTGG TCAGGTGCTG ACACCATACC ATAAAGATCG CATCGGCTCT GCGATAACCA    10309
TAGATTCATC CCAGGGGGCC ACCTTTGATA TTGTGACATT GCATCTACCA TCGCCAAAGT    10369
CCCTAAATAA ATCCCGAGCA CTTGTAGCCA TCACTCGGGC AAGACACGGG TTGTTCATTT    10429
ATGACCCTCA TAACCAGCTC CAGGAGTTTT TCAACTTAAC CCCTGAGCGC ACTGATTGTA    10489
ACCTTGTGTT CAGCCGTGGG GATGAGCTGG TAGTTCTGAA TGCGGATAAT GCAGTCACAA    10549
CTGTAGCGAA GGCCCTTGAG ACAGGTCCAT CTCGATTTCG AGTATCAGAC CCGAGGTGCA    10609
AGTCTCTCTT AGCCGCTTGT TCGGCCAGTC TGGAAGGGAG CTGTATGCCA CTACCGCAAG    10669
TGGCACATAA CCTGGGGTTT TACTTTTCCC CGGACAGTCC AACATTTGCA CCTCTGCCAA    10729
AAGAGTTGGC GCCACATTGG CCAGTGGTTA CCCACCAGAA TAATCGGGCG TGGCCTGATC    10789
GACTTGTCGC TAGTATGCGC CCAATTGATG CCCGCTACAG CAAGCCAATG GTCGGTGCAG    10849
```

```
GGTATGTGGT CGGGCCGTCC ACCTTTCTTG GTACTCCTGG TGTGGTGTCA TACTATCTCA    10909
CACTATACAT CAGGGGTGAG CCCCAGGCCT TGCCAGAAAC ACTCGTTTCA ACAGGGCGTA    10969
TAGCCACAGA TTGTCGGGAG TATCTCGACG CGGCTGAGGA AGAGGCAGCA AAAGAACTCC    11029
CCCACGCATT CATTGGCGAT GTCAAAGGTA CCACGGTTGG GGGGTGTCAT CACATTACAT    11089
CAAAATACCT ACCTAGGTCC CTGCCTAAGG ACTCTGTTGC CGTAGTTGGA GTAAGTTCGC    11149
CCGGCAGGGC TGCTAAAGCC GTGTGCACTC TCACCGATGT GTACCTCCCC GAACTCCGGC    11209
CATATCTGCA ACCTGAGACG GCATCAAAAT GCTGGAAACT CAAATTAGAC TTCAGGGACG    11269
TCCGACTAAT GGTCTGGAAA GGAGCCACCG CCTATTTCCA GTTGGAAGGG CTTACATGGT    11329
CGGCGCTGCC CGACTATGCC AGGTT Y ATTC AGCTGCCCAA GGATGCCGTT GTATACATTG    11389
ATCCGTGTAT AGGACCGGCA ACAGCCAACC GTAAGGTCGT GCGAACCACA GACTGGCGGG    11449
CCGACCTGGC AGTGACACCG TATGATTACG GTGCCCAGAA CATTTTGACA ACAGCCTGGT    11509
TCGAGGACCT CGGGCCGCAG TGGAAGATTT GGGGTTGCA GCCCTTTAGG CGAGCATTTG     11569
GCTTTGAAAA CACTGAGGAT TGGGCAATCC TTGCACGCCG TATGAATGAC GGCAAGGACT    11629
ACACTGACTA TAACTGGAAC TGTGTTCGAG AACGCCCACA CGCCATCTAC GGGCGTGCTC    11689
GTGACCATAC GTATCATTTT GCCCCTGGCA CAGAATTGCA GGTAGAGCTA GGTAAACCCC    11749
GGCTGCCGCC TGGGCAAGTG CCG TGAATTCGGG GTGATGCAAT GGGGTCACTG           11802
TGGAGTAAAA TCAGCCAGCT GTTCGTGGAC GCCTTCACTG AGTTCCTTGT TAGTGTGGTT    11862
GATATTG Y CA TTTTCCTTGC CATACTGTTT GGGTTCACCG TCGCAGGATG GTTACTGGTC   11922
TTTCTTCTCA GAGTGGTTTG CTCCGCGCTT CTCCGTTCGC GCTCTGCCAT TCACTCTCCC    11982
GAACTATCGA AGGTCCTATG AAGGCTTGTT GCCCAACTGC AGACCGGATG TCCCACAATT    12042
TGCAGTCAAG CACCCATTGG G Y ATGTTTTG GCACATGCGA GTTCCCACT TGATTGATGA    12102
GRTGGTCTCT CGTCGCATTT ACCAGACCAT GGAACATTCA GGTCAAGCGG CCTGGAAGCA    12162
GGTGGTTGGT GAGGCCACTC TCACGAAGCT GTCAGGGCTC GATATAGTTA CTCATTTCCA    12222
ACACCTGGCC GCAGTGGAGG CGGATTCTTG CCGCTTTCTC AGCTCACGAC TCGTGATGCT    12282
AAAAAATCTT GCCGTTGGCA ATGTGAGCCT ACAGTACAAC ACCACGTTGG ACCGCGTTGA    12342
GCTCATCTTC CCCACGCCAG GTACGAGGCC CAAGTTGACC GATTTCAGAC AATGGCTCAT    12402
CAGTGTGCAC GCTTCCATTT TTTCCTCTGT GGCTTCATCT GTTACCTTGT TCATAGTGCT    12462
TTGGCTTCGA ATTCCAGCTC TACGCTATGT TTTTGGTTTC CATTGGCCCA CGGCAACACA    12522
TCATTCGAGC TGACCATCAA CTACACCATA TGCATGCCCT GTTCTACCAG TCAAGCGGCT    12582
CGCCAAAGGC TCGAGCCCGG TCGTAACATG TGGTGCAAAA TAGGGCATGA CAGGTGTGAG    12642
GAGCGTGACC ATGATGAGTT GTTAATGTCC ATCCGTCCG GGTACGACAA CCTCAAACTT     12702
GAGGGTTATT ATGCTTGGCT GGCTTTTTTG TCCTTTTCCT ACGCGGCCCA ATTCCATCCG    12762
GAGTTGTTCG GGATAGGGAA TGTGTCGCGC GTCTTCGTGG ACAAGCGACA CCAGTTCATT    12822
TGTGCCGAGC ATGATGGACA CAATTCAACC GTATCTACCG GACACAACAT CTCCGCATTA    12882
TATGCGGCAT ATTACCACCA CCAAATAGAC GGGGCAATT GGTTCCATTT GGAATGGCTG     12942
CGGCCACTCT TTTCTTCCTG GCTGGTGCTC AACATATCAT GGTTTCTGAG GCGTTCGCCT    13002
GTAAGCCCTG TTTCTCGACG CATCTATCAG ATATTGAGAC CAACACGACC GCGGCTGCCG    13062
GTTTCATGGT CCTTCAGGAC ATCAATTGTT TCCGACCTCA CGGGGTCTCA GCAGCGCAAG    13122
AGAAAATTTC CTTCGGAAAG TCGTCCCAAT GTCGTGAAGC CGTCGGTACT CCCCAGTACA    13182
TCACGA TAACGGCTAA CGTGACCGAC GAATCATACT TGTACAACGC GGACCTGCTG        13238
```

| | | | | | | |
|---|---|---|---|---|---|---|
| ATGCTTTCTG | CGTGCCTTTT | CTACGCCTCA | GAAATGAGCG | AGAAAGGCTT | CAAAGTCATC | 13298 |
| TTTGGGAATG | TCTCTGGCGT | TGTTTCTGCT | TGTGTCAATT | TCACAGATTA | TGTGGCCCAT | 13358 |
| GTGACCCAAC | ATACCCAGCA | GCATCATCTG | GTAATTGATC | ACATTCGGTT | GCTGCATTTC | 13418 |
| CTGACACCAT | CTGCAATGAG | GTGGGCTACA | ACCATTGCTT | GTTTGTTCGC | CATTCTCTTG | 13478 |
| GCAATA | TGAGATGTTC | TCACAAATTG | GGGCGTTTCT | TGACTCCGCA | CTCTTGCTTC | 13534 |
| TGGTGGCTTT | TTTTGCTGTG | TACCGGCTTG | TCCTGGTCCT | TTGCCGATGG | CAACGGCGAC | 13594 |
| AGCTCGACAT | ACCAATACAT | ATATAACTTG | ACGATATGCG | AGCTGAATGG | GACCGACTGG | 13654 |
| TTGTCCAGCC | ATTTTGGTTG | GGCAGTCGAG | ACCTTTGTGC | TTTACCCGGT | TGCCACTCAT | 13714 |
| ATCCTCTCAC | TGGGTTTTCT | CACAACAAGC | CATTTTTTG | ACGCGCTCGG | TCTCGGCGCT | 13774 |
| GTATCCACTG | CAGGATTTGT | TGGCGGGCGG | TACGTACTCT | GCAGCGTCTA | CGGCGCTTGT | 13834 |
| GCTTTCGCAG | CGTTCGTATG | TTTTGTCATC | CGTGCTGCTA | AAAATTGCAT | GGCCTGCCGC | 13894 |
| TATGCCCGTA | CCCGGTTTAC | CAACTTCATT | GTGGACGACC | GGGGAGAGT | TCATCGATGG | 13954 |
| AAGTCTCCAA | TAGTGGTAGA | AAAATTGGGC | AAAGCCGAAG | TCGATGGCAA | CCTCGTCACC | 14014 |
| ATCAAACATG | TCGTCCTCGA | AGGGGTTAAA | GCTCAACCCT | TGACGAGGAC | TTCGGCTGAG | 14074 |
| CAATGGGAGG | CC TAGACGATTT | TTGCAACGAT | CCTATCGCCG | CACAAAAGCT | | 14126 |
| CGTGCTAGCC | TTTAGCATCA | CATACACACC | TATAATGATA | TACGCCCTTA | AGGTGTCACG | 14186 |
| CGGCCGACTC | CTGGGGCTGT | TGCACATCCT | AATATTTCTG | AACTGTTCCT | TTACATTCGG | 14246 |
| ATACATGACA | TATGTGCATT | TTCAATCCAC | CAACCGTGTC | GCACTTACCC | TGGGGGCTGT | 14306 |
| TGTCGCCCTT | CTGTGGGGTG | TTTACAGCTT | CACAGAGTCA | TGGAAGTTTA | TCACTTCCAG | 14366 |
| ATGCAGATTG | TGTTGCCTTG | GCCGGCGATA | CATTCTGGCC | CCTGCCCATC | ACGTAGAAAG | 14426 |
| TGCTGCAGGT | CTCCATTCAA | TCTCAGCGTC | TGGTAACCGA | GCATACGCTG | TGAGAAAGCC | 14486 |
| CGGACTAACA | TCAGTGAACG | GCACTCTAGT | ACCAGGACTT | CGGAGCCTCG | TGCTGGGCGG | 14546 |
| CAAACGAGCT | GTTAAACGAG | GAGTGGTTAA | CCTCGTCAAG | TATGGCCGG | TAAAAACCAG | 14605 |
| AGCCAGAAGA | AAAAGAAAAG | TACAGCTCCG | ATGGGGAATG | CCAGCCAGT | CAATCAACTG | 14665 |
| TGCCAGTTGC | TGGGTGCAAT | GATAAAGTCC | CAGCGCCAGC | AACCTAGGGG | AGGACAGGC Y | 14725 |
| AAAAAGAAAA | AGCCTGAGAA | GCCACATTTT | CCCCTGGCTG | CTGAAGATGA | CATCCGGCAC | 14785 |
| CACCTCACCC | AGACTGAACG | CTCCCTCTGC | TTGCAATCGA | TCCAGACGGC | TTTCAATCAA | 14845 |
| GGCGCAGGAA | CTGCGTCRCT | TTCATCCAGC | GGGAAGGTCA | GTTTCAGGT | TGAGTTTATG | 14905 |
| CTGCCGGTTG | CTCATACAGT | GCGCCTGATT | CGCGTGACTT | CTACATCCGC | CAGTCAGGGT | 14965 |
| GCAAGT | TAATTTGACA | GTCAGGTGAA | TGGCCGCGAT | GGCGTGTGGC | CTCTGAGTCA | 15021 |
| CCTATTCAAT | TAGGGCGATC | ACATGGGGGT | CATACTTAAT | TCAGGCAGGA | ACCATGTGAC | 15081 |
| CGAAATTAAA | AAAAAAAAA | AAAAAA | | | | 15108 |

(2) INFORMATION FOR SEQ ID NO:2:

( i ) SEQUENCE CHARACTERISTICS:
        ( A ) LENGTH: 2396 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ser | Gly | Thr | Phe | Ser | Arg | Cys | Met | Cys | Thr | Pro | Ala | Ala | Arg | Val |
|---|---|---|---|---|---|---|---|---|---|---|---|---|---|---|---|
| 1 | | | | 5 | | | | | 10 | | | | | 15 | |

| | | | | | | | | | | | | | | |
|---|---|---|---|---|---|---|---|---|---|---|---|---|---|---|
| Phe | Trp | Asn | Ala<br>20 | Gly | Gln | Val | Phe<br>25 | Cys | Thr | Arg | Cys<br> | Leu | Ser<br>30 | Ala | Arg |
| Ser | Leu | Leu<br>35 | Ser | Pro | Glu | Leu | Gln<br>40 | Asp | Thr | Asp | Leu | Gly<br>45 | Ala | Val | Gly |
| Leu | Phe<br>50 | Tyr | Lys | Pro | Arg | Asp<br>55 | Lys | Leu | His | Trp | Lys<br>60 | Val | Pro | Ile | Gly |
| Ile<br>65 | Pro | Gln | Val | Glu | Cys<br>70 | Thr | Pro | Ser | Gly | Cys<br>75 | Cys | Trp | Leu | Ser | Ala<br>80 |
| Val | Phe | Pro | Leu | Ala<br>85 | Arg | Met | Thr | Ser | Gly<br>90 | Asn | His | Asn | Phe | Leu<br>95 | Gln |
| Arg | Leu | Val | Lys<br>100 | Val | Ala | Asp | Val | Leu<br>105 | Tyr | Arg | Asp | Gly | Cys<br>110 | Leu | Ala |
| Pro | Arg | His<br>115 | Leu | Arg | Glu | Leu | Gln<br>120 | Val | Tyr | Glu | Arg | Gly<br>125 | Cys | Asn | Trp |
| Tyr | Pro<br>130 | Ile | Thr | Gly | Pro | Val<br>135 | Pro | Gly | Met | Gly | Leu<br>140 | Phe | Ala | Asn | Ser |
| Met<br>145 | His | Val | Ser | Asp | Gln<br>150 | Pro | Phe | Pro | Gly | Ala<br>155 | Thr | His | Val | Leu | Thr<br>160 |
| Asn | Ser | Pro | Leu | Pro<br>165 | Gln | Gln | Ala | Cys | Arg<br>170 | Gln | Pro | Phe | Cys | Pro<br>175 | Phe |
| Glu | Glu | Ala | His<br>180 | Ser | Ser | Val | Tyr | Arg<br>185 | Trp | Lys | Lys | Phe | Val<br>190 | Val | Phe |
| Thr | Asp | Ser<br>195 | Ser | Leu | Asn | Gly | Arg<br>200 | Ser | Arg | Met | Met | Trp<br>205 | Thr | Pro | Glu |
| Ser | Asp<br>210 | Asp | Ser | Ala | Ala | Leu<br>215 | Glu | Val | Leu | Pro | Pro<br>220 | Glu | Leu | Glu | Arg |
| Gln<br>225 | Val | Glu | Ile | Leu | Ile<br>230 | Arg | Ser | Phe | Pro | Ala<br>235 | His | His | Pro | Val | Asp<br>240 |
| Leu | Ala | Asp | Trp | Glu<br>245 | Leu | Thr | Glu | Ser | Pro<br>250 | Glu | Asn | Gly | Phe | Ser<br>255 | Phe |
| Asn | Thr | Ser | His<br>260 | Ser | Cys | Gly | His | Leu<br>265 | Val | Gln | Asn | Pro | Asp<br>270 | Val | Phe |
| Asp | Gly | Lys<br>275 | Cys | Trp | Leu | Ser | Cys<br>280 | Phe | Leu | Gly | Gln | Ser<br>285 | Val | Glu | Val |
| Arg | Cys<br>290 | His | Glu | Glu | His | Leu<br>295 | Ala | Asp | Ala | Phe | Gly<br>300 | Tyr | Gln | Thr | Lys |
| Trp<br>305 | Gly | Val | His | Gly | Lys<br>310 | Tyr | Leu | Gln | Arg | Arg<br>315 | Leu | Gln | Val | Arg | Gly<br>320 |
| Ile | Arg | Ala | Val | Val<br>325 | Asp | Pro | Asp | Gly | Pro<br>330 | Ile | His | Val | Glu | Ala<br>335 | Leu |
| Ser | Cys | Pro | Gln<br>340 | Ser | Trp | Ile | Arg | His<br>345 | Leu | Thr | Leu | Asp | Asp<br>350 | Asp | Val |
| Thr | Pro | Gly<br>355 | Phe | Val | Arg | Leu | Thr<br>360 | Ser | Leu | Arg | Ile | Val<br>365 | Pro | Asn | Thr |
| Glu | Pro<br>370 | Thr | Thr | Ser | Arg | Ile<br>375 | Phe | Arg | Phe | Gly | Ala<br>380 | His | Lys | Trp | Tyr |
| Gly<br>385 | Ala | Ala | Gly | Lys | Arg<br>390 | Ala | Arg | Ala | Lys | Arg<br>395 | Ala | Ala | Lys | Ser | Glu<br>400 |
| Lys | Asp | Ser | Ala | Pro<br>405 | Thr | Pro | Lys | Val | Ala<br>410 | Leu | Pro | Val | Pro | Thr<br>415 | Cys |
| Gly | Ile | Thr | Thr<br>420 | Tyr | Ser | Pro | Pro | Thr<br>425 | Asp | Gly | Ser | Cys | Gly<br>430 | Trp | His |
| Val | Leu | Ala | Ala<br>435 | Ile | Met | Asn | Arg | Met<br>440 | Ile | Asn | Gly | Asp | Phe<br>445 | Thr | Ser |

| | | | | | | | | | | | | | | |
|---|---|---|---|---|---|---|---|---|---|---|---|---|---|---|
|Pro|Leu|Thr|Gln|Tyr|Asn|Arg|Pro|Glu|Asp|Asp|Trp|Ala|Ser|Asp|Tyr|
| |450| | | | |455| | | |460| | | | |
|Asp|Leu|Val|Gln|Ala|Ile|Gln|Cys|Leu|Arg|Leu|Pro|Ala|Thr|Val|Val|
|465| | | | |470| | | |475| | | | | |480|
|Arg|Asn|Arg|Ala|Cys|Pro|Asn|Ala|Lys|Tyr|Leu|Ile|Lys|Leu|Asn|Gly|
| | | | |485| | | |490| | | | | |495| |
|Val|His|Trp|Glu|Val|Glu|Val|Arg|Ser|Gly|Met|Ala|Pro|Arg|Ser|Leu|
| | | |500| | | | |505| | | |510| | | |
|Ser|Arg|Glu|Cys|Val|Val|Gly|Val|Cys|Ser|Glu|Gly|Cys|Val|Ala|Pro|
| | |515| | | |520| | | |525| | | | | |
|Pro|Tyr|Pro|Ala|Asp|Gly|Leu|Pro|Lys|Arg|Ala|Leu|Glu|Ala|Leu|Ala|
| |530| | | |535| | | | |540| | | | | |
|Ser|Ala|Tyr|Arg|Leu|Pro|Ser|Asp|Cys|Val|Ser|Ser|Gly|Ile|Ala|Asp|
|545| | | | |550| | | |555| | | | | |560|
|Phe|Leu|Ala|Asn|Pro|Pro|Gln|Glu|Phe|Trp|Thr|Leu|Asp|Lys|Met|
| | | | |565| | |570| | | |575| | | |
|Leu|Thr|Ser|Pro|Ser|Pro|Glu|Arg|Ser|Gly|Phe|Ser|Ser|Leu|Tyr|Lys|
| | | |580| | | |585| | | | |590| | | |
|Leu|Leu|Leu|Glu|Val|Val|Pro|Gln|Lys|Cys|Gly|Ala|Thr|Glu|Gly|Ala|
| | |595| | | |600| | | | |605| | | | |
|Phe|Ile|Tyr|Ala|Val|Glu|Arg|Met|Leu|Lys|Asp|Cys|Pro|Ser|Ser|Lys|
|610| | | | |615| | | | |620| | | | | |
|Gln|Ala|Met|Ala|Leu|Leu|Ala|Lys|Ile|Lys|Val|Pro|Ser|Ser|Lys|Ala|
|625| | | |630| | | | |635| | | | | |640|
|Pro|Ser|Val|Ser|Leu|Asp|Glu|Cys|Phe|Pro|Thr|Asp|Val|Leu|Ala|Asp|
| | | | |645| | | |650| | | | |655| |
|Phe|Glu|Pro|Ala|Ser|Gln|Glu|Arg|Pro|Gln|Ser|Ser|Gly|Ala|Ala|Val|
| | |660| | | | |665| | | |670| | | | |
|Val|Leu|Cys|Ser|Pro|Asp|Ala|Lys|Glu|Phe|Glu|Glu|Ala|Ala|Xaa|Glu|
| |675| | | | |680| | | |685| | | | | |
|Glu|Val|Gln|Glu|Ser|Gly|His|Lys|Ala|Val|His|Ser|Ala|Leu|Leu|Ala|
|690| | | | |695| | | |700| | | | | | |
|Glu|Gly|Pro|Asn|Asn|Glu|Gln|Val|Gln|Val|Val|Ala|Gly|Glu|Gln|Leu|
|705| | | | |710| | | |715| | | | | |720|
|Lys|Leu|Gly|Gly|Cys|Gly|Leu|Ala|Val|Gly|Asn|Ala|His|Glu|Gly|Ala|
| | | | |725| | | |730| | | | |735| | |
|Leu|Val|Ser|Ala|Gly|Leu|Ile|Asn|Leu|Val|Gly|Gly|Asn|Leu|Ser|Pro|
| | | |740| | | |745| | | | |750| | | |
|Ser|Asp|Pro|Met|Lys|Glu|Asn|Met|Leu|Asn|Ser|Arg|Glu|Asp|Glu|Pro|
| | |755| | | | |760| | | | |765| | | |
|Leu|Asp|Leu|Ser|Gln|Pro|Ala|Pro|Ala|Ser|Thr|Thr|Thr|Leu|Val|Arg|
| |770| | | | |775| | | |780| | | | | |
|Glu|Gln|Thr|Pro|Asp|Asn|Pro|Gly|Ser|Asp|Ala|Gly|Ala|Leu|Pro|Val|
|785| | | | |790| | | |795| | | | | |800|
|Thr|Val|Arg|Glu|Phe|Val|Pro|Thr|Gly|Pro|Ile|Leu|Cys|His|Val|Glu|
| | | | |805| | | |810| | | | |815| | |
|His|Cys|Gly|Thr|Glu|Ser|Gly|Asp|Ser|Ser|Ser|Pro|Leu|Asp|Leu|Ser|
| | | |820| | | | |825| | | | |830| | |
|Asp|Ala|Gln|Thr|Leu|Asp|Gln|Pro|Leu|Asn|Leu|Ser|Leu|Ala|Ala|Trp|
| | |835| | | | |840| | | | |845| | | |
|Pro|Val|Arg|Ala|Thr|Ala|Ser|Asp|Pro|Gly|Trp|Val|His|Gly|Arg|Arg|
| |850| | | | |855| | | |860| | | | | |
|Glu|Pro|Val|Phe|Val|Lys|Pro|Arg|Asn|Ala|Phe|Ser|Asp|Gly|Asp|Ser|

-continued

| 865 | | | | 870 | | | | 875 | | | | 880 | |
|---|---|---|---|---|---|---|---|---|---|---|---|---|---|

Ala Leu Gln Phe Gly Glu Leu Ser Glu Ser Ser Val Ile Glu Phe
                  885                 890                 895

Asp Arg Thr Lys Asp Ala Pro Val Val Asp Ala Pro Val Asp Leu Thr
         900                 905                 910

Thr Ser Asn Glu Ala Leu Ser Val Asp Pro Phe Glu Phe Ala Glu
        915              920              925

Leu Lys Arg Pro Arg Phe Ser Ala Gln Ala Leu Ile Asp Arg Gly Gly
    930                935              940

Pro Leu Ala Asp Val His Ala Lys Ile Lys Asn Arg Val Tyr Glu Gln
945              950              955              960

Cys Leu Gln Ala Cys Glu Pro Gly Ser Arg Ala Thr Pro Ala Thr Arg
           965                 970              975

Glu Trp Leu Asp Lys Met Trp Asp Arg Val Asp Met Lys Thr Trp Arg
        980              985              990

Cys Thr Ser Gln Phe Gln Ala Gly Arg Ile Leu Ala Ser Leu Lys Phe
        995            1000             1005

Leu Pro Asp Met Ile Gln Asp Thr Pro Pro Val Pro Arg Lys Asn
    1010              1015             1020

Arg Ala Ser Asp Asn Ala Gly Leu Lys Gln Leu Val Ala Gln Trp Asp
1025             1030             1035             1040

Arg Lys Leu Ser Val Thr Pro Pro Lys Pro Val Gly Pro Val Leu
              1045             1050             1055

Asp Gln Ile Val Pro Pro Thr Asp Ile Gln Gln Glu Asp Val Thr
            1060             1065             1070

Pro Ser Asp Gly Pro Pro His Ala Pro Asp Phe Pro Ser Arg Val Ser
        1075              1080             1085

Thr Gly Gly Ser Trp Lys Gly Leu Met Leu Ser Gly Thr Arg Leu Ala
        1090              1095             1100

Gly Ser Ile Ser Gln Arg Leu Met Thr Trp Val Phe Glu Val Phe Ser
1105             1110             1115             1120

His Leu Pro Ala Phe Met Leu Thr Leu Phe Ser Pro Arg Gly Ser Met
              1125             1130             1135

Ala Pro Gly Asp Trp Leu Phe Ala Gly Val Val Leu Leu Ala Leu Leu
        1140              1145             1150

Leu Cys Arg Ser Tyr Pro Ile Leu Gly Cys Leu Pro Leu Leu Gly Val
        1155              1160             1165

Phe Ser Gly Ser Leu Arg Arg Val Arg Leu Gly Val Phe Gly Ser Trp
        1170              1175             1180

Met Ala Phe Ala Val Phe Leu Phe Ser Thr Pro Ser Asn Pro Val Gly
1185             1190             1195             1200

Ser Ser Cys Asp His Asp Ser Pro Glu Cys His Ala Glu Leu Leu Ala
            1205             1210             1215

Leu Glu Gln Arg Gln Leu Trp Glu Pro Val Arg Gly Leu Val Val Gly
        1220              1225             1230

Pro Ser Gly Leu Leu Cys Val Ile Leu Gly Lys Leu Leu Gly Gly Ser
        1235              1240             1245

Arg Tyr Leu Trp His Val Leu Leu Arg Leu Cys Met Leu Ala Asp Leu
    1250              1255             1260

Ala Leu Ser Leu Val Tyr Val Val Ser Gln Gly Arg Cys His Lys Cys
1265             1270             1275             1280

Trp Gly Lys Cys Ile Arg Thr Ala Pro Ala Glu Val Ala Leu Asn Val
            1285             1290             1295

-continued

```
Phe  Pro  Phe  Ser  Arg  Ala  Thr  Arg  Val  Ser  Leu  Val  Ser  Leu  Cys  Asp
          1300                    1305                    1310

Arg  Phe  Gln  Thr  Pro  Lys  Gly  Val  Asp  Pro  Val  His  Leu  Ala  Thr  Gly
          1315                    1320                    1325

Trp  Arg  Gly  Cys  Trp  Arg  Gly  Glu  Ser  Pro  Ile  His  Gln  Pro  His  Gln
          1330                    1335                    1340

Lys  Pro  Ile  Ala  Tyr  Ala  Asn  Leu  Asp  Glu  Lys  Lys  Met  Ser  Ala  Gln
1345                     1350                    1355                    1360

Thr  Val  Val  Ala  Val  Pro  Tyr  Asp  Pro  Ser  Gln  Ala  Ile  Lys  Cys  Leu
               1365                    1370                    1375

Lys  Val  Leu  Gln  Ala  Gly  Gly  Ala  Ile  Val  Asp  Gln  Pro  Thr  Pro  Glu
               1380                    1385                    1390

Val  Val  Arg  Val  Ser  Glu  Ile  Pro  Phe  Ser  Ala  Pro  Phe  Phe  Pro  Lys
               1395                    1400                    1405

Val  Pro  Val  Asn  Pro  Asp  Cys  Arg  Val  Val  Val  Asp  Ser  Asp  Thr  Phe
1410                     1415                    1420

Val  Ala  Ala  Val  Arg  Cys  Gly  Tyr  Ser  Thr  Ala  Gln  Leu  Xaa  Leu  Gly
1425                     1430                    1435                    1440

Arg  Gly  Asn  Phe  Ala  Lys  Leu  Asn  Gln  Thr  Pro  Pro  Arg  Asn  Ser  Ile
               1445                    1450                    1455

Ser  Thr  Lys  Thr  Thr  Gly  Gly  Ala  Ser  Tyr  Thr  Leu  Ala  Val  Ala  Gln
               1460                    1465                    1470

Val  Ser  Ala  Trp  Thr  Leu  Val  His  Phe  Ile  Leu  Gly  Leu  Trp  Phe  Thr
               1475                    1480                    1485

Ser  Pro  Gln  Val  Cys  Gly  Arg  Gly  Thr  Ala  Asp  Pro  Trp  Cys  Ser  Asn
               1490                    1495                    1500

Pro  Phe  Ser  Tyr  Pro  Thr  Tyr  Gly  Pro  Gly  Val  Val  Cys  Ser  Ser  Arg
1505                     1510                    1515                    1520

Leu  Cys  Val  Ser  Ala  Asp  Gly  Val  Thr  Leu  Pro  Leu  Phe  Ser  Ala  Val
               1525                    1530                    1535

Ala  Gln  Leu  Ser  Gly  Arg  Glu  Val  Gly  Ile  Phe  Ile  Leu  Val  Leu  Val
               1540                    1545                    1550

Ser  Leu  Thr  Ala  Leu  Ala  His  Arg  Met  Ala  Leu  Lys  Ala  Asp  Met  Leu
     1555                    1560                    1565

Val  Val  Phe  Ser  Ala  Phe  Cys  Ala  Tyr  Ala  Trp  Pro  Met  Ser  Ser  Trp
1570                     1575                    1580

Leu  Ile  Cys  Phe  Phe  Pro  Ile  Leu  Leu  Lys  Trp  Val  Thr  Leu  His  Pro
1585                     1590                    1595                    1600

Leu  Thr  Met  Leu  Trp  Val  His  Ser  Phe  Leu  Val  Phe  Cys  Leu  Pro  Ala
          1605                    1610                    1615

Ala  Gly  Ile  Leu  Ser  Leu  Gly  Ile  Thr  Gly  Leu  Leu  Trp  Ala  Ile  Gly
               1620                    1625                    1630

Arg  Phe  Thr  Gln  Val  Ala  Gly  Ile  Ile  Thr  Pro  Tyr  Asp  Ile  His  Gln
          1635                    1640                    1645

Tyr  Thr  Ser  Gly  Pro  Arg  Gly  Ala  Ala  Ala  Val  Ala  Thr  Ala  Pro  Glu
     1650                    1655                    1660

Gly  Thr  Tyr  Met  Ala  Ala  Val  Arg  Arg  Ala  Ala  Leu  Thr  Gly  Arg  Thr
1665                     1670                    1675                    1680

Leu  Ile  Phe  Thr  Pro  Ser  Ala  Val  Gly  Ser  Leu  Leu  Glu  Gly  Ala  Phe
               1685                    1690                    1695

Arg  Thr  His  Lys  Pro  Cys  Leu  Asn  Thr  Val  Asn  Val  Val  Gly  Ser  Ser
               1700                    1705                    1710

Leu  Gly  Ser  Gly  Gly  Val  Phe  Thr  Ile  Asp  Gly  Arg  Arg  Thr  Val  Val
               1715                    1720                    1725
```

```
Thr Ala Ala His Val Leu Asn Gly Asp Thr Ala Arg Val Thr Gly Asp
    1730                1735                1740

Ser Tyr Asn Arg Met His Thr Phe Lys Thr Asn Gly Asp Tyr Ala Trp
1745                1750                1755                1760

Ser His Ala Asp Asp Trp Gln Gly Val Ala Pro Val Val Lys Val Ala
                1765                1770                1775

Lys Gly Tyr Arg Gly Arg Ala Tyr Trp Gln Thr Ser Thr Gly Val Glu
            1780                1785                1790

Pro Gly Ile Ile Gly Glu Gly Phe Ala Phe Cys Phe Thr Asn Cys Gly
            1795                1800                1805

Asp Ser Gly Ser Pro Val Ile Ser Glu Ser Gly Asp Leu Ile Gly Ile
    1810                1815                1820

His Thr Gly Ser Asn Lys Leu Gly Ser Gly Leu Val Thr Thr Pro Glu
1825                1830                1835                1840

Gly Glu Thr Cys Thr Ile Lys Glu Thr Lys Leu Ser Asp Leu Ser Arg
                1845                1850                1855

His Phe Ala Gly Pro Ser Val Pro Leu Gly Asp Ile Lys Leu Ser Pro
            1860                1865                1870

Ala Ile Ile Pro Asp Val Thr Ser Ile Pro Ser Asp Leu Ala Ser Leu
        1875                1880                1885

Leu Ala Ser Val Pro Val Val Glu Gly Gly Leu Ser Thr Val Gln Leu
    1890                1895                1900

Leu Cys Val Phe Phe Leu Leu Trp Arg Met Met Gly His Ala Trp Thr
1905                1910                1915                1920

Pro Ile Val Ala Val Gly Phe Phe Leu Leu Asn Glu Ile Leu Pro Ala
            1925                1930                1935

Val Leu Val Arg Ala Val Phe Ser Phe Ala Leu Phe Val Leu Ala Trp
        1940                1945                1950

Ala Thr Pro Trp Ser Ala Gln Val Leu Met Ile Arg Leu Leu Thr Ala
        1955                1960                1965

Ser Leu Asn Arg Asn Lys Leu Ser Leu Ala Phe Tyr Ala Leu Gly Gly
    1970                1975                1980

Val Val Gly Leu Ala Ala Glu Ile Gly Thr Phe Ala Gly Arg Leu Ser
1985                1990                1995                2000

Glu Leu Ser Gln Ala Leu Ser Thr Tyr Cys Phe Leu Pro Arg Val Leu
                2005                2010                2015

Ala Met Thr Ser Cys Val Pro Thr Ile Ile Ile Gly Gly Leu His Thr
        2020                2025                2030

Leu Gly Val Ile Leu Trp Xaa Phe Lys Tyr Arg Cys Leu His Asn Met
        2035                2040                2045

Leu Val Gly Asp Gly Ser Phe Ser Ser Ala Phe Phe Leu Arg Tyr Phe
    2050                2055                2060

Ala Glu Gly Asn Leu Arg Lys Gly Val Ser Gln Ser Cys Gly Met Asn
2065                2070                2075                2080

Asn Glu Ser Leu Thr Ala Ala Leu Ala Cys Lys Leu Ser Gln Ala Asp
                2085                2090                2095

Leu Asp Phe Leu Ser Ser Leu Thr Asn Phe Lys Cys Phe Val Ser Ala
            2100                2105                2110

Ser Asn Met Lys Asn Ala Ala Gly Gln Tyr Ile Glu Ala Ala Tyr Ala
        2115                2120                2125

Lys Ala Leu Arg Gln Glu Leu Ala Ser Leu Val Gln Ile Asp Lys Met
        2130                2135                2140

Lys Gly Val Leu Ser Lys Leu Glu Ala Phe Ala Glu Thr Ala Thr Pro
```

|      |      |      |      | 2145 |      |      |      |      | 2150 |      |      |      |      | 2155 |      |      |      |      | 2160 |
|------|------|------|------|------|------|------|------|------|------|------|------|------|------|------|------|------|------|------|------|

Ser Leu Asp Ile Gly Asp Val Ile Val Leu Leu Gly Gln His Pro His
                        2165                2170                2175

Gly Ser Ile Leu Asp Ile Asn Val Gly Thr Glu Arg Lys Thr Val Ser
                2180                2185                2190

Val Gln Glu Thr Arg Ser Leu Gly Gly Ser Lys Phe Ser Val Cys Thr
        2195                2200                2205

Val Val Ser Asn Thr Pro Val Asp Ala Xaa Thr Gly Ile Pro Leu Gln
2210                2215                2220

Thr Pro Thr Pro Leu Phe Glu Asn Gly Pro Arg His Arg Ser Glu Glu
2225                2230                2235                2240

Asp Asp Leu Lys Val Glu Arg Met Lys Lys His Cys Val Ser Leu Gly
            2245                2250                2255

Phe His Asn Ile Asn Gly Lys Val Tyr Cys Lys Ile Trp Asp Lys Ser
                2260                2265                2270

Thr Gly Asp Thr Phe Tyr Thr Asp Asp Ser Arg Tyr Thr Gln Asp His
            2275                2280                2285

Ala Phe Gln Asp Arg Ser Ala Asp Tyr Arg Asp Arg Asp Tyr Glu Gly
        2290                2295                2300

Val Gln Thr Thr Pro Gln Gln Gly Phe Asp Pro Lys Ser Glu Thr Pro
2305                2310                2315                2320

Val Gly Thr Val Val Ile Gly Gly Ile Thr Tyr Asn Arg Tyr Leu Ile
                2325                2330                2335

Lys Gly Lys Glu Val Leu Val Pro Lys Pro Asp Asn Cys Leu Glu Ala
            2340                2345                2350

Ala Lys Leu Ser Leu Glu Gln Ala Leu Ala Gly Met Gly Gln Thr Cys
        2355                2360                2365

Asp Leu Thr Ala Ala Glu Val Glu Lys Leu Lys Arg Ile Ile Ser Gln
    2370                2375                2380

Leu Gln Gly Leu Thr Thr Glu Gln Ala Leu Asn Cys
2385                2390                2395

(2) INFORMATION FOR SEQ ID NO:3:

( i ) SEQUENCE CHARACTERISTICS:
        ( A ) LENGTH: 1463 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Thr Gly Phe Lys Leu Leu Ala Ala Ser Gly Leu Thr Arg Cys Gly Arg
 1               5                  10                  15

Gly Gly Leu Val Val Thr Glu Thr Ala Val Lys Ile Ile Lys Tyr His
            20                  25                  30

Ser Arg Thr Phe Thr Leu Gly Pro Leu Asp Leu Lys Val Thr Ser Glu
        35                  40                  45

Val Glu Val Lys Lys Ser Thr Glu Gln Gly His Ala Val Val Ala Asn
    50                  55                  60

Leu Cys Ser Gly Val Ile Leu Met Arg Pro His Pro Pro Ser Leu Val
65                  70                  75                  80

Asp Val Leu Leu Lys Pro Gly Leu Asp Thr Ile Pro Gly Ile Gln Pro
                85                  90                  95

Gly His Gly Ala Gly Asn Met Gly Val Asp Gly Ser Ile Trp Asp Phe
            100                 105                 110

```
Glu  Thr  Ala  Pro  Thr  Lys  Ala  Glu  Leu  Glu  Leu  Ser  Lys  Gln  Ile  Ile
          115                 120                      125

Gln  Ala  Cys  Glu  Val  Arg  Arg  Gly  Asp  Ala  Pro  Asn  Leu  Gln  Leu  Pro
     130                 135                 140

Tyr  Lys  Leu  Tyr  Pro  Val  Arg  Gly  Asp  Pro  Glu  Arg  His  Lys  Gly  Arg
145                      150                 155                           160

Leu  Ile  Asn  Thr  Arg  Phe  Gly  Asp  Leu  Pro  Tyr  Lys  Thr  Pro  Gln  Asp
               165                      170                      175

Thr  Lys  Ser  Ala  Ile  His  Ala  Ala  Cys  Cys  Leu  His  Pro  Asn  Gly  Ala
               180                      185                      190

Pro  Val  Ser  Asp  Gly  Lys  Ser  Thr  Leu  Gly  Thr  Thr  Leu  Gln  His  Gly
          195                      200                      205

Phe  Glu  Leu  Tyr  Val  Pro  Thr  Val  Pro  Tyr  Ser  Val  Met  Glu  Tyr  Leu
          210                      215                      220

Asp  Ser  Arg  Pro  Asp  Thr  Pro  Phe  Met  Cys  Thr  Lys  His  Gly  Thr  Ser
225                      230                 235                           240

Lys  Ala  Ala  Ala  Glu  Asp  Leu  Gln  Lys  Tyr  Asp  Leu  Ser  Thr  Gln  Gly
               245                      250                      255

Phe  Val  Leu  Pro  Gly  Val  Leu  Arg  Leu  Val  Arg  Arg  Phe  Ile  Phe  Gly
          260                      265                      270

His  Ile  Gly  Lys  Ala  Pro  Pro  Leu  Phe  Leu  Pro  Ser  Thr  Tyr  Pro  Ala
          275                      280                      285

Lys  Asn  Ser  Met  Ala  Gly  Ile  Asn  Gly  Gln  Arg  Phe  Pro  Thr  Lys  Asp
     290                      295                      300

Val  Gln  Ser  Ile  Pro  Glu  Ile  Asp  Glu  Met  Cys  Ala  Arg  Ala  Val  Lys
305                      310                 315                           320

Glu  Asn  Trp  Gln  Thr  Val  Thr  Pro  Cys  Thr  Leu  Lys  Lys  Gln  Tyr  Cys
                    325                 330                      335

Ser  Lys  Pro  Lys  Thr  Arg  Thr  Ile  Leu  Gly  Thr  Asn  Asn  Phe  Ile  Ala
               340                 345                      350

Leu  Ala  His  Arg  Ser  Ala  Leu  Ser  Gly  Val  Thr  Gln  Ala  Phe  Met  Lys
          355                      360                      365

Lys  Ala  Trp  Lys  Ser  Pro  Ile  Ala  Leu  Gly  Lys  Asn  Lys  Phe  Lys  Glu
370                           375                      380

Leu  His  Cys  Thr  Val  Ala  Gly  Arg  Cys  Leu  Glu  Ala  Asp  Leu  Ala  Ser
385                      390                 395                           400

Cys  Asp  Arg  Ser  Thr  Pro  Ala  Ile  Val  Arg  Trp  Phe  Val  Ala  Asn  Leu
               405                      410                      415

Leu  Tyr  Glu  Leu  Ala  Gly  Cys  Glu  Glu  Tyr  Leu  Pro  Ser  Tyr  Val  Leu
          420                      425                      430

Asn  Cys  Cys  His  Asp  Leu  Val  Ala  Thr  Gln  Asp  Gly  Ala  Phe  Thr  Lys
          435                      440                      445

Arg  Gly  Gly  Leu  Ser  Ser  Gly  Asp  Pro  Val  Thr  Ser  Val  Ser  Asn  Thr
     450                      455                      460

Val  Tyr  Ser  Leu  Val  Ile  Tyr  Ala  Gln  His  Met  Val  Leu  Ser  Ala  Leu
465                      470                      475                      480

Lys  Met  Gly  His  Glu  Ile  Gly  Leu  Lys  Phe  Leu  Glu  Glu  Gln  Leu  Lys
                    485                      490                      495

Phe  Glu  Asp  Leu  Leu  Glu  Ile  Gln  Pro  Met  Leu  Val  Tyr  Ser  Asp  Asp
               500                      505                      510

Leu  Val  Leu  Tyr  Ala  Glu  Arg  Pro  Xaa  Phe  Pro  Asn  Tyr  His  Trp  Trp
          515                      520                 525

Val  Glu  His  Leu  Asp  Leu  Met  Leu  Gly  Phe  Arg  Thr  Asp  Pro  Lys  Lys
          530                 535                      540
```

| | | | | | | | | | | | | | | |
|---|---|---|---|---|---|---|---|---|---|---|---|---|---|---|
| Thr | Val | Ile | Thr | Asp | Lys | Pro | Ser | Phe | Leu | Gly | Cys | Arg | Ile | Glu | Ala |
| 545 | | | | | 550 | | | | | 555 | | | | | 560 |
| Gly | Arg | Gln | Leu | Val | Pro | Asn | Arg | Asp | Arg | Ile | Leu | Ala | Ala | Leu | Ala |
| | | | | 565 | | | | | 570 | | | | | 575 | |
| Tyr | His | Met | Lys | Ala | Gln | Asn | Ala | Ser | Glu | Tyr | Tyr | Ala | Ser | Ala | Ala |
| | | | 580 | | | | | 585 | | | | | 590 | | |
| Ala | Ile | Leu | Met | Asp | Ser | Cys | Ala | Cys | Ile | Asp | His | Asp | Pro | Glu | Trp |
| | | 595 | | | | | 600 | | | | | 605 | | | |
| Tyr | Glu | Asp | Leu | Ile | Cys | Gly | Ile | Ala | Arg | Cys | Ala | Arg | Gln | Asp | Gly |
| | 610 | | | | | 615 | | | | | 620 | | | | |
| Tyr | Ser | Phe | Pro | Gly | Pro | Ala | Phe | Phe | Met | Ser | Met | Trp | Glu | Lys | Leu |
| 625 | | | | | 630 | | | | | 635 | | | | | 640 |
| Arg | Ser | His | Asn | Glu | Gly | Lys | Lys | Phe | Arg | His | Cys | Gly | Ile | Cys | Asp |
| | | | | 645 | | | | | 650 | | | | | 655 | |
| Ala | Lys | Ala | Asp | Tyr | Ala | Ser | Ala | Cys | Gly | Leu | Asp | Leu | Cys | Leu | Phe |
| | | | 660 | | | | | 665 | | | | | 670 | | |
| His | Ser | His | Phe | His | Gln | His | Cys | Xaa | Val | Thr | Leu | Ser | Cys | Gly | His |
| | | 675 | | | | | 680 | | | | | 685 | | | |
| His | Ala | Gly | Ser | Lys | Glu | Cys | Ser | Gln | Cys | Gln | Ser | Pro | Val | Gly | Ala |
| | 690 | | | | | 695 | | | | | 700 | | | | |
| Gly | Arg | Ser | Pro | Leu | Asp | Ala | Val | Leu | Lys | Gln | Ile | Pro | Tyr | Lys | Pro |
| 705 | | | | | 710 | | | | | 715 | | | | | 720 |
| Pro | Arg | Thr | Val | Ile | Met | Lys | Val | Gly | Asn | Lys | Thr | Thr | Ala | Leu | Asp |
| | | | | 725 | | | | | 730 | | | | | 735 | |
| Pro | Gly | Arg | Tyr | Gln | Ser | Arg | Arg | Gly | Leu | Val | Ala | Val | Lys | Arg | Gly |
| | | | 740 | | | | | 745 | | | | | 750 | | |
| Ile | Ala | Gly | Asn | Glu | Val | Asp | Leu | Ser | Asp | Xaa | Asp | Tyr | Gln | Val | Val |
| | | 755 | | | | | 760 | | | | | 765 | | | |
| Pro | Leu | Leu | Pro | Thr | Cys | Lys | Asp | Ile | Asn | Met | Val | Lys | Val | Ala | Cys |
| | 770 | | | | | 775 | | | | | 780 | | | | |
| Asn | Val | Leu | Leu | Ser | Lys | Phe | Ile | Val | Gly | Pro | Pro | Gly | Ser | Gly | Lys |
| 785 | | | | | 790 | | | | | 795 | | | | | 800 |
| Thr | Thr | Trp | Leu | Leu | Ser | Gln | Val | Gln | Asp | Asp | Asp | Val | Ile | Tyr | Xaa |
| | | | | 805 | | | | | 810 | | | | | 815 | |
| Pro | Thr | His | Gln | Thr | Met | Phe | Asp | Ile | Val | Ser | Ala | Leu | Lys | Val | Cys |
| | | | 820 | | | | | 825 | | | | | 830 | | |
| Arg | Tyr | Ser | Ile | Pro | Gly | Ala | Ser | Gly | Leu | Pro | Phe | Pro | Pro | Pro | Ala |
| | | 835 | | | | | 840 | | | | | 845 | | | |
| Arg | Ser | Gly | Pro | Trp | Val | Arg | Leu | Ile | Ala | Ser | Gly | His | Val | Pro | Gly |
| | 850 | | | | | 855 | | | | | 860 | | | | |
| Arg | Val | Ser | Tyr | Leu | Asp | Glu | Ala | Gly | Tyr | Cys | Asn | His | Leu | Asp | Ile |
| 865 | | | | | 870 | | | | | 875 | | | | | 880 |
| Leu | Arg | Leu | Leu | Ser | Lys | Thr | Pro | Leu | Val | Cys | Leu | Gly | Asp | Leu | Gln |
| | | | | 885 | | | | | 890 | | | | | 895 | |
| Gln | Leu | His | Pro | Val | Gly | Phe | Asp | Ser | Tyr | Cys | Tyr | Val | Phe | Asp | Gln |
| | | | 900 | | | | | 905 | | | | | 910 | | |
| Met | Pro | Gln | Lys | Gln | Leu | Thr | Thr | Ile | Tyr | Arg | Phe | Gly | Pro | Asn | Ile |
| | | 915 | | | | | 920 | | | | | 925 | | | |
| Cys | Ala | Arg | Ile | Gln | Pro | Cys | Tyr | Arg | Glu | Lys | Leu | Glu | Ser | Lys | Ala |
| | 930 | | | | | 935 | | | | | 940 | | | | |
| Arg | Asn | Thr | Arg | Val | Val | Phe | Thr | Thr | Arg | Pro | Val | Ala | Phe | Gly | Gln |
| 945 | | | | | 950 | | | | | 955 | | | | | 960 |
| Val | Leu | Thr | Pro | Tyr | His | Lys | Asp | Arg | Ile | Gly | Ser | Ala | Ile | Thr | Ile |

|     |     |     |     |     |     |     | 965 |     |     |     |     |     | 970 |     |     |     |     |     | 975 |     |
| --- | --- | --- | --- | --- | --- | --- | --- | --- | --- | --- | --- | --- | --- | --- | --- | --- | --- | --- | --- | --- |

```
Asp  Ser  Ser  Gln  Gly  Ala  Thr  Phe  Asp  Ile  Val  Thr  Leu  His  Leu  Pro
               980                      985                     990
Ser  Pro  Lys  Ser  Leu  Asn  Lys  Ser  Arg  Ala  Leu  Val  Ala  Ile  Thr  Arg
          995                      1000                    1005
Ala  Arg  His  Gly  Leu  Phe  Ile  Tyr  Asp  Pro  His  Asn  Gln  Leu  Gln  Glu
     1010                     1015                    1020
Phe  Phe  Asn  Leu  Thr  Pro  Glu  Arg  Thr  Asp  Cys  Asn  Leu  Val  Phe  Ser
1025                     1030                     1035                    1040
Arg  Gly  Asp  Glu  Leu  Val  Val  Leu  Asn  Ala  Asp  Asn  Ala  Val  Thr  Thr
                    1045                     1050                    1055
Val  Ala  Lys  Ala  Leu  Glu  Thr  Gly  Pro  Ser  Arg  Phe  Arg  Val  Ser  Asp
                    1060                     1065                    1070
Pro  Arg  Cys  Lys  Ser  Leu  Leu  Ala  Ala  Cys  Ser  Ala  Ser  Leu  Glu  Gly
                    1075                     1080                    1085
Ser  Cys  Met  Pro  Leu  Pro  Gln  Val  Ala  His  Asn  Leu  Gly  Phe  Tyr  Phe
               1090                     1095                    1100
Ser  Pro  Asp  Ser  Pro  Thr  Phe  Ala  Pro  Leu  Pro  Lys  Glu  Leu  Ala  Pro
1105                     1110                     1115                   1120
His  Trp  Pro  Val  Val  Thr  His  Gln  Asn  Asn  Arg  Ala  Trp  Pro  Asp  Arg
                    1125                     1130                    1135
Leu  Val  Ala  Ser  Met  Arg  Pro  Ile  Asp  Ala  Arg  Tyr  Ser  Lys  Pro  Met
                    1140                     1145                    1150
Val  Gly  Ala  Gly  Tyr  Val  Val  Gly  Pro  Ser  Thr  Phe  Leu  Gly  Thr  Pro
               1155                     1160                    1165
Gly  Val  Val  Ser  Tyr  Tyr  Leu  Thr  Leu  Tyr  Ile  Arg  Gly  Glu  Pro  Gln
          1170                     1175                    1180
Ala  Leu  Pro  Glu  Thr  Leu  Val  Ser  Thr  Gly  Arg  Ile  Ala  Thr  Asp  Cys
1185                     1190                     1195                   1200
Arg  Glu  Tyr  Leu  Asp  Ala  Ala  Glu  Glu  Ala  Ala  Lys  Glu  Leu  Pro
                    1205                     1210                    1215
His  Ala  Phe  Ile  Gly  Asp  Val  Lys  Gly  Thr  Thr  Val  Gly  Gly  Cys  His
          1220                     1225                    1230
His  Ile  Thr  Ser  Lys  Tyr  Leu  Pro  Arg  Ser  Leu  Pro  Lys  Asp  Ser  Val
          1235                     1240                    1245
Ala  Val  Val  Gly  Val  Ser  Ser  Pro  Gly  Arg  Ala  Ala  Lys  Ala  Val  Cys
     1250                     1255                    1260
Thr  Leu  Thr  Asp  Val  Tyr  Leu  Pro  Glu  Leu  Arg  Pro  Tyr  Leu  Gln  Pro
1265                     1270                     1275                   1280
Glu  Thr  Ala  Ser  Lys  Cys  Trp  Lys  Leu  Lys  Leu  Asp  Phe  Arg  Asp  Val
                    1285                     1290                    1295
Arg  Leu  Met  Val  Trp  Lys  Gly  Ala  Thr  Ala  Tyr  Phe  Gln  Leu  Glu  Gly
               1300                     1305                    1310
Leu  Thr  Trp  Ser  Ala  Leu  Pro  Asp  Tyr  Ala  Arg  Xaa  Ile  Gln  Leu  Pro
          1315                     1320                    1325
Lys  Asp  Ala  Val  Val  Tyr  Ile  Asp  Pro  Cys  Ile  Gly  Pro  Ala  Thr  Ala
1330                     1335                     1340
Asn  Arg  Lys  Val  Val  Arg  Thr  Thr  Asp  Trp  Arg  Ala  Asp  Leu  Ala  Val
1345                     1350                     1355                   1360
Thr  Pro  Tyr  Asp  Tyr  Gly  Ala  Gln  Asn  Ile  Leu  Thr  Thr  Ala  Trp  Phe
                    1365                     1370                    1375
Glu  Asp  Leu  Gly  Pro  Gln  Trp  Lys  Ile  Leu  Gly  Leu  Gln  Pro  Phe  Arg
               1380                     1385                    1390
```

```
Arg Ala Phe Gly Phe Glu Asn Thr Glu Asp Trp Ala Ile Leu Ala Arg
         1395                1400               1405

Arg Met Asn Asp Gly Lys Asp Tyr Thr Asp Tyr Asn Trp Asn Cys Val
         1410                1415               1420

Arg Glu Arg Pro His Ala Ile Tyr Gly Arg Ala Arg Asp His Thr Tyr
1425                1430                1435               1440

His Phe Ala Pro Gly Thr Glu Leu Gln Val Glu Leu Gly Lys Pro Arg
                1445                1450               1455

Leu Pro Pro Gly Gln Val Pro
                1460
```

( 2 ) INFORMATION FOR SEQ ID NO:4:

( i ) SEQUENCE CHARACTERISTICS:
        ( A ) LENGTH: 249 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Gln Trp Gly His Cys Gly Val Lys Ser Ala Ser Cys Ser Trp Thr
1               5                  10                  15

Pro Ser Leu Ser Ser Leu Leu Val Trp Leu Ile Leu Xaa Phe Ser Leu
            20                  25                  30

Pro Tyr Cys Leu Gly Ser Pro Ser Gln Asp Gly Tyr Trp Ser Phe Phe
            35                  40                  45

Ser Glu Trp Phe Ala Pro Arg Phe Ser Val Arg Ala Leu Pro Phe Thr
    50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Val Lys His Pro Leu Xaa Met Phe Trp
                85                  90                  95

His Met Arg Val Ser His Leu Ile Asp Glu Xaa Val Ser Arg Arg Ile
                100                 105                 110

Tyr Gln Thr Met Glu His Ser Gly Gln Ala Ala Trp Lys Gln Val Val
            115                 120                 125

Gly Glu Ala Thr Leu Thr Lys Leu Ser Gly Leu Asp Ile Val Thr His
130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Ile
    210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245
```

( 2 ) INFORMATION FOR SEQ ID NO:5:

( i ) SEQUENCE CHARACTERISTICS:
        ( A ) LENGTH: 265 amino acids (B) TYPE: amino acid
(D) TOPOLOGY: linear (ii) MOLECULE TYPE: protein (xi) SEQUENCE DESCRIPTION: SEQ ID NO:5:

| Met | Ala | His | Gln | Cys | Ala | Arg | Phe | His | Phe | Phe | Leu | Cys | Gly | Phe | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Cys | Tyr | Leu | Val | His | Ser | Ala | Leu | Ala | Ser | Asn | Ser | Ser | Ser | Thr | Leu |
|     |     |     | 20  |     |     |     |     | 25  |     |     |     |     | 30  |     |     |
| Cys | Phe | Trp | Phe | Pro | Leu | Ala | His | Gly | Asn | Thr | Ser | Phe | Glu | Leu | Thr |
|     |     | 35  |     |     |     |     | 40  |     |     |     |     | 45  |     |     |     |
| Ile | Asn | Tyr | Thr | Ile | Cys | Met | Pro | Cys | Ser | Thr | Ser | Gln | Ala | Ala | Arg |
|     | 50  |     |     |     |     | 55  |     |     |     |     | 60  |     |     |     |     |
| Gln | Arg | Leu | Glu | Pro | Gly | Arg | Asn | Met | Trp | Cys | Lys | Ile | Gly | His | Asp |
| 65  |     |     |     |     | 70  |     |     |     |     | 75  |     |     |     |     | 80  |
| Arg | Cys | Glu | Glu | Arg | Asp | His | Asp | Glu | Leu | Leu | Met | Ser | Ile | Pro | Ser |
|     |     |     |     | 85  |     |     |     |     | 90  |     |     |     |     | 95  |     |
| Gly | Tyr | Asp | Asn | Leu | Lys | Leu | Glu | Gly | Tyr | Tyr | Ala | Trp | Leu | Ala | Phe |
|     |     |     | 100 |     |     |     |     | 105 |     |     |     |     | 110 |     |     |
| Leu | Ser | Phe | Ser | Tyr | Ala | Ala | Gln | Phe | His | Pro | Glu | Leu | Phe | Gly | Ile |
|     |     | 115 |     |     |     |     | 120 |     |     |     |     | 125 |     |     |     |
| Gly | Asn | Val | Ser | Arg | Val | Phe | Val | Asp | Lys | Arg | His | Gln | Phe | Ile | Cys |
|     | 130 |     |     |     |     | 135 |     |     |     |     | 140 |     |     |     |     |
| Ala | Glu | His | Asp | Gly | His | Asn | Ser | Thr | Val | Ser | Thr | Gly | His | Asn | Ile |
| 145 |     |     |     |     | 150 |     |     |     |     | 155 |     |     |     |     | 160 |
| Ser | Ala | Leu | Tyr | Ala | Ala | Tyr | Tyr | His | His | Gln | Ile | Asp | Gly | Gly | Asn |
|     |     |     |     | 165 |     |     |     |     | 170 |     |     |     |     | 175 |     |
| Trp | Phe | His | Leu | Glu | Trp | Leu | Arg | Pro | Leu | Phe | Ser | Ser | Trp | Leu | Val |
|     |     |     | 180 |     |     |     |     | 185 |     |     |     |     | 190 |     |     |
| Leu | Asn | Ile | Ser | Trp | Phe | Leu | Arg | Arg | Ser | Pro | Val | Ser | Pro | Val | Ser |
|     |     | 195 |     |     |     |     | 200 |     |     |     |     | 205 |     |     |     |
| Arg | Arg | Ile | Tyr | Gln | Ile | Leu | Arg | Pro | Thr | Arg | Pro | Arg | Leu | Pro | Val |
|     | 210 |     |     |     |     | 215 |     |     |     |     | 220 |     |     |     |     |
| Ser | Trp | Ser | Phe | Arg | Thr | Ser | Ile | Val | Ser | Asp | Leu | Thr | Gly | Ser | Gln |
| 225 |     |     |     |     | 230 |     |     |     |     | 235 |     |     |     |     | 240 |
| Gln | Arg | Lys | Arg | Lys | Phe | Pro | Ser | Glu | Ser | Arg | Pro | Asn | Val | Val | Lys |
|     |     |     |     | 245 |     |     |     |     | 250 |     |     |     |     | 255 |     |
| Pro | Ser | Val | Leu | Pro | Ser | Thr | Ser | Arg |     |     |     |     |     |     |     |
|     |     |     | 260 |     |     |     |     | 265 |     |     |     |     |     |     |     |

(2) INFORMATION FOR SEQ ID NO:6:

(i) SEQUENCE CHARACTERISTICS:
(A) LENGTH: 183 amino acids
(B) TYPE: amino acid
(D) TOPOLOGY: linear (ii) MOLECULE TYPE: protein (xi) SEQUENCE DESCRIPTION: SEQ ID NO:6:

| Met | Ala | Ala | Ala | Thr | Leu | Phe | Phe | Leu | Ala | Gly | Ala | Gln | His | Ile | Met |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Val | Ser | Glu | Ala | Phe | Ala | Cys | Lys | Pro | Cys | Phe | Ser | Thr | His | Leu | Ser |
|     |     |     | 20  |     |     |     |     | 25  |     |     |     |     | 30  |     |     |
| Asp | Ile | Glu | Thr | Asn | Thr | Thr | Ala | Ala | Ala | Gly | Phe | Met | Val | Leu | Gln |
|     |     |     | 35  |     |     |     |     | 40  |     |     |     |     | 45  |     |     |
| Asp | Ile | Asn | Cys | Phe | Arg | Pro | His | Gly | Val | Ser | Ala | Ala | Gln | Glu | Lys |

```
                   50                        55                          60
Ile  Ser  Phe  Gly  Lys  Ser  Ser  Gln  Cys  Arg  Glu  Ala  Val  Gly  Thr  Pro
 65                      70                      75                           80

Gln  Tyr  Ile  Thr  Ile  Thr  Ala  Asn  Val  Thr  Asp  Glu  Ser  Tyr  Leu  Tyr
                     85                      90                      95

Asn  Ala  Asp  Leu  Leu  Met  Leu  Ser  Ala  Cys  Leu  Phe  Tyr  Ala  Ser  Glu
               100                     105                    110

Met  Ser  Glu  Lys  Gly  Phe  Lys  Val  Ile  Phe  Gly  Asn  Val  Ser  Gly  Val
          115                     120                    125

Val  Ser  Ala  Cys  Val  Asn  Phe  Thr  Asp  Tyr  Val  Ala  His  Val  Thr  Gln
     130                    135                    140

His  Thr  Gln  Gln  His  His  Leu  Val  Ile  Asp  His  Ile  Arg  Leu  Leu  His
145                      150                    155                          160

Phe  Leu  Thr  Pro  Ser  Ala  Met  Arg  Trp  Ala  Thr  Thr  Ile  Ala  Cys  Leu
               165                     170                    175

Phe  Ala  Ile  Leu  Leu  Ala  Ile
               180
```

( 2 ) INFORMATION FOR SEQ ID NO:7:

( i ) SEQUENCE CHARACTERISTICS:
        ( A ) LENGTH: 201 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Arg  Cys  Ser  His  Lys  Leu  Gly  Arg  Phe  Leu  Thr  Pro  His  Ser  Cys
 1                       5                      10                           15

Phe  Trp  Trp  Leu  Phe  Leu  Leu  Cys  Thr  Gly  Leu  Ser  Trp  Ser  Phe  Ala
               20                      25                     30

Asp  Gly  Asn  Gly  Asp  Ser  Ser  Thr  Tyr  Gln  Tyr  Ile  Tyr  Asn  Leu  Thr
          35                      40                     45

Ile  Cys  Glu  Leu  Asn  Gly  Thr  Asp  Trp  Leu  Ser  Ser  His  Phe  Gly  Trp
     50                      55                     60

Ala  Val  Glu  Thr  Phe  Val  Leu  Tyr  Pro  Val  Ala  Thr  His  Ile  Leu  Ser
 65                      70                     75                           80

Leu  Gly  Phe  Leu  Thr  Thr  Ser  His  Phe  Phe  Asp  Ala  Leu  Gly  Leu  Gly
               85                     90                     95

Ala  Val  Ser  Thr  Ala  Gly  Phe  Val  Gly  Gly  Arg  Tyr  Val  Leu  Cys  Ser
               100                    105                    110

Val  Tyr  Gly  Ala  Cys  Ala  Phe  Ala  Ala  Phe  Val  Cys  Phe  Val  Ile  Arg
          115                    120                    125

Ala  Ala  Lys  Asn  Cys  Met  Ala  Cys  Arg  Tyr  Ala  Arg  Thr  Arg  Phe  Thr
     130                    135                    140

Asn  Phe  Ile  Val  Asp  Asp  Arg  Gly  Arg  Val  His  Arg  Trp  Lys  Ser  Pro
145                      150                    155                          160

Ile  Val  Val  Glu  Lys  Leu  Gly  Lys  Ala  Glu  Val  Asp  Gly  Asn  Leu  Val
               165                    170                    175

Thr  Ile  Lys  His  Val  Val  Leu  Glu  Gly  Val  Lys  Ala  Gln  Pro  Leu  Thr
               180                    185                    190

Arg  Thr  Ser  Ala  Glu  Gln  Trp  Glu  Ala
          195                    200
```

( 2 ) INFORMATION FOR SEQ ID NO:8:

( i ) SEQUENCE CHARACTERISTICS:
: ( A ) LENGTH: 173 amino acids
: ( B ) TYPE: amino acid
: ( D ) TOPOLOGY: linear ( i i ) MOLECULE TYPE: protein ( x i ) SEQUENCE DESCRIPTION: SEQ ID NO:8:

| Met | Gly | Gly | Leu | Asp | Asp | Phe | Cys | Asn | Asp | Pro | Ile | Ala | Ala | Gln | Lys |
|---|---|---|---|---|---|---|---|---|---|---|---|---|---|---|---|
| 1 | | | | 5 | | | | | 10 | | | | | | 15 |
| Leu | Val | Leu | Ala | Phe | Ser | Ile | Thr | Tyr | Thr | Pro | Ile | Met | Ile | Tyr | Ala |
| | | | 20 | | | | | 25 | | | | | 30 | | |
| Leu | Lys | Val | Ser | Arg | Gly | Arg | Leu | Leu | Gly | Leu | Leu | His | Ile | Leu | Ile |
| | | 35 | | | | | 40 | | | | | 45 | | | |
| Phe | Leu | Asn | Cys | Ser | Phe | Thr | Phe | Gly | Tyr | Met | Thr | Tyr | Val | His | Phe |
| | 50 | | | | | 55 | | | | | 60 | | | | |
| Gln | Ser | Thr | Asn | Arg | Val | Ala | Leu | Thr | Leu | Gly | Ala | Val | Val | Ala | Leu |
| 65 | | | | | 70 | | | | | 75 | | | | | 80 |
| Leu | Trp | Gly | Val | Tyr | Ser | Phe | Thr | Glu | Ser | Trp | Lys | Phe | Ile | Thr | Ser |
| | | | | 85 | | | | | 90 | | | | | 95 | |
| Arg | Cys | Arg | Leu | Cys | Cys | Leu | Gly | Arg | Arg | Tyr | Ile | Leu | Ala | Pro | Ala |
| | | | 100 | | | | | 105 | | | | | 110 | | |
| His | His | Val | Glu | Ser | Ala | Ala | Gly | Leu | His | Ser | Ile | Ser | Ala | Ser | Gly |
| | | 115 | | | | | 120 | | | | | 125 | | | |
| Asn | Arg | Ala | Tyr | Ala | Val | Arg | Lys | Pro | Gly | Leu | Thr | Ser | Val | Asn | Gly |
| | 130 | | | | | 135 | | | | | 140 | | | | |
| Thr | Leu | Val | Pro | Gly | Leu | Arg | Ser | Leu | Val | Leu | Gly | Gly | Lys | Arg | Ala |
| 145 | | | | | 150 | | | | | 155 | | | | | 160 |
| Val | Lys | Arg | Gly | Val | Val | Asn | Leu | Val | Lys | Tyr | Gly | Arg | | | |
| | | | | 165 | | | | | 170 | | | | | | |

( 2 ) INFORMATION FOR SEQ ID NO:9:

( i ) SEQUENCE CHARACTERISTICS:
: ( A ) LENGTH: 128 amino acids
: ( B ) TYPE: amino acid
: ( D ) TOPOLOGY: linear ( i i ) MOLECULE TYPE: protein ( x i ) SEQUENCE DESCRIPTION: SEQ ID NO:9:

| Met | Ala | Gly | Lys | Asn | Gln | Ser | Gln | Lys | Lys | Lys | Lys | Ser | Thr | Ala | Pro |
|---|---|---|---|---|---|---|---|---|---|---|---|---|---|---|---|
| 1 | | | | 5 | | | | | 10 | | | | | | 15 |
| Met | Gly | Asn | Gly | Gln | Pro | Val | Asn | Gln | Leu | Cys | Gln | Leu | Leu | Gly | Ala |
| | | | 20 | | | | | 25 | | | | | 30 | | |
| Met | Ile | Lys | Ser | Gln | Arg | Gln | Gln | Pro | Arg | Gly | Gly | Gln | Xaa | Lys | Lys |
| | | 35 | | | | | 40 | | | | | 45 | | | |
| Lys | Lys | Pro | Glu | Lys | Pro | His | Phe | Pro | Leu | Ala | Ala | Glu | Asp | Asp | Ile |
| | 50 | | | | | 55 | | | | | 60 | | | | |
| Arg | His | His | Leu | Thr | Gln | Thr | Glu | Arg | Ser | Leu | Cys | Leu | Gln | Ser | Ile |
| 65 | | | | | 70 | | | | | 75 | | | | | 80 |
| Gln | Thr | Ala | Phe | Asn | Gln | Gly | Ala | Gly | Thr | Ala | Xaa | Leu | Ser | Ser | Ser |
| | | | | 85 | | | | | 90 | | | | | 95 | |
| Gly | Lys | Val | Ser | Phe | Gln | Val | Glu | Phe | Met | Leu | Pro | Val | Ala | His | Thr |
| | | | 100 | | | | | 105 | | | | | 110 | | |
| Val | Arg | Leu | Ile | Arg | Val | Thr | Ser | Thr | Ser | Ala | Ser | Gln | Gly | Ala | Ser |
| | | 115 | | | | | 120 | | | | | 125 | | | |